United States Patent
Mansfield et al.

(10) Patent No.: US 10,544,162 B2
(45) Date of Patent: Jan. 28, 2020

(54) POLYMORPHIC FORM OF TG02

(71) Applicant: Adastra Pharmaceuticals, Inc., Princeton, NJ (US)

(72) Inventors: Robert K. Mansfield, San Marcos, CA (US); Tracy Parrott, San Diego, CA (US)

(73) Assignee: ADASTRA PHARMACEUTICALS, INC., Princeton, NJ (US)

(*) Notice: Subject to any disclaimer, the term of this patent is extended or adjusted under 35 U.S.C. 154(b) by 0 days.

(21) Appl. No.: 15/998,872

(22) Filed: Aug. 17, 2018

(65) Prior Publication Data
US 2019/0055263 A1 Feb. 21, 2019

Related U.S. Application Data

(60) Provisional application No. 62/547,157, filed on Aug. 18, 2017.

(51) Int. Cl.
*C07D 498/08* (2006.01)
*A61K 45/06* (2006.01)
*A61K 31/529* (2006.01)

(52) U.S. Cl.
CPC .......... *C07D 498/08* (2013.01); *A61K 31/529* (2013.01); *A61K 45/06* (2013.01); *C07B 2200/13* (2013.01)

(58) Field of Classification Search
CPC ..... A61K 31/529; A61K 45/06; C07D 498/08
USPC .......................................................... 514/257
See application file for complete search history.

(56) References Cited

U.S. PATENT DOCUMENTS

| | | | |
|---|---|---|---|
| 8,034,375 B2 | 10/2011 | Desai et al. | |
| 8,143,255 B2 | 3/2012 | Blanchard et al. | |
| 9,120,815 B2 * | 9/2015 | Mansfield | A61K 31/535 |
| 2012/0148661 A1 | 6/2012 | Phillips et al. | |
| 2013/0150378 A1 | 6/2013 | Mansfield et al. | |

FOREIGN PATENT DOCUMENTS

WO  WO 2017/165732 A1  9/2017

OTHER PUBLICATIONS

Pasha, M.K., et al., "Preclinical Metabolism and Pharmacokinetics of SB1317 (TG02), a Potent CDK/JAK2/FLT3 Inhibitor," Drug Metabolism Letters, vol. 6, No. 1; pp. 33-42, Bentham Science Publishers (2012).

Inuzuka, H. et al., "SCF$^{Fbw7}$ Regulates Cellular Apoptosis by Targeting Mcl-1 for Ubiquitination and Destruction," Nature, vol. 471, pp. 104-109, Springer Nature Publishing AG (2011).

International Search Report and Written Opinion for International Application No. PCT/US18/00264, International Search Authority, United States, dated Oct. 19, 2019.

* cited by examiner

*Primary Examiner* — Melenie L Gordon
*Assistant Examiner* — Taina D Matos Negron
(74) *Attorney, Agent, or Firm* — Sterne, Kessler, Goldstein & Fox P.L.L.C.

(57) ABSTRACT

The present disclosure provides crystalline polymorphic forms of TG02 free base and TG02 acid addition salts, pharmaceutical compositions comprising crystalline polymorphic forms of TG02 free base and TG02 acid addition salts, and methods of treating cancer and other diseases in a patient with crystalline polymorphic forms of TG02 free base and TG02 acid addition salts.

20 Claims, 11 Drawing Sheets

POLYMORPHIC FORM OF TG02

BACKGROUND OF THE INVENTION

TG02 is a pyrimidine-based multi-kinase inhibitor that inhibits CDKs 1, 2, 5, 7, and 9 together with JAK2 and FLT3. It dose-dependently inhibits signaling pathways downstream of CDKs, JAK2 and FLT3 in cancer cells with the main targets being CDKs. TG02 is anti-proliferative in a broad range of tumor cell lines, inducing GI cell cycle arrest and apoptosis. Primary cultures of progenitor cells derived from acute myeloid leukemia (AML) and polycythemia vera patients are very sensitive to TG02. Comparison with reference inhibitors that block only one of the main targets of TG02 demonstrate the benefit of combined CDK and JAK2/FLT3 inhibition in cell lines as well as primary cells. See Goh et al., *Leukemia* 26:236-43 (2012). TG02 is also known as SB1317 and by its chemical name: (16E)-14-methyl-20-oxa-5,7,14,26-tetraazatetracyclo [19.3.1.1(2,6).1(8,12)]heptacosa-1(25),2(26),3,5,8(27),9,11, 16,21,23-decaene.

U.S. Pat. No. 8,143,255 discloses TG02 as Compound 1. U.S. Pat. No. 9,120,815 discloses various salt and crystalline forms of TG02, including TG02 citrate polymorphs referred to as Citrate Pattern 1, Citrate Pattern 2, and Citrate Pattern 3. The powder x-ray diffraction (PXRD or XRPD) pattern of TG02 Citrate Pattern 1, Citrate Pattern 2, and Citrate Pattern 3 are provided in FIGS. 1 and 2.

BRIEF SUMMARY OF THE INVENTION

In one aspect, the present disclosure provides crystalline polymorphic forms of TG02 free base and TG02 acid addition salts (collectively referred to as "TG02 polymorphic forms").

In another aspect, the present disclosure provides methods of making TG02 polymorphic forms.

In another aspect, the present disclosure provides pharmaceutical compositions comprising TG02 polymorphic forms and one or more excipients.

In another aspect, the present disclosure provides methods of making pharmaceutical compositions comprising TG02 polymorphic forms and one or more excipients.

In another aspect, the present disclosure provides therapeutic methods of treating a patient having cancer, the method comprising administering to the patient a therapeutically effective amount of a TG02 polymorphic form, or a pharmaceutical composition thereof.

In another aspect, the present disclosure provides therapeutic methods of treating a patient having cancer, the method comprising administering to the patient a therapeutically effective amount of a TG02 polymorphic form, or a pharmaceutical composition thereof, and one or more additional therapeutic agents.

In another aspect, the present disclosure provides a kit comprising TG02 polymorphic forms.

DETAILED DESCRIPTION OF THE INVENTION

Polymorphic Forms of TG02 Free Base

In one embodiment, the present disclosure provides crystalline polymorphic forms of TG02 free base (FB).

In another embodiment, the present disclosure provides Form I (FB), Form II (FB), Form III (FB), Form IV (FB), or Form V (FB), or a mixture thereof.

TG02 Form I (FB)

In another embodiment, the present disclosure provides Form I (FB), characterized as having a powder x-ray diffraction (PXRD) pattern with peaks at 6.077, 17.675, 17.994, 18.475, 19.135, and 19.727 degrees 2Θ.

In another embodiment, Form I (FB) is characterized as having a PXRD pattern with peaks at 6.077, 14.628, 17.675, 17.994, 18.475, 19.135, 19.727, 19.913, 21.698, 25.456, 26.209, and 26.527 degrees 2Θ.

In another embodiment, Form I (FB) is characterized as having a PXRD pattern with peaks at 6.077, 8.840, 10.404, 13.368, 14.031, 14.628, 17.675, 17.994, 18.475, 19.135, 19.727, 19.913, 21.698, 22.460, 24.749, 25.456, 25.833, 26.209, 26.527, 26.882, 28.004, 28.625, 28.857, 29.725, 30.305, 31.009, 31.689, 32.160, 33.741, 34.293, and 35.029 degrees 2Θ.

Figure 3:
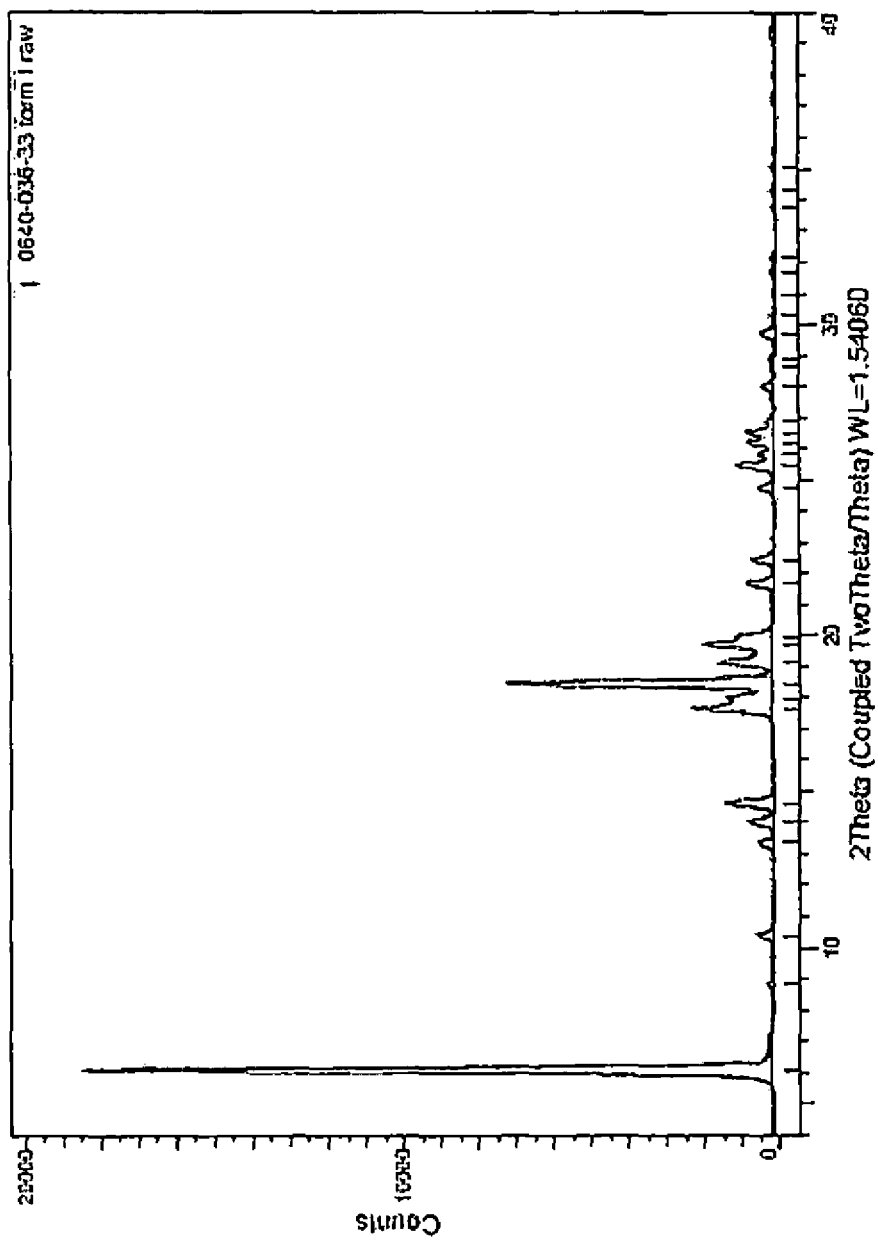
FIG. 3 is the PXRD of TG02 FB Form I.

In another embodiment, Form I (FB) is characterized as having a PXRD pattern that is essentially the same as FIG. 3.

In another embodiment, the present disclosure provides substantially pure Form I (FB), e.g., Form I (FB) characterized as comprising about 10% or less, by weight, of any other physical forms of TG02.

In another embodiment, the present disclosure provides pure TG02 Form I (FB), e.g., TG02 Form I (FB) characterized as comprising about 1% or less, by weight of any other physical forms of TG02.

TG02 Form II (FB)

In another embodiment, the present disclosure provides Form II (FB), characterized as having a PXRD pattern with peaks at 8.238, 11.607, 16.683, 17.153, and 19.073 degrees 2Θ.

In another embodiment, Form II (FB) is characterized as having a PXRD pattern with peaks at 6.954, 8.238, 11.607, 16.683, 17.153, 18.546, 19.073, 21.294, 22.342, and and 25.204 degrees 2Θ.

In another embodiment, Form II (FB) is characterized as having a PXRD pattern with peaks at 6.025, 6.954, 8.238, 10.036, 11.607, 14.563, 15.299, 16.683, 17.153, 18.064, 18.546, 19.073, 21.013, 21.294, 22.342, 23.516, 24.029, 24.518, 25.204, 26.225, 26.509, 26.954, 27.212, 27.755, 28.047, 29.133, 31.644, 32.026, 33.634, and 38.906 degrees 2Θ.

Figure 4:
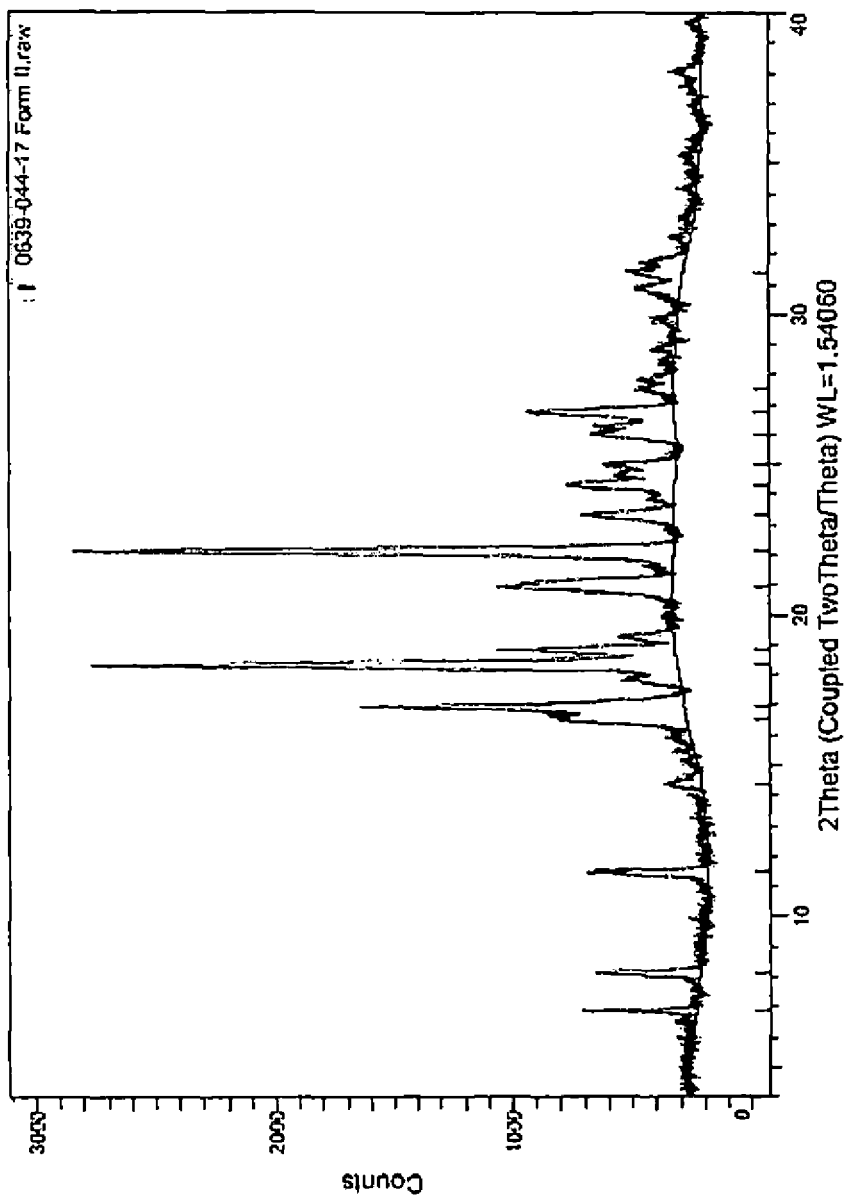
FIG. 4 is the PXRD of TG02 FB Form II.

In another embodiment, Form II (FB) is characterized as having a PXRD pattern that is essentially the same as FIG. 4.

In another embodiment, the present disclosure provides substantially pure Form II (FB).

In another embodiment, the present disclosure provides pure Form II (FB).

TG02 Form III (FB)

In another embodiment, the present disclosure provides Form III (FB), characterized as having a PXRD pattern with peaks at 6.236, 17.674, 17.769, 19.056, 19.082, 21.631, and 25.596 degrees 2Θ.

In another embodiment, Form III (FB) is characterized as having a PXRD pattern with peaks at 6.236, 15.486, 15.599, 17.674, 17.769, 18.649, 18.726, 19.056, 19.082, 19.619, 21.536, 21.594, 21.631, 24.800, and 25.596 degrees 2Θ.

In another embodiment, Form III (FB) is characterized as having a PXRD pattern with peaks at 6.236, 10.734, 12.791, 13.957, 14.987, 15.053, 15.486, 15.599, 16.650, 17.674, 17.769, 18.162, 18.649, 18.726, 19.056, 19.082, 19.676, 19.619, 21.718, 21.000, 21.536, 21.594, 21.631, 23.109, 24.800, 25.596, 26.589, 27.675, 27.857, 27.981, 29.046, and 29.288 degrees 2Θ.

Figure 5:
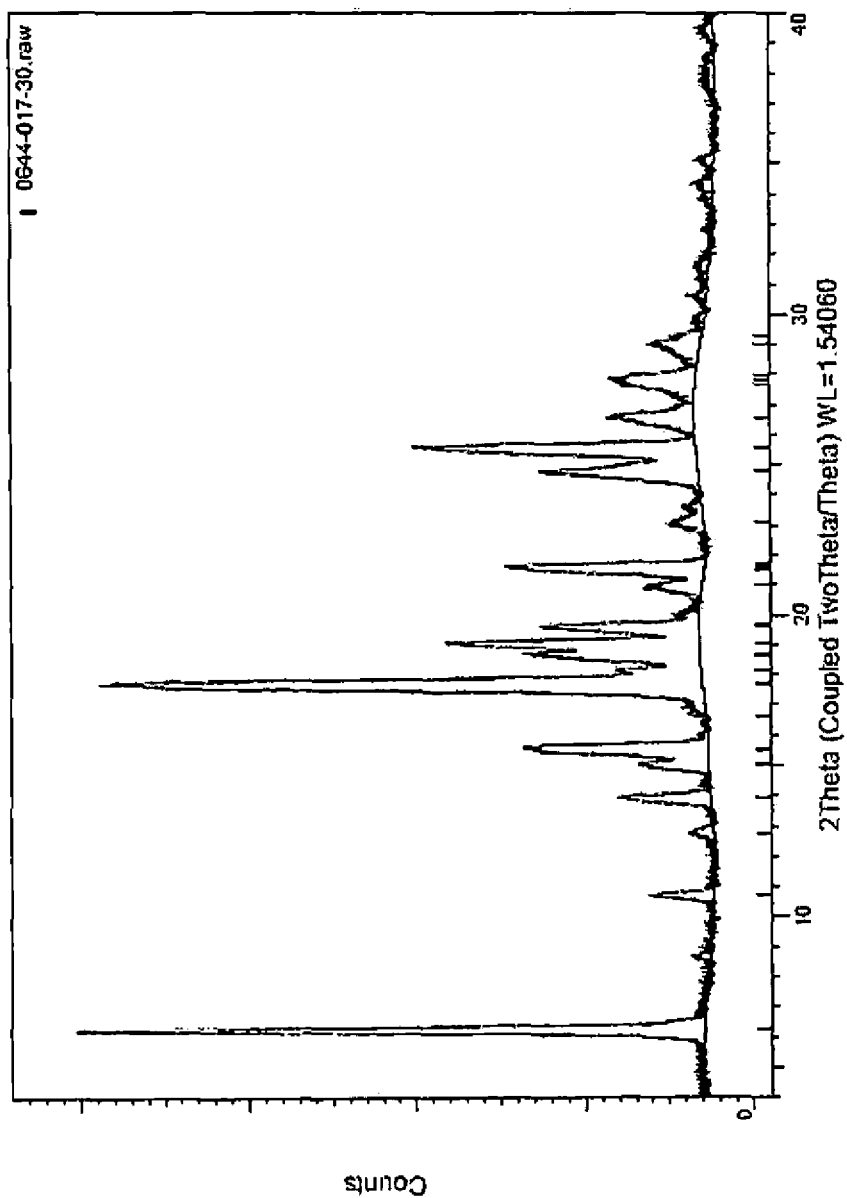
FIG. 5 is the PXRD of TG02 FB Form III.

In another embodiment, Form III (FB) is characterized as having a PXRD pattern that is essentially the same as FIG. 5.

In another embodiment, the present disclosure provides substantially pure Form III (FB).

In another embodiment, the present disclosure provides pure Form III (FB).

TG02 Form IV (FB)

In another embodiment, the present disclosure provides Form IV (FB), characterized as having a PXRD pattern with peaks at 8.484, 17.409, 18.807, 19.299, and 22.616 degrees 2Θ.

In another embodiment, Form IV (FB) is characterized as having a PXRD pattern with peaks at 7.143, 7.184, 8.484, 11.850, 17.169, 17.409, 17.573, 18.807, 19.299, 21.337, 21.519, 22.616, 24.791, and 27.180 degrees 2Θ.

In another embodiment, Form IV (FB) is characterized as having a PXRD pattern with peaks at 7.143, 7.184, 8.484, 11.850, 14.826, 15.597, 15.933, 16.957, 17.169, 17.409, 17.573, 18.311, 18.807, 19.299, 19.773, 21.337, 21.519, 22.616, 23.749, 24.791, 25.126, 25.448, 26.468, 26.729, 27.180, 27.970, 29.384, 30.310, 31.344, 31.867, and 38.475 degrees 2Θ.

Figure 6:
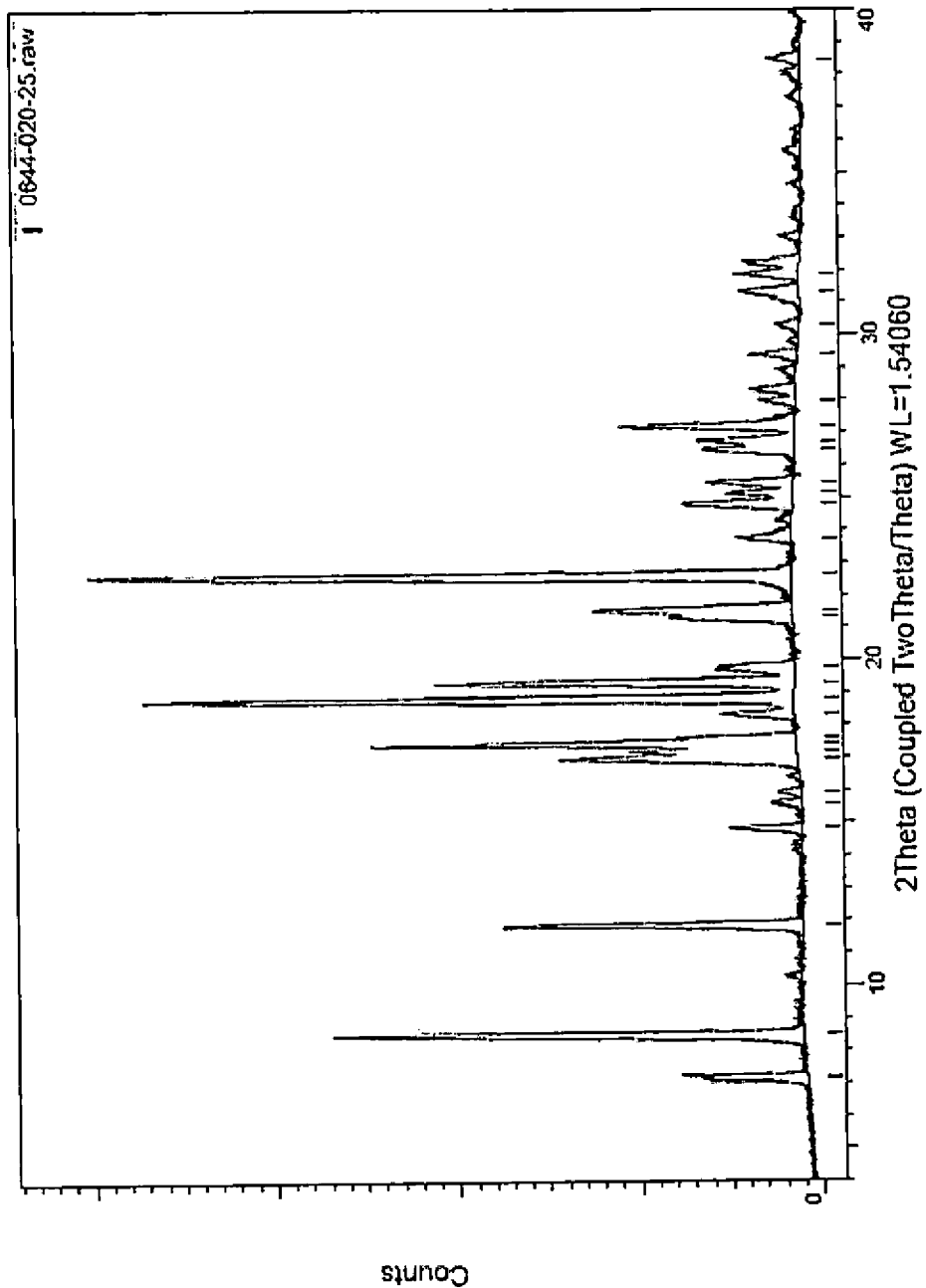
FIG. 6 is the PXRD of TG02 FB Form IV.

In another embodiment, Form IV (FB) is characterized as having a PXRD pattern that is essentially the same as FIG. 6.

In another embodiment, the present disclosure provides substantially pure Form IV (FB).

In another embodiment, the present disclosure provides pure Form IV (FB).

TG02 Form V (FB)

In another embodiment, the present disclosure provides Form V (FB), characterized as having a PXRD pattern with peaks at 7.151, 14.299, 19.114, 19.185, and 21.495 degrees 2Θ.

In another embodiment, Form V (FB) is characterized as having a PXRD pattern with peaks at 7.087, 7.151, 8.271, 8.416, 11.739, 14.299, 16.858, 17.336, 19.114, 19.185, 21.495, and 26.345 degrees 2Θ.

In another embodiment, Form V (FB) is characterized as having a PXRD pattern with peaks at 7.087, 7.151, 8.271, 8.416, 10.245, 11.657, 11.739, 14.053, 14.299, 15.478, 16.858, 17.163, 17.336, 18.751, 19.114, 19.185, 21.259, 21.495, 21.867, 22.414, 23.607, 24.185, 24.711, 25.351, 26.345, 26.558, 27.092, 27.334, 29.159, 31.202, 36.149, and 36.238 degrees 2Θ.

Figure 7:
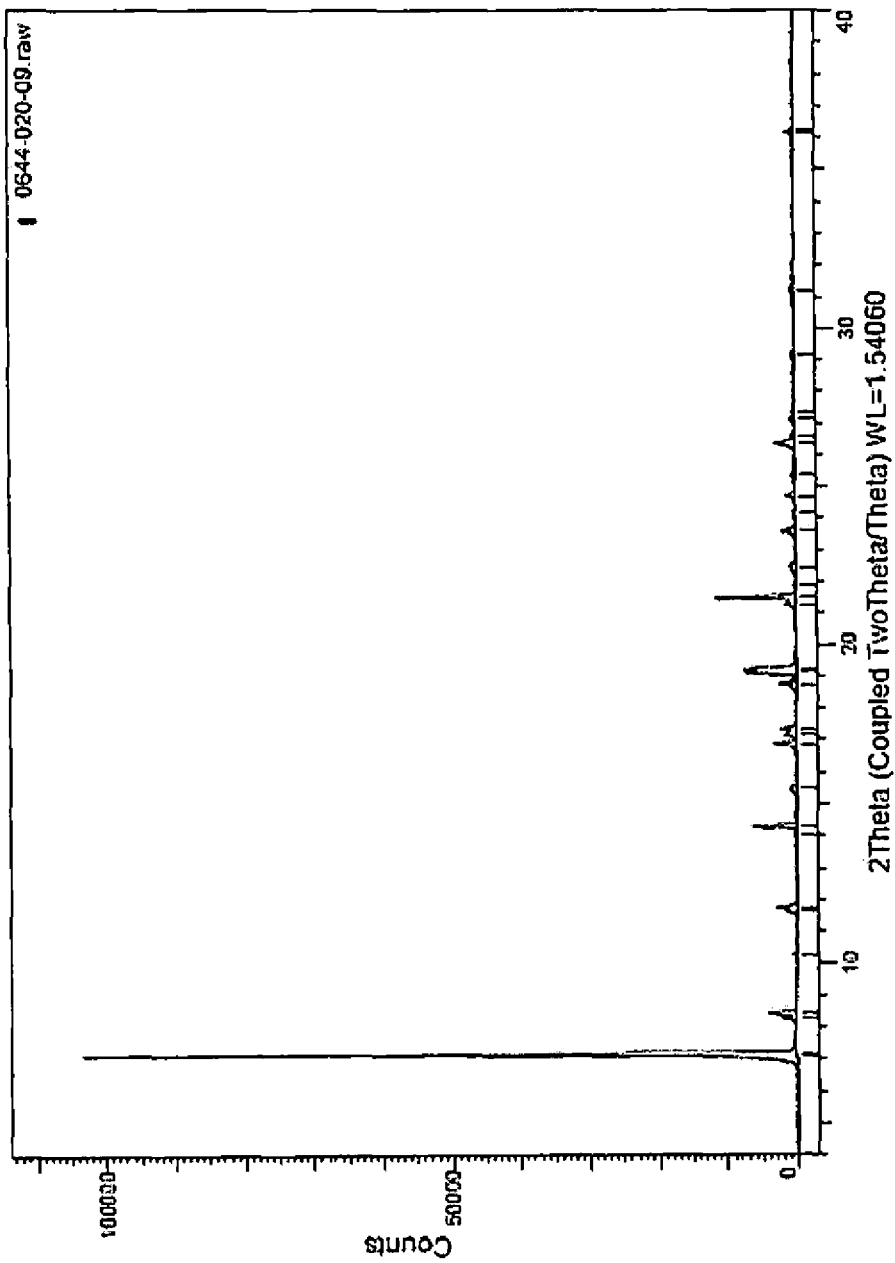
FIG. 7 is the PXRD of TG02 FB Form V.

In another embodiment, Form V (FB) is characterized as having a PXRD pattern that is essentially the same as FIG. 7.

In another embodiment, the present disclosure provides substantially pure Form V (FB).

In another embodiment, the present disclosure provides pure Form V (FB).

Polymorphic Forms of TG02 Acid Addition Salts

In another embodiment, the present disclosure provides crystalline polymorphic forms of TG02 acid addition salts.

In another embodiment, the present disclosure provides crystalline polymorphic forms of the TG02 acid addition salt with hydrochloric acid (HCl). In another embodiment, the present disclosure provides Form VI (HCl), Form VII (HCl), or Form VIII (HCl), or a mixture thereof.

TG02 Form VI (HCl)

In another embodiment, the present disclosure provides Form VI (HCl), characterized as having a PXRD pattern with peaks at 8.055, 12.695, 15.868, 16.664, 18.460, 19.392, 22.103, 24.552, and 25.604 degrees 2Θ.

In another embodiment, Form VI (HCl) is characterized as having a PXRD pattern with peaks at 8.055, 9.300, 9.527, 10.843, 12.695, 14.505, 15.868, 15.979, 16.664, 18.460, and 19.392 degrees 2Θ.

In another embodiment, Form VI (HCl) is characterized as having a PXRD pattern with peaks at 6.593, 8.055, 8.309, 9.300, 9.527, 10.843, 12.695, 12.917, 13.594, 14.505, 14.799, 15.868, 15.979, 16.289, 16.491, 16.664, 17.409, 17.845, 18.460, 19.392, 20.553, 22.103, 22.290, 22.832, 23.197, 23.565, 24.552, 24.796, 25.353, 25.604, and 26.981 degrees 2Θ.

Figure 8:
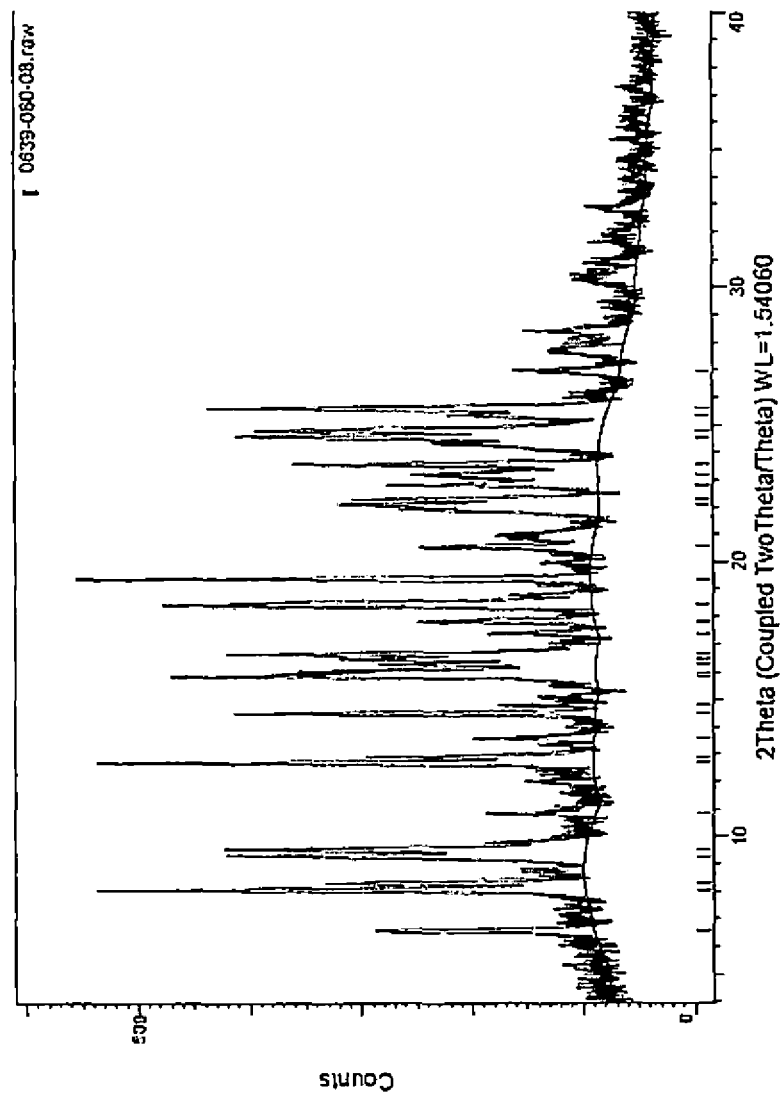
FIG. 8 is the PXRD of TG02 HCl Form VI.

In another embodiment, Form VI (HCl) is characterized as having a PXRD pattern that is essentially the same as FIG. 8.

In another embodiment, the present disclosure provides substantially pure Form VI (HCl).

In another embodiment, the present disclosure provides pure Form VI (HCl).

TG02 Form VII (HCl)

In another embodiment, the present disclosure provides Form VII (HCl), characterized as having a PXRD pattern with peaks at 6.601, 12.691, 13.364, 21.785, 23.554, and 27.007 degrees 2Θ.

In another embodiment, Form VII (HCl) is characterized as having a PXRD pattern with peaks at 6.601, 12.691, 13.364, 14.802, 16.061, 18.809, 21.785, 23.554, 24.135, 24.914, 26.904, 27.007, 27.792, and 28.179 degrees 2Θ.

In another embodiment, Form VII (HCl) is characterized as having a PXRD pattern with peaks at 6.601, 9.152, 12.691, 13.364, 13.598, 14.802, 14.952, 16.061, 17.457, 18.555, 18.809, 19.548, 20.191, 20.549, 21.259, 21.025, 21.785, 22.084, 23.554, 24.135, 24.914, 25.287, 26.904, 27.007, 27.792, 28.179, 30.091, 31.007, 31.632, and 33.498 degrees 2Θ.

Figure 9:
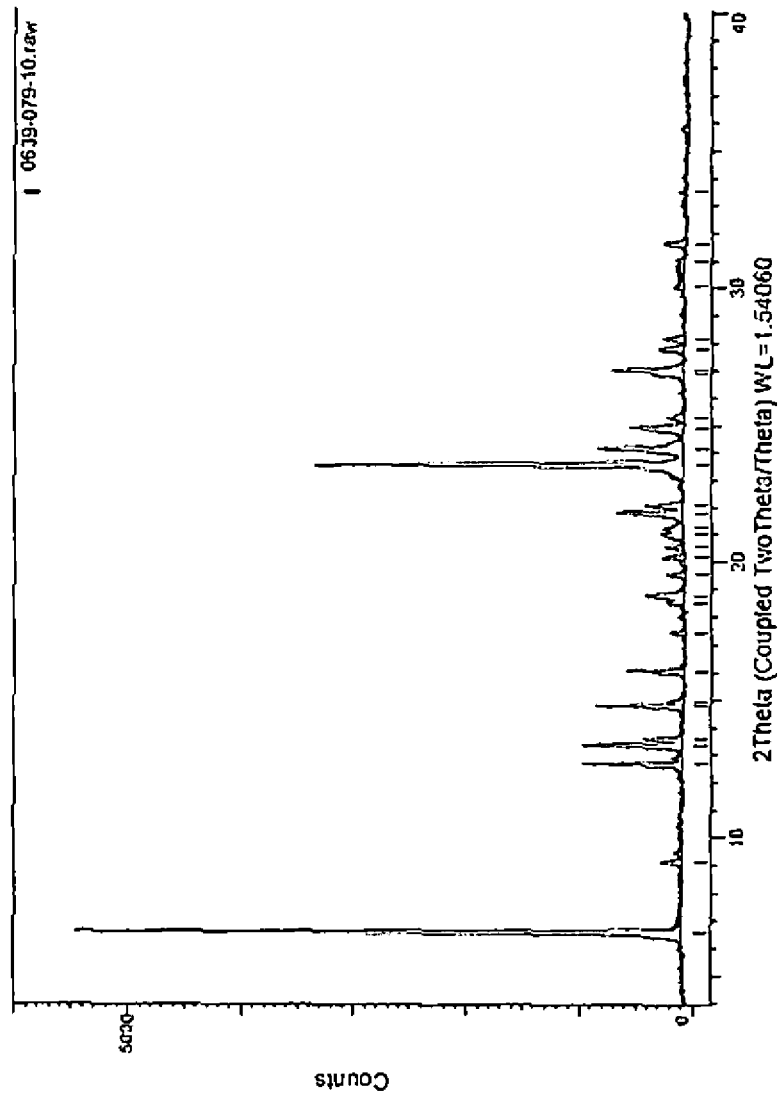
FIG. 9 is the PXRD of TG02 HCl Form VII.

In another embodiment, Form VII (HCl) is characterized as having a PXRD pattern that is essentially the same as FIG. 9.

In another embodiment, the present disclosure provides substantially pure Form VII (HCl).

In another embodiment, the present disclosure provides pure Form VII (HCl).

TG02 Form VIII (HCl)

In another embodiment, the present disclosure provides Form VIII (HCl), characterized as having a PXRD pattern with peaks at 12.994, 16.147, 22.211, 23.305, and 24.586 degrees 2Θ.

In another embodiment, Form VIII (HCl) is characterized as having a PXRD pattern with peaks at 12.994, 16.147, 17.977, 19.441, 20.933, 22.152, 22.211, 23.305, 24.586, 24.679, and 25.513 degrees 2Θ.

In another embodiment, Form VIII (HCl) is characterized as having a PXRD pattern with peaks at 8.351, 9.402, 12.994, 16.147, 16.386, 16.807, 17.977, 18.624, 19.441, 20.933, 22.152, 22.211, 23.190, 23.305, 24.305, 24.317, 24.586, 24.679, 25.407, 25.513, 27.804, and 33.775 degrees 2Θ.

Figure 10:
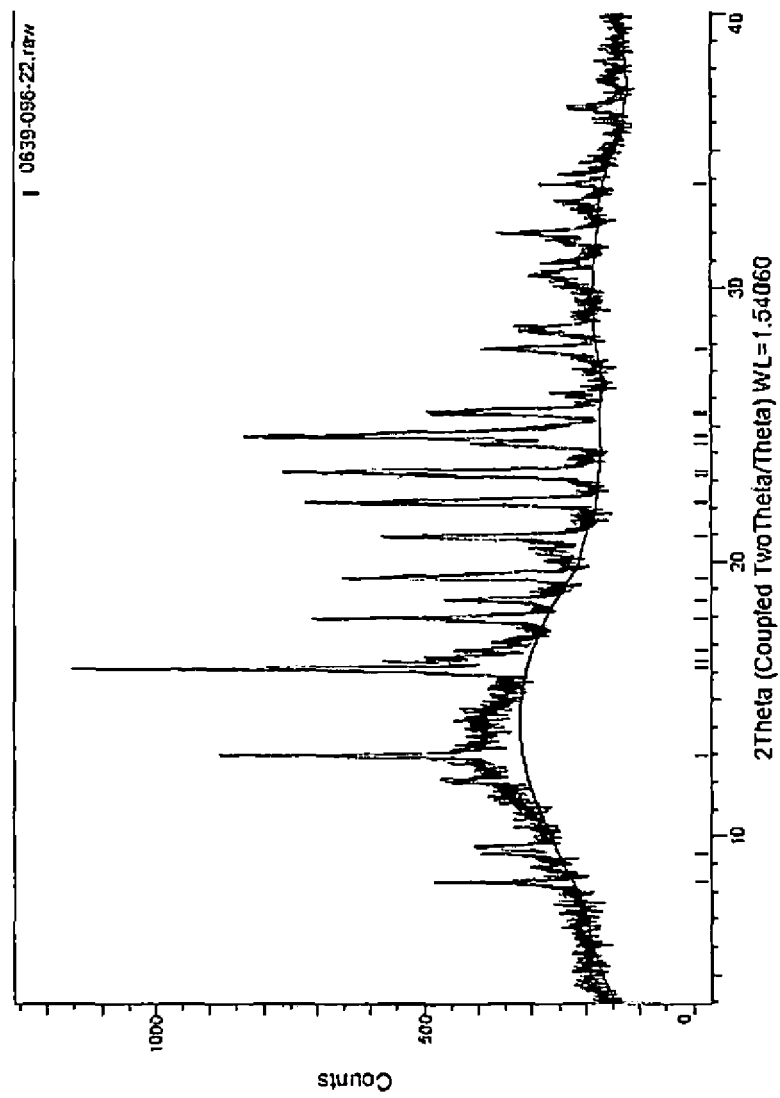
FIG. 10 is the PXRD of TG02 HCl Form VIII.

In another embodiment, Form VIII (HCl) is characterized as having a PXRD pattern that is essentially the same as FIG. 10.

In another embodiment, the present disclosure provides substantially pure Form VIII (HCl).

In another embodiment, the present disclosure provides pure Form VIII (HCl).

TG02 Form X (citrate)

In another embodiment, the present disclosure provides Form X (citrate), characterized as having a PXRD pattern with peaks at 15.2, 15.5, 21.7, 22.1, 23.0, 26.2, and 29.9 degrees 2Θ.

In another embodiment, Form X (citrate) is characterized as having a PXRD pattern with peaks at 8.6, 9.4, 11.9, 15.2, 15.5, 17.0, 17.4, 19.6, 21.7, 22.1, 23.0, 26.2, and 29.9 degrees 2Θ.

In another embodiment, Form X (citrate) is characterized as having a PXRD pattern with peaks at 8.6, 9.4, 11.9, 12.5, 14.3, 15.2, 15.5, 16.1, 16.4, 17.0, 17.4, 17.9, 19.0, 19.6, 20.3, 20.6, 21.2, 21.7, 22.1, 23.0, 23.5, 23.9, 24.2, 24.8, 26.2, 27.3, 28.0, and 29.9 degrees 2Θ.

Figure 11:
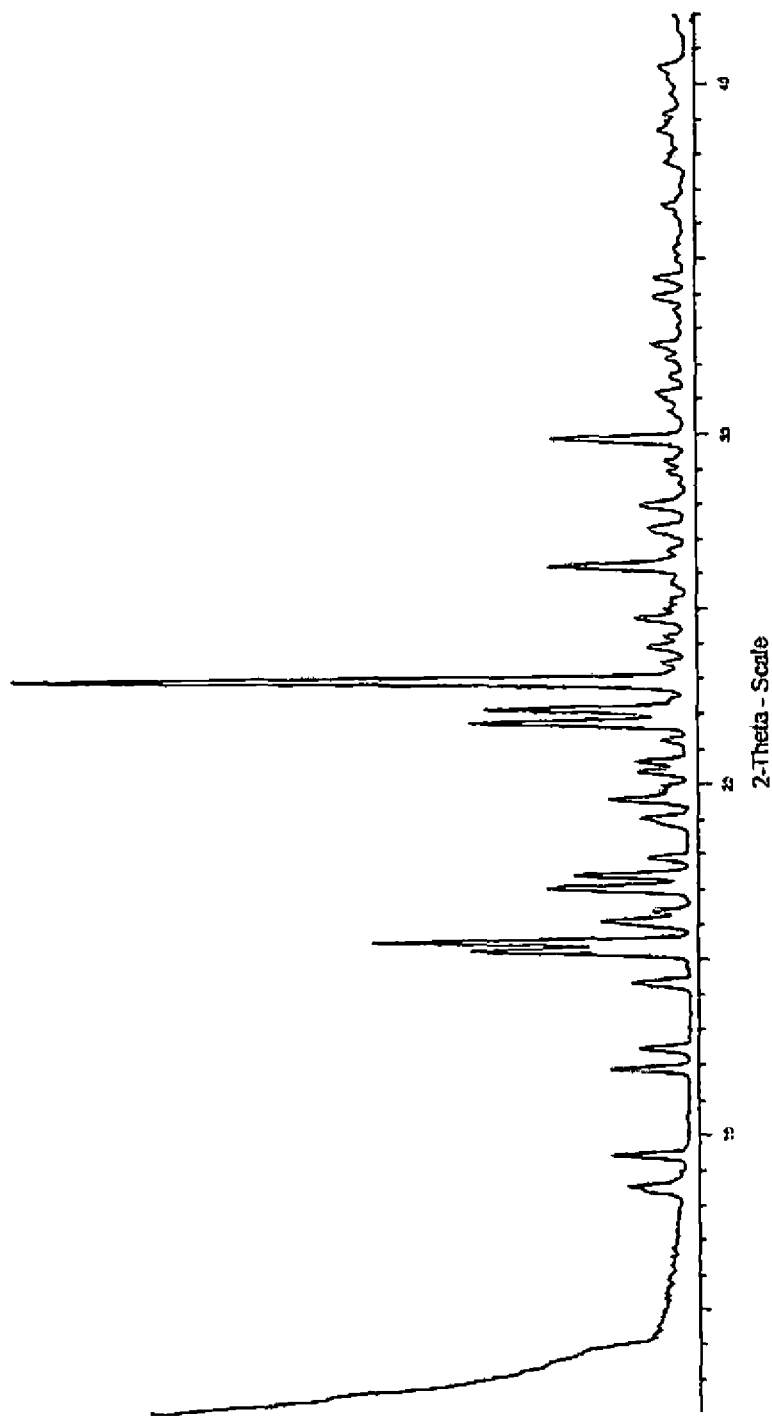
FIG. 11 is the PXRD of TG02 citrate Form X.

In another embodiment, Form X (citrate) is characterized as having a PXRD pattern that is essentially the same as FIG. 11.

In another embodiment, the present disclosure provides substantially pure Form X (citrate).

In another embodiment, the present disclosure provides pure Form X (citrate).

In another aspect, the present disclosure provides micronized TG02 polymorphic forms. In one embodiment, the average particle size distribution of the micronized TG02 polymorphic form is about 20 μm or less, e.g., about 19 μm, about 18 μm, about 17 μm, about 16 μm, about 15 μm, about 14 μm, about 13 μm, about 12 μm, or about 11 μm, or less, as determined, for example, by laser diffraction spectroscopy. In another embodiment, the average particle size distribution is about 10 μm or less, e.g., about 9 μm, about 8 μm, about 7 μm, about 6 μm, or about 5 μm, or less. In another embodiment, the average particle size distribution is about 5 μm or less, e.g., about 4 μm, about 3 μm, about 2 μm, or about 1 μm, or less. In another embodiment, the average particle size distribution is about 1 μm or less, e.g., about 0.9 μm, about 0.8 μm, about 0.7 μm, about 0.6 μm, about 0.5 μm, about 0.4 μm, about 0.3 μm, about 0.2 μm, about 0.1 μm, about 0.09 μm, about 0.08 μm, about 0.07 μm, about 0.06 μm, about 0.05 μm, about 0.04 μm, about 0.03 μm, about 0.02 μm, or about 0.01 μm or less.

In another embodiment, the present disclosure provides methods of making TG02 polymorphic forms. Methods of making TG02 polymorphic forms are described in the Examples provided herein below.

In another embodiment, the present disclosure provides TG02 polymorphic forms, or a composition thereof, for use in treating a disease, disorder, injury, or condition in a subject.

In another embodiment, the present disclosure provides TG02 polymorphic forms, or a composition thereof, for use in the manufacture of a medicament for treating a disease, disorder, injury, or condition in a subject.

In another embodiment, the present disclosure provides therapeutic methods of treating a patient having cancer, the method comprising administering to the patient a therapeutically effective amount of a TG02 polymorphic form.

In another embodiment, the present disclosure provides therapeutic methods of treating a patient having cancer, the method comprising administering to the patient a therapeutically effective amount of a TG02 polymorphic form, wherein one or more of the genes listed in Table 1, see below, is differentially present in a biological sample taken from the patient as compared with a biological sample taken from a subject of another phenotypic status. In another embodiment, MYC overexpression is differentially present in a sample taken from the patient. In another embodiment, MCL1 overexpression is differentially present in a sample taken from the patient.

In another embodiment, the present disclosure provides therapeutic methods of treating a patient having cancer, the method comprising administering to the patient a therapeutically effective amounts of a TG02 polymorphic form and a second therapeutic agent, e.g., an immune checkpoint inhibitor, wherein one or more of the genes listed in Table 1, see below, is differentially present in a biological sample taken from the patient as compared with a biological sample taken from a subject of another phenotypic status. In another embodiment, MYC overexpression is differentially present in a sample taken from the patient. In another embodiment, MCL1 overexpression is differentially present in a sample taken from the patient. In another embodiment, the TG02 polymorphic form is administered to the patient before the second therapeutic agent. In another embodiment, the TG02 polymorphic form is administered to the patient after the second therapeutic agent. In another embodiment, the TG02 polymorphic form is administered to the patient at the same time as the second therapeutic agent.

In another embodiment, the present disclosure provides therapeutic methods of treating a patient having cancer, the method comprising administering to the patient therapeutically effective amounts of a TG02 polymorphic form and a second therapeutic agent, e.g., an immune checkpoint inhibitor. In another embodiment, the TG02 polymorphic form is administered to the patient before the second therapeutic agent. In another embodiment, the TG02 polymorphic form is administered to the patient after the second therapeutic agent. In another embodiment, the TG02 polymorphic form is administered to the patient at the same time as an immune checkpoint inhibitor.

In another embodiment, the present disclosure provides kits comprising a TG02 polymorphic form and a second therapeutic agent, e.g., an immune checkpoint inhibitor, and instructions for administering the TG02 polymorphic form and the second therapeutic agent to a patient having cancer.

In another embodiment, the kit is packaged in a manner that facilitates its use to practice methods of the present disclosure.

In another embodiment, the kit includes a TG02 polymorphic form (or a composition comprising the TG02 polymorphic form) packaged in a container, such as a sealed bottle or vessel, with a label affixed to the container or included in the kit that describes use of the TG02 polymorphic form or composition to practice the method of the disclosure. In one embodiment, the TG02 polymorphic form is packaged in a unit dosage form. The kit further can include a device suitable for administering the composition according to the intended route of administration.

The disclosure provides various therapeutic methods, kits, and compositions for treating cancer in a patient in need thereof with a TG02 polymorphic form. In one embodiment, the cancer is a solid tumor. In another embodiment, the cancer is a hematological malignancy. In another embodiment, the cancer selected from any one or more of the cancers of Table 2.

TABLE 2

| | | | |
|---|---|---|---|
| adrenal cancer | acinic cell carcinoma | acoustic neuroma | acral lentigious melanoma |
| acrospiroma | acute eosinophilic leukemia | acute erythroid leukemia | acute lymphoblastic leukemia |
| acute megakaryoblastic leukemia | acute monocytic leukemia | acute promyelocytic leukemia | adenocarcinoma |
| adenoid cystic carcinoma | adenoma | adenomatoid odontogenic tumor | adenosquamous carcinoma |
| adipose tissue neoplasm | adrenocortical carcinoma | adult T-cell leukemia/lymphoma | aggressive NK-cell leukemia |
| AIDS-related lymphoma | alveolar rhabdomyosarcoma | alveolar soft part sarcoma | ameloblastic fibroma |
| anaplastic large cell lymphoma | anaplastic thyroid cancer | angioimmunoblastic T-cell lymphoma | angiomyolipoma |
| angiosarcoma | astrocytoma | atypical teratoid rhabdoid tumor | B-cell chronic lymphocytic leukemia |
| B-cell prolymphocytic leukemia | B-cell lymphoma | basal cell carcinoma | biliary tract cancer |
| bladder cancer | blastoma | bone cancer | Brenner tumor |
| Brown tumor | Burkitt's lymphoma | breast cancer | brain cancer |
| carcinoma | carcinoma in situ | carcinosarcoma | cartilage tumor |
| cementoma | myeloid sarcoma | chondroma | chordoma |
| choriocarcinoma | choroid plexus papilloma | clear-cell sarcoma of the kidney | craniopharyngioma |
| cutaneous T-cell lymphoma | cervical cancer | colorectal cancer | Degos disease |
| desmoplastic small round cell tumor | diffuse large B-cell lymphoma | dysembryoplastic neuroepithelial tumor | dysgerminoma |
| embryonal carcinoma | endocrine gland neoplasm | endodermal sinus tumor | enteropathy-associated T-cell lymphoma |
| esophageal cancer | fetus in fetu | fibroma | fibrosarcoma |
| follicular lymphoma | follicular thyroid cancer | ganglioneuroma | gastrointestinal cancer |
| germ cell tumor | gestational choriocarcinoma | giant cell fibroblastoma | giant cell tumor of the bone |
| glial tumor | glioblastoma | glioma | gliomatosis cerebri |
| glucagonoma | gonadoblastoma | granulosa cell tumor | gynandroblastoma |
| gallbladder cancer | gastric cancer | hairy cell leukemia | hemangioblastoma |
| head and neck cancer | hemangiopericytoma | hematological malignancy | hepatoblastoma |
| hepatocellular carcinoma | hepatosplenic T-cell lymphoma | Hodgkin's lymphoma | non-Hodgkin's lymphoma |
| invasive lobular carcinoma | intestinal cancer | kidney cancer | laryngeal cancer |
| lentigo maligna | lethal midline carcinoma | leukemia | leydig cell tumor |
| liposarcoma | lung cancer | lymphangioma | lymphangiosarcoma |
| lymphoepithelioma | lymphoma | acute lymphocytic leukemia | acute myelogeous leukemia |
| chronic lymphocytic leukemia | liver cancer | small cell lung cancer | non-small cell lung cancer |
| MALT lymphoma | malignant fibrous histiocytoma | malignant peripheral nerve sheath tumor | malignant triton tumor |
| mantle cell lymphoma | marginal zone B-cell lymphoma | mast cell leukemia | mediastinal germ cell tumor |
| medullary carcinoma of the breast | medullary thyroid cancer | medulloblastoma | melanoma |
| meningioma | merkel cell cancer | mesothelioma | metastatic urothelial carcinoma |
| mixed Mullerian tumor | mucinous tumor | multiple myeloma | muscle tissue neoplasm |
| mycosis fungoides | myxoid liposarcoma | myxoma | myxosarcoma |
| nasopharyngeal carcinoma | neurinoma | neuroblastoma | neurofibroma |
| neuroma | nodular melanoma | ocular cancer | oligoastrocytoma |
| oligodendroglioma | oncocytoma | optic nerve sheath meningioma | optic nerve tumor |
| oral cancer | osteosarcoma | ovarian cancer | Pancoast tumor |
| papillary thyroid cancer | paraganglioma | pinealoblastoma | pineocytoma |
| pituicytoma | pituitary adenoma | pituitary tumor | plasmacytoma |
| polyembryoma | precursor T-lymphoblastic lymphoma | primary central nervous system lymphoma | primary effusion lymphoma |
| preimary peritoneal cancer | prostate cancer | pancreatic cancer | pharyngeal cancer |
| pseudomyxoma periotonei | renal cell carcinoma | renal medullary carcinoma | retinoblastoma |

TABLE 2-continued

| | | | |
|---|---|---|---|
| rhabdomyoma | rhabdomyosarcoma | Richter's transformation | rectal cancer |
| sarcoma | Schwannomatosis | seminoma | Sertoli cell tumor |
| sex cord-gonadal stromal tumor | signet ring cell carcinoma | skin cancer | small blue round cell tumors |
| small cell carcinoma | soft tissue sarcoma | somatostatinoma | soot wart |
| spinal tumor | splenic marginal zone lymphoma | squamous cell carcinoma | synovial sarcoma |
| Sezary's disease | small intestine cancer | squamous carcinoma | stomach cancer |
| T-cell lymphoma | testicular cancer | thecoma | thyroid cancer |
| transitional cell carcinoma | throat cancer | urachal cancer | urogenital cancer |
| urothelial carcinoma | uveal melanoma | uterine cancer | verrucous carcinoma |
| visual pathway glioma | vulvar cancer | vaginal cancer | Waldenstrom's macroglobulinemia |
| Warthin's tumor | Wilms' tumor | diffuse pontine glioma | |

In another embodiment, the cancer is selected from the group consisting of squamous cell carcinoma of the head and neck, adenocarcinoma squamous cell carcinoma of the esophagus, adenocarcinoma of the stomach, adenocarcinoma of the colon, hepatocellular carcinoma, cholangiocarcinoma of the biliary system, adenocarcinoma of gall bladder, adenocarcinoma of the pancreas, ductal carcinoma in situ of the breast, adenocarcinoma of the breast, adenocarcinoma of the lungs, squamous cell carcinoma of the lungs, transitional cell carcinoma of the bladder, squamous cell carcinoma of the bladder, squamous cell carcinoma of the cervix, adenocarcinoma of the cervix, endometrial carcinoma, penile squamous cell carcinoma, and squamous cell carcinoma of the skin.

In another embodiment, the cancer is selected from the group consisting of multiple myeloma, hepatocellular carcinoma, glioblastoma, lung cancer, breast cancer, head and neck cancer, prostate cancer, melanoma, colorectal cancer, and diffuse pontine glioma.

In another embodiment, the cancer is diffuse pontine glioma.

In another embodiment, a precancerous tumor is selected from the group consisting of leukoplakia of the head and neck, Barrett's esophagus, metaplasia of the stomach, adenoma of the colon, chronic hepatitis, bile duct hyperplasia, pancreatic intraepithelial neoplasia, atypical adenomatous hyperplasia of the lungs, dysplasia of the bladder, cervical intraepithelial neoplasia, penile intraepithelial neoplasia, and actinic keratosis of the skin.

In another embodiment, the patient has tumors that overexpress MYC, MCL1, or both. The tumors may be determined to overexpress MYC, MCL1, or both, by methods known in the art.

In another embodiment, the cancer is selected from the group consisting of hepatocellular carcinoma, glioblastoma, lung cancer, breast cancer, head and neck cancer, prostate cancer, melanoma, and colorectal cancer.

In another embodiment, the cancer has become resistant to conventional cancer treatments. The term "conventional cancer treatments" as used herein refers to any cancer drugs or biologics or radiation therapy, or combination of cancer drugs and/or biologics and/or radiation therapy that have been tested and/or approved for therapeutic use in humans by the U.S. Food and Drug Administration, European Medicines Agency, or similar regulatory agency.

In another embodiment, the patient has been treated previously with an immune checkpoint inhibitor without TG02. For example, the previous immune checkpoint therapy may be an anti-PD-1 therapy.

In another embodiment, the present disclosure provides therapeutic methods of treating a patient having cancer, the method comprising administering to the patient a therapeutically effective amount of a TG02 polymorphic form, wherein the phenotypic status of the patient is overexpression of MYC, overexpression of MCL1, or overexpression of MYC and MCL1. In another embodiment, the cancer is selected from the group consisting of hepatocellular carcinoma, glioblastoma, lung cancer, breast cancer, head and neck cancer, prostate cancer, melanoma, and colorectal cancer.

In another embodiment, the present disclosure provides therapeutic methods of treating a patient having cancer, the method comprising administering to the patient therapeutically effective amounts of a TG02 polymorphic form and a second therapeutic agent.

In one embodiment, the second therapeutic agent is selected from the group consisting of temozolomide, daunorubicin, doxorubicin, epirubicin, idarubicin, valrubicin, cisplatin, bortezomib, carfilzomib, lenalidomide, sorafenib, regorafenib, and radiotherapy.

In another embodiment, the second therapeutic agent is an immune checkpoint inhibitor. In another embodiment, the immune checkpoint inhibitor is a PD-1 inhibitor or a PD-L1 inhibitor. In another embodiment, the PD-1 inhibitor is an anti-PD-1 antibody. In another embodiment, the anti-PD-1 antibody is selected from the group consisting of nivolumab, pembrolizumab, pidilizumab and STI-1110. In another embodiment, the PD-L1 inhibitor is an anti-PD-L1 antibody. In another embodiment, the anti-PD-L1 antibody is selected from the group consisting of avelumab, atezolizumab, durvalumab, and STI-1014

In another embodiment, the present disclosure provides therapeutic methods of treating a patient having cancer, comprising administering to the patient therapeutically effective amounts of a TG02 polymorphic form, an immune checkpoint inhibitor, and a third therapeutic agent.

In another embodiment, the present disclosure provides personalized medicine for cancer patients, and encompasses the selection of treatment options with the highest likelihood of successful outcome for individual cancer patients. In another aspect, the disclosure relates to the use of an assay(s) to predict the treatment outcome, e.g., the likelihood of favorable responses or treatment success, in patients having cancer.

In another embodiment, the present disclosure provides methods of selecting a patient, e.g., a human subject for treatment of cancer with a TG02 polymorphic form and, optionally, a second therapeutic agent, e.g., an immune checkpoint inhibitor, comprising obtaining a biological sample, e.g., blood cells, from the patient, testing a biological sample from the patient for the presence of a biomarker, e.g., overexpression of MYC, overexpression of MCL1, or both, and selecting the patient for treatment if the biological sample contains that biomarker. In another embodiment, the methods further comprise administering a therapeutically effective amount of a TG02 polymorphic form and, optionally, an immune checkpoint inhibitor, to the patient if the biological sample contains the biomarker. Examples of cancer biomarkers are provided in Table 1. In another embodiment, the cancer is a solid tumor. In another embodiment, the cancer is a hematological malignancy. In another embodiment, the cancer is selected from the group consisting of hepatocellular carcinoma, glioblastoma, lung cancer, breast cancer, head and neck cancer, prostate cancer, melanoma, and colorectal cancer.

In another embodiment, the present disclosure provides methods of predicting treatment outcomes in a patient having cancer, comprising obtaining a biological sample, from the patient, testing the biological sample from the patient for the presence of a biomarker, e.g., overexpression of MYC, overexpression of MCL1, or both, wherein the detection of the biomarker indicates the patient will respond favorably to administration of a therapeutically effective amount of a TG02 polymorphic form and, optionally, a second therapeutic agent. Favorable responses include, but are not limited to, a decrease in tumor size and an increase in progression-free or overall survival.

In another embodiment, the present disclosure provides methods of treating cancer, comprising administering a therapeutically effective amount of a TG02 polymorphic form and, optionally, a second therapeutic agent, e.g., an immune checkpoint inhibitor to a patient, e.g., a human subject, with cancer in whom the patient's cells contain a biomarker. In another embodiment, the patient is selected for treatment with a TG02 polymorphic form and, optionally, an immune checkpoint inhibitor, after the patient's cells have been determined to contain an overexpression of MYC. In another embodiment, the patient is selected for treatment with a TG02 polymorphic form and, optionally, an immune checkpoint inhibitor after the patient's cells have been determined to contain an overexpression of MCL1. In another embodiment, the patient is selected for treatment with a TG02 polymorphic form and, optionally, an immune checkpoint inhibitor after the patient's cells have been determined to contain an overexpression of MYC and an overexpression of MCL1.

In another embodiment, the method of treating a patient having cancer comprises obtaining a biological sample from the patient, determining whether the biological sample contains a biomarker, e.g., overexpression of MYC, overexpression of MCL1, or both, and administering to the patient a therapeutically effective amount of a TG02 polymorphic form and, optionally, an immune checkpoint inhibitor if the biological sample contains the biomarker. In another embodiment, the methods provided herein comprise determining whether the patient's cells contain an overexpression of MYC. In another embodiment, the methods provided herein comprise determining whether the patient's cells contain an overexpression of MCL1. In another embodiment, the methods provided herein comprise determining whether the patient's cells contain an overexpression of MYC and MCL1.

In another embodiment, the disclosure provides a method of treating a subject having cancer, the method comprising obtaining a biological sample from the subject, determining the expression level of MYC, MCL1, or both in the biological sample; and administering a therapeutically effective amount of a TG02 polymorphic form and a second therapeutic agent, e.g., temozolomide, carfilzomib, sorafenib, regorafenib, bortezomib, doxorubicin, cisplatin, lenalidomide, dexamethasone, or Ara-C, to the subject if the biological sample shows overexpression of MYC, MCL1, or both.

I. Optional Therapeutic Agents

In some therapeutic methods of the disclosure, a second therapeutic agent is administered to a cancer patient in combination with a TG02 polymorphic form.

In some therapeutic methods of the disclosure, a second therapeutic agent and a third therapeutic agent are administered to a cancer patient in combination with a TG02 polymorphic form.

In some therapeutic methods of the disclosure, a second therapeutic agent, a third therapeutic agent, and a fourth therapeutic agent are administered to a cancer patient in combination with a TG02 polymorphic form.

The second, third, and fourth therapeutic agents used in the therapeutic methods of the present disclosure are referred to as "optional therapeutic agents." Such optional therapeutic agents useful in the treatment of cancer patients are known in the art. In one embodiment, the optional therapeutic agent combined with a TG02 polymorphic form is an anticancer agent. Optional therapeutic agents include, but are not limited to, temozolomide, daunorubicin, doxorubicin, epirubicin, idarubicin, valrubicin, cisplatin, bortezomib, carfilzomib, lenalidomide, sorafenib, regorafenib, radiotherapy, immune checkpoint inhibitors, e.g., PD-1 or PD-L1 inhibitors, e.g., anti-PD-1 or anti-PD-L1 antibodies, e.g., nivolumab, pembrolizumab, pidilizumab, STI-1110, avelumab, atezolizumab, durvalumab, and STI-1014.

Optional therapeutic agents are administered in an amount to provide their desired therapeutic effect. The effective dosage range for each optional therapeutic agent is known in the art, and the optional therapeutic agent is administered to an individual in need thereof within such established ranges.

A TG02 polymorphic form and the optional therapeutic agent can be administered together as a single-unit dose or separately as multi-unit doses, and in any order, e.g., wherein a TG02 polymorphic form is administered before the optional therapeutic agent, or vice versa. One or more doses of a TG02 polymorphic form and the optional therapeutic agent can be administered to the patient.

Immune checkpoint inhibitors are therapies that blockade immune system inhibitor checkpoints. In some therapeutic methods of the disclosure, an immune checkpoint inhibitor is administered to a cancer patient in combination with a TG02 polymorphic form.

Immune checkpoints can be stimulatory or inhibitory. Blockade of inhibitory immune checkpoint activates immune system function and can be used for cancer immunotherapy. Pardoll, *Nature Reviews. Cancer* 12:252-64 (2012). Tumor cells turn off activated T cells when they attach to specific T-cell receptors. Immune checkpoint inhibitors prevent tumor cells from attaching to T cells, which results in T cells remaining activated. In effect, the coordinated action by cellular and soluble components combats pathogens and injuries by cancers. The modulation of immune system pathways may involve changing the expression or the functional activity of at least one component of the pathway to then modulate the response by the immune system. U.S. 2015/0250853. Examples of immune checkpoint inhibitors include PD-1 inhibitors, PD-L1 inhibitors, CTLA-4 inhibitors, LAG3 inhibitors, TIM3 inhibitors, cd47 inhibitors, and B7-H1 inhibitors. Thus, in one embodiment, the immune checkpoint inhibitor is selected from the group consisting of a PD-1 inhibitor, a PD-L1 inhibitor, a CTLA-4 inhibitor, a LAG3 inhibitor, a TIM3 inhibitor, and a cd47 inhibitor.

In another embodiment, the immune checkpoint inhibitor is a programmed cell death (PD-1) inhibitor. PD-1 is a T-cell coinhibitory receptor that plays a pivotal role in the ability of tumor cells to evade the host's immune system. Blockage of interactions between PD-1 and PD-L1, a ligand of PD-1, enhances immune function and mediates antitumor activity. Examples of PD-1 inhibitors include antibodies that specifically bind to PD-1. Particular anti-PD-1 antibodies include, but are not limited to nivolumab, pembrolizumab, STI-1014, and pidilzumab. For a general discussion of the availability, methods of production, mechanism of action, and clinical studies of anti-PD-1 antibodies, see U.S. 2013/0309250, U.S. Pat. Nos. 6,808,710, 7,595,048, 8,008,449, 8,728,474, 8,779,105, 8,952,136, 8,900,587, 9,073,994, 9,084,776, and Naido et al., *British Journal of Cancer* 111:2214-19 (2014).

In another embodiment, the immune checkpoint inhibitor is a PD-L1 (also known as B7-H1 or CD274) inhibitor. Examples of PD-L1 inhibitors include antibodies that specifically bind to PD-L1. Particular anti-PD-L antibodies include, but are not limited to, avelumab, atezolizumab, durvalumab, and BMS-936559. For a general discussion of the availability, methods of production, mechanism of action, and clinical studies, see U.S. Pat. No. 8,217,149, U.S. 2014/0341917, U.S. 2013/0071403, WO 2015036499, and Naido et al., *British Journal of Cancer* 111:2214-19 (2014).

In another embodiment, the immune checkpoint inhibitor is a CTLA-4 inhibitor. CTLA-4, also known as cytotoxic T-lymphocyte antigen 4, is a protein receptor that downregulates the immune system. CTLA-4 is characterized as a "brake" that binds costimulatory molecules on antigen-presenting cells, which prevents interaction with CD28 on T cells and also generates an overtly inhibitory signal that constrains T cell activation. Examples of CTLA-4 inhibitors include antibodies that specifically bind to CTLA-4. Particular anti-CTLA-4 antibodies include, but are not limited to, ipilimumab and tremelimumab. For a general discussion of the availability, methods of production, mechanism of action, and clinical studies, see U.S. Pat. Nos. 6,984,720, 6,207,156, and Naido et al., *British Journal of Cancer* 111:2214-19 (2014).

In another embodiment, the immune checkpoint inhibitor is a LAG3 inhibitor. LAG3, Lymphocyte Activation Gene 3, is a negative co-stimulatory receptor that modulates T cell homeostatis, proliferation, and activation. In addition, LAG3 has been reported to participate in regulatory T cells (Tregs) suppressive function. A large proportion of LAG3 molecules are retained in the cell close to the microtubule-organizing center, and only induced following antigen specific T cell activation. U.S. 2014/0286935. Examples of LAG3 inhibitors include antibodies that specifically bind to LAG3. Particular anti-LAG3 antibodies include, but are not limited to, GSK2831781. For a general discussion of the availability, methods of production, mechanism of action, and studies, see, U.S. 2011/0150892, U.S. 2014/0093511, U.S. 20150259420, and Huang et al., *Immunity* 21:503-13 (2004).

In another embodiment, the immune checkpoint inhibitor is a TIM3 inhibitor. TIM3, T-cell immunoglobulin and mucin domain 3, is an immune checkpoint receptor that functions to limit the duration and magnitude of $T_H1$ and $T_C1$ T-cell responses. The TIM3 pathway is considered a target for anticancer immunotherapy due to its expression on dysfunctional $CD8^+$ T cells and Tregs, which are two reported immune cell populations that constitute immunosuppression in tumor tissue. Anderson, *Cancer Immunology Research* 2:393-98 (2014). Examples of TIM3 inhibitors include antibodies that specifically bind to TIM3. For a general discussion of the availability, methods of production, mechanism of action, and studies of TIM3 inhibitors, see U.S. 20150225457, U.S. 20130022623, U.S. Pat. No. 8,522,156, Ngiow et al., *Cancer Res* 71: 6567-71 (2011), Ngiow, et al., *Cancer Res* 71:3540-51 (2011), and *Anderson, Cancer Immunology Res* 2:393-98 (2014).

In another embodiment, the immune checkpoint inhibitor is a cd47 inhibitor. See Unanue, E. R., *PNAS* 110:10886-87 (2013).

The term "antibody" is meant to include intact monoclonal antibodies, polyclonal antibodies, multispecific antibodies formed from at least two intact antibodies, and antibody fragments, so long as they exhibit the desired biological activity. In another embodiment, "antibody" is meant to include soluble receptors that do not possess the Fc portion of the antibody. In one embodiment, the antibodies are humanized monoclonal antibodies and fragments thereof made by means of recombinant genetic engineering.

Another class of immune checkpoint inhibitors include polypeptides that bind to and block PD-1 receptors on T-cells without triggering inhibitor signal transduction. Such peptides include B7-DC polypeptides, B7-H1 polypeptides, B7-1 polypeptides and B7-2 polypeptides, and soluble fragments thereof, as disclosed in U.S. Pat. No. 8,114,845.

Another class of immune checkpoint inhibitors include compounds with peptide moieties that inhibit PD-1 signaling. Examples of such compounds are disclosed in U.S. Pat. No. 8,907,053 and have the structure:

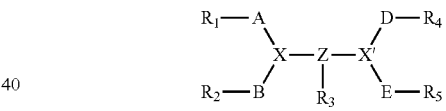

or a pharmaceutically acceptable salt thereof, wherein the compound comprises at least 5 amino acids useful as therapeutic agents capable of inhibiting the PD-1 signaling pathway.

Another class of immune checkpoint inhibitors include inhibitors of certain metabolic enzymes, such as indoleamine 2,3 dioxygenase (IDO), which is expressed by infiltrating myeloid cells and tumor cells. The IDO enzyme inhibits immune responses by depleting amino acids that are necessary for anabolic functions in T cells or through the synthesis of particular natural ligands for cytosolic receptors that are able to alter lymphocyte functions. Pardoll, *Nature Reviews. Cancer* 12:252-64 (2012); Löb, *Cancer Immunol Immunother* 58:153-57 (2009). Particular IDO blocking agents include, but are not limited to levo-1-methyl typtophan (L-1MT) and 1-methyl-tryptophan (1MT). Qian et al., *Cancer Res* 69:5498-504 (2009); and Löb et al., *Cancer Immunol Immunother* 58:153-7 (2009).

In another embodiment, the immune checkpoint inhibitor is nivolumab, pembrolizumab, pidilizumab, STI-1110, avelumab, atezolizumab, durvalumab, STI-1014, ipilimumab, tremelimumab, GSK2831781, BMS-936559 or MED14736.

In another embodiment, the optional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, the optional therapeutic agent is a chemotherapeutic agent or other anti-proliferative agent that can be administered in combination with a TG02 polymorphic form to treat cancer. Examples of therapies and anticancer agents that can be used in combination with a TG02 polymorphic form include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Nonlimiting exemplary antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent, e.g., temozolomide; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include steroids, such as atamestane, exemestane, and formestane, and non-steroids, such as aminoglutethimide, roglethimide, pyridoglutethimide, trilostane, testolactone, ketokonazole, vorozole, fadrozole, anastrozole, and letrozole.

Nonlimiting anti-estrogens include tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Nonlimiting exemplary topoisomerase I inhibitors include topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Nonlimiting exemplary alkylating agents include cyclophosphamide, ifosfamide, melphalan, and nitrosoureas, such as carmustine and lomustine.

Nonlimiting exemplary matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Nonlimiting exemplary mTOR inhibitors include compounds that inhibit the mammalian target of rapamycin (mTOR) and possess antiproliferative activity such as sirolimus, everolimus, CCI-779, and ABT578.

Nonlimiting exemplary antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Nonlimiting exemplary platin compounds include carboplatin, cis-platin, cisplatinum, and oxaliplatin.

Nonlimiting exemplary methionine aminopeptidase inhibitors include bengamide or a derivative thereof and PPI-2458.

Nonlimiting exemplary bisphosphonates include etridonic acid, clodronic acid, tiludronic acid, pamidronic acid, alendronic acid, ibandronic acid, risedronic acid, and zoledronic acid.

Nonlimiting exemplary heparanase inhibitors include compounds that target, decrease, or inhibit heparin sulfate degradation, such as PI-88 and OGT2115.

Nonlimiting exemplary compounds which target, decrease, or inhibit the oncogenic activity of Ras include farnesyl transferase inhibitors, such as L-744832, DK8G557, tipifarnib, and lonafarnib.

Nonlimiting exemplary telomerase inhibitors include compounds that target, decrease, or inhibit the activity of telomerase, such as compounds that inhibit the telomerase receptor, such as telomestatin.

Nonlimiting exemplary proteasome inhibitors include compounds that target, decrease, or inhibit the activity of the proteasome including, but not limited to, bortezomib. In some embodiments, the proteasome inhibitor is carfilzomib.

Nonlimiting exemplary FMS-like tyrosine kinase inhibitors, which are compounds targeting, decreasing or inhibiting the activity of FMS-like tyrosine kinase receptors (Flt-3R) include interferon, I-β-D-arabinofuransylcytosine (ara-c), and bisulfan; and ALK inhibitors, which are compounds which target, decrease, or inhibit anaplastic lymphoma kinase.

Nonlimiting exemplary Flt-3 inhibitors include PKC412, midostaurin, a staurosporine derivative, SU11248, and MLN518.

Nonlimiting exemplary HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino,17-demethoxygeldanamycin (17AAG), a geldanamycin derivative; other geldanamycin related compounds; radicicol and HDAC inhibitors.

Nonlimiting exemplary protein tyrosine kinase and/or serine and/or threonine kinase inhibitors or lipid kinase inhibitors, include a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SUIOI, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, CI-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Nonlimiting exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with TG02, or a pharmaceutically acceptable salt thereof, include: avastin, daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, I-(4-chloroanilino)-4-(4-pyridylmethyl)phthalazine or a pharmaceutically acceptable salt thereof, 1-(4-chloroanilino)-4-(4-pyridylmethyl) phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

A number of suitable optional therapeutic, e.g., anticancer, agents are contemplated for use in the therapeutic methods provided herein. Indeed, the methods provided herein can include, but are not limited to, administration of numerous optional therapeutic agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of optional therapeutic agents such as chemotherapeutic compounds and anticancer therapies suitable for co-administration with the disclosed compounds are known to those skilled in the art.

In certain embodiments, anticancer agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor. Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the therapeutic methods provided herein include administering to a cancer patient a therapeutically effective amount of a TG02 polymorphic form and at least one additional anti-hyperproliferative or antineoplastic agent selected from alkylating agents, antimetabolites, and natural products (e.g., herbs and other plant and/or animal derived compounds).

Alkylating agents suitable for use in the present methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimidazolecarboxamide).

In some embodiments, antimetabolites suitable for use in the present methods include, but are not limited to: 1) folic acid analogs (e.g., methotrexate (amethopterin)); 2) pyrimidine analogs (e.g., fluorouracil (5-fluorouracil; 5-FU), floxuridine (fluorodeoxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the methods of the present disclosure include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the therapeutic methods of the present disclosure. For example, the U.S. Food and Drug Administration (FDA) maintains a formulary of oncolytic agents approved for use in the United States. International counterpart agencies to the FDA maintain similar formularies. Those skilled in the art will appreciate that the "product labels" required on all U.S. approved chemotherapeutics describe approved indications, dosing information, toxicity data, and the like, for the exemplary agents.

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUCI-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-715992, SGN-0010, SGN-40, sorafenib, regorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other optional therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

In some embodiments, methods provided herein comprise administering a TG02 polymorphic form to a cancer patient in combination with radiation therapy. The methods provided herein are not limited by the types, amounts, or delivery and administration systems used to deliver the therapeutic dose of radiation to a patient. For example, the patient may receive photon radiotherapy, particle beam radiation therapy, other types of radiotherapies, and combinations thereof. In some embodiments, the radiation is delivered to the patient using a linear accelerator. In still other embodiments, the radiation is delivered using a gamma knife.

The source of radiation can be external or internal to the patient. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The patient may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to a patient is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the methods provided herein.

II. Therapeutic Methods

In the therapeutic methods provided herein, the TG02 polymorphic form and optional therapeutic, e.g., anticancer, agent may be administered to a cancer patient under one or more of the following conditions: at different periodicities, at different durations, at different concentrations, by different administration routes, etc.

In some embodiments, the TG02 polymorphic form is administered prior to the optional therapeutic agent, e.g., 0.5, 1, 2, 3, 4, 5, 10, 12, or 18 hours, 1, 2, 3, 4, 5, or 6 days, or 1, 2, 3, or 4 weeks prior to the administration of optional therapeutic agent.

In some embodiments, the TG02 polymorphic form is administered after the optional therapeutic agent, e.g., 0.5, 1, 2, 3, 4, 5, 10, 12, or 18 hours, 1, 2, 3, 4, 5, or 6 days, or 1, 2, 3, or 4 weeks after the administration of the optional therapeutic agent.

In some embodiments, the TG02 polymorphic form and the optional therapeutic agent are administered concurrently but on different schedules, e.g., the TG02 polymorphic form is administered daily while the immune checkpoint inhibitor is administered once a week, once every two weeks, once every three weeks, or once every four weeks. In other embodiments, the TG02 polymorphic form is administered once a day while the immune checkpoint inhibitor and/or the optional therapeutic agent is administered once a week, once every two weeks, once every three weeks, or once every four weeks.

The therapeutic methods provided herein comprise administering a TG02 polymorphic form to a cancer patient in an amount which is effective to achieve its intended purpose. While individual needs vary, determination of optimal ranges of effective amounts of each component is within the skill of the art. Typically, a TG02 polymorphic form may be administered in an amount from about 1 mg/kg to about 500 mg/kg, about 1 mg/kg to about 100 mg/kg, or about 1 mg/kg to about 50 mg/kg. The dosage of a composition can be at any dosage including, but not limited to, 30-600 mg/day. Particular doses include 50, 100, 200, 250, 300, 400, 500, and 600 mg/day. In one embodiment, a TG02 polymorphic form is administered once a day on 3-7 consecutive days prior to the administration of the immune checkpoint inhibitor. In another embodiment, 250 mg/day of a TG02 polymorphic form is administered. In another embodiment, 250 mg/day of a TG02 polymorphic form is administered twice weekly. In another embodiment, TG02 polymorphic form administration continues on the day of the immune checkpoint inhibitor and continues for additional days until disease progression or until TG02 polymorphic form administration is no longer beneficial. These dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

The unit oral dose of the TG02 polymorphic form may comprise from about 0.01 to about 1000 mg, e.g., about 10 to about 500 mg of the TG02 polymorphic form. In one embodiment, the unit oral dose of the TG02 polymorphic form is 10 mg, 20 mg, 30 mg, 40 mg, 50 mg, 60 mg, 70 mg 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, or 300 mg. The unit dose may be administered one or more times daily, e.g., as one or more tablets or capsules.

In addition to administering the TG02 polymorphic form as a raw chemical, it may be administered as part of a pharmaceutical preparation or composition. In some embodiments, the pharmaceutical preparation or composition can include one or more pharmaceutically acceptable carriers, excipients, and/or auxiliaries. In some embodiments, the one or more carriers, excipients, and/or auxiliaries facilitate processing of the TG02 polymorphic form into a preparation or composition which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the one or more carriers, excipients, and/or auxiliaries.

The pharmaceutical compositions of provided herein may be administered to any patient which may experience the beneficial effects of the TG02 polymorphic form. Foremost among such patients are mammals, e.g., humans, although the methods and compositions provided herein are not intended to be so limited. Other patients include veterinary animals (cows, sheep, pigs, horses, dogs, cats and the like).

The pharmaceutical compositions provided herein are manufactured by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

The term "excipient" as used herein refers to any ingredient in a composition other than the TG02 polymorphic form. An excipient is typically an inert substance added to a composition to facilitate processing, handling, administration, etc. of the TG02 polymorphic form. Useful excipients include, but are not limited to, adjuvants, antiadherents, binders, carriers, disintegrants, fillers, flavors, colors, diluents, lubricants, glidants, preservatives, sorbents, solvents, surfactants, and sweeteners. In one embodiment, the composition comprises at least one excipient selected from the group consisting of silicified microcrystalline cellulose, hypromellose 2910, crospvidone, and magnesium stearate. In one embodiment, the composition comprises silicified microcrystalline cellulose.

Conventional pharmaceutical excipients are well known to those of skill in the art. In particular, one of skill in the art will recognize that a wide variety of pharmaceutically acceptable excipients can be used in admixture with crystalline polymorphic forms of TG02, including those listed in the *Handbook of Pharmaceutical Excipients*, Pharmaceutical Press 4th Ed. (2003), and *Remington: The Science and Practice of Pharmacy*, Lippincott Williams & Wilkins, 21st ed. (2005).

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries can be suitable flow-regulating agents and lubricants. Suitable auxiliaries include, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension including, for example, sodium carboxymethyl cellulose, sorbitol, and/or dextran. Optionally, the suspension may also contain stabilizers.

Therapeutically effective amounts of the TG02 polymorphic form and/or the immune checkpoint inhibitor and/or the optional therapeutic agent formulated in accordance with standard pharmaceutical practices, are administered to a human patient in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

The TG02 polymorphic form, the immune checkpoint inhibitor and/or the optional therapeutic agent can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein the TG02 polymorphic form, the immune checkpoint inhibitor and/or the optional therapeutic agent are administered in an effective amount to achieve its intended purpose. The exact formulation, route of administration, and dosage is determined by an individual physician in view of the diagnosed condition or disease. Dosage amount and interval can be adjusted individually to provide levels of TG02, immune checkpoint inhibitor, COX-2 inhibitor, and/or optional therapeutic agent that is sufficient to maintain therapeutic effects.

Toxicity and therapeutic efficacy of TG02, the immune checkpoint inhibitor and/or the optional therapeutic agent can be determined by standard pharmaceutical procedures in cell cultures or experimental animals, e.g., for determining the maximum tolerated dose (MTD) of a compound, which defines as the highest dose that causes no toxicity in a patient. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of the TG02 polymorphic form, immune checkpoint inhibitor and/or optional therapeutic agent required for use in therapy varies with the nature of the condition being treated, the length of time that activity is desired, and the age and the condition of the patient, and ultimately is determined by the attendant physician. For example, dosage amounts and intervals can be adjusted individually to provide plasma levels of TG02 and immune checkpoint inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, the TG02 polymorphic form and immune checkpoint inhibitor can be administered at a frequency of: one dose per day; four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The immune checkpoint inhibitor is administered in therapeutically effective amounts. When the immune checkpoint inhibitor is a monoclonal antibody, 1-20 mg/kg is administered as an intravenous infusion every 2-4 weeks. For example, 50 mg, 60 mg, 70 mg, 80 mg, 90 mg, 100 mg, 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg and 2000 mg of the antibody may be administered.

For example, when the immune checkpoint inhibitor is the anti-PD-1 antibody nivolumab, 3 mg/kg may be administered by intravenous infusion over 60 minutes every two weeks. When the immune checkpoint inhibitor is the anti-PD-1 antibody pembrolizumab, 2 mg/kg may be administered by intravenous infusion over 30 minutes every two or three weeks. When the immune checkpoint inhibitor is the anti-PD-L1 antibody avelumab, 10 mg/kg may be administered by intravenous infusion as frequently as every 2 weeks. Disis et al., *J. Clin Oncol.* 33 (2015) (suppl; abstr 5509). When the immune checkpoint inhibitor is the anti-PD-L1 antibody MPDL3280A, 20 mg/kg may be administered by intravenous infusion every 3 weeks. Herbst et al., *Nature* 515:563-80 (2014). When the immune checkpoint inhibitor is the anti-CTLA-4 antibody ipilumumab, 3 mg/kg may be administered by intravenous infusion over 90 minutes every 3 weeks. When the immune checkpoint inhibitor is the anti-CTLA-4 antibody tremelimumab, 15 mg/kg may be administered by intravenous infusion every 12 weeks. Naido et al., *British Journal of Cancer* 111.2214-19 (2014); Drugs R D, 10:123-32 (2010). When the immune checkpoint inhibitor is the anti-LAG3 antibody GSK2831781, 1.5 to 5 mg/kg may be administered by intravenous infusion over 120 minutes every 2-4 weeks. When the immune checkpoint inhibitor is an anti-TIM3 antibody, 1-5 mg/kg may be administered by intravenous infusion over 30-90 minutes every 2-4 weeks. When an inhibitor of indoleamine 2,3-dioxygenase (IDO) pathway is inhibitor indoximod in combination with temozolomide, 18.5 mg/kg/dose BID with an escalation to 27.7 mg/kg/dose BID of indoximod with 200 mg/m$^2$ every 5 days of temozolomide.

In one embodiment, the immune checkpoint inhibitor is an antibody and 1-20 mg/kg is administered by intravenous infusion every 2-4 weeks. In another embodiment, 50-2000 mg of the antibody is administered by intravenous infusion every 2-4 weeks. In another embodiment, TG02 is administered prior to administration of the antibody. In another embodiment, TG02 is administered 3-7 days prior to the day of administration of the antibody. In another embodiment, TG02 is also administered the day the antibody is administered and on consecutive days thereafter until disease progression or until TG02 administration is no longer beneficial.

In one embodiment, the cancer patient has tumors with a biomarker, e.g., overexpression of MYC and/or MCL1, and receives 2 mg/kg pembrolizumab administered by intravenous infusion every three weeks and 30-600 mg of TG02 administered for 3-7 days prior to pembrolizumab administration, on the day of pembrolizumab administration, and thereafter until disease progression or until there is no therapeutic benefit.

In another embodiment, the cancer patient has tumors with a biomarker, e.g., overexpression of MYC and/or MCL1, and receives 3 mg/kg nivolumab administered by intravenous infusion every 2 weeks and 30-600 mg TG02 administered orally for 3-7 days prior to nivolumab administration, on the day of nivolumab administration, and thereafter until disease progression or until there is no therapeutic benefit.

In another embodiment, the cancer patient has tumors with a biomarker, e.g., overexpression of MYC and/or MCL1, and receives 3 mg/kg nivolumab administered by intravenous infusion every 2 weeks and 30-600 mg TG02 administered orally twice weekly prior to nivolumab administration, on the day of nivolumab administration, and thereafter until disease progression or until there is no therapeutic benefit.

In another embodiment, the treatment of the cancer patient with an immune checkpoint inhibitor and the TG02 polymorphic form induces anti-proliferative response faster than when the immune checkpoint inhibitor is administered alone.

In another embodiment, the treatment of the cancer patient with a COX-2 inhibitor and the TG02 polymorphic form induces anti-proliferative response faster than when the COX-2 inhibitor is administered alone.

The present disclosure also provides the following particular embodiments with respect to pharmaceutical compositions comprising TG02 Form X (citrate) and pharmaceutically acceptable excipients.

Embodiment 1

A pharmaceutical composition comprising, by weight:
(a) about 7% to about 70% of TG02 Form X (citrate);
(b) about 20% to about 83% of a filler;
(c) about 1% to about 10% of a disintegrant;
(d) about 1% to about 10% of a binder; and
(e) about 0.1% to about 1% of a lubricant.

Embodiment 2

The pharmaceutical composition of Embodiment 1, comprising about 60% to about 65% of TG02 Form X (citrate).

Embodiment 3

The pharmaceutical composition of Embodiments 1 or 2, comprising about 25% to about 30% of a filler.

Embodiment 4

The pharmaceutical composition of Embodiment 1, comprising about 35% to about 40% of TG02 Form X (citrate).

Embodiment 5

The pharmaceutical composition of Embodiments 1 or 4, comprising about 50% to about 55% of a filler.

Embodiment 6

The pharmaceutical composition of Embodiment 1, comprising about 5% to about 10% of TG02 Form X (citrate).

Embodiment 7

The pharmaceutical composition of Embodiments 1 or 4, comprising about 80% to about 85% of a filler.

Embodiment 8

The pharmaceutical composition of any one of Embodiments 1-7, comprising about 5% of a disintegrant.

Embodiment 9

The pharmaceutical composition of any one of Embodiments 1-8, comprising about 5% of a binder.

Embodiment 10

The pharmaceutical composition of any one of Embodiments 1-9, comprising about 0.5% of a lubricant.

Embodiment 11

The pharmaceutical composition of any one of Embodiments 1-10, wherein the filler is selected from the group consisting of microcrystalline cellulose, silicified microcrystalline cellulose, lactose monohydrate, and mannitol.

Embodiment 12

The pharmaceutical composition of Embodiment 11, wherein the filler is silicified microcrystalline cellulose.

Embodiment 13

The pharmaceutical composition of any one of Embodiments 1-12, wherein the disintegrant selected from the group consisting of crospovidone and sodium starch glycolate.

Embodiment 14

The pharmaceutical composition of Embodiment 13, wherein the disintegrant is crospovidone.

Embodiment 15

The pharmaceutical composition of any one of Embodiments 1-14, wherein the binder is hydroxypropyl methylcellulose.

Embodiment 16

The pharmaceutical composition of any one of Embodiments 1-15, wherein the lubricant is selected from the group consisting of magnesium stearate and sodium stearyl fumarate.

Embodiment 17

The pharmaceutical composition of any one of Embodiments 1-15, wherein the lubricant is magnesium stearate.

Embodiment 18

The pharmaceutical composition of claim 1 comprising: (a) about 36.3% of TG02 Form X (citrate); (b) about 53.2% of silicified microcrystalline cellulose; (c) about 5% of crospovidone; (d) about 5% of hydroxypropyl methylcellulose; and (e) about 0.5% of magnesium stearate.

Embodiment 19

The pharmaceutical composition of claim 1 comprising: (a) about 63.5% of TG02 Form X (citrate); (b) about 26% of silicified microcrystalline cellulose; (c) about 5% of crospovidone; (d) about 5% of hydroxypropyl methylcellulose; and (e) about 0.5% of magnesium stearate.

Embodiment 20

The pharmaceutical composition of claim 1 comprising: (a) about 7.5% of TG02 Form X (citrate); (b) about 82% of silicified microcrystalline cellulose; (c) about 5% of crospovidone; (d) about 5% of hydroxypropyl methylcellulose; and (e) about 0.5% of magnesium stearate.

Embodiment 21

The pharmaceutical composition of any one of Embodiments 1-20 for oral administration to a subject in need thereof.

Embodiment 22

The pharmaceutical composition of claim 22 for oral administration in a capsule.

Embodiment 23

The pharmaceutical composition of any one of claims 1-3 or 8-22 providing about 225 mg to about 230 mg of TG02 Form X (citrate) as a unit dose in a capsule.

Embodiment 24

The pharmaceutical composition of any one of claims 1, 4, 5, or 8-22 providing about 75 mg to about 80 mg of TG02 Form X (citrate) as a unit dose in a capsule.

Embodiment 25

The pharmaceutical composition of any one of claim 1 or 6-22 providing about 13 mg to about 18 mg of TG02 Form X (citrate) as a unit dose in a capsule.

III. Biomarkers

The term "biomarker" as used herein refers to any biological compound, such as a gene, a protein, a fragment of a protein, a peptide, a polypeptide, a nucleic acid, etc., that can be detected and/or quantified in a cancer patient in vivo or in a biological sample obtained from a cancer patient. A biomarker can be the entire intact molecule, or it can be a portion or fragment thereof. In one embodiment, the expression level of the biomarker is measured. The expression level of the biomarker can be measured, for example, by detecting the protein or RNA, e.g., mRNA, level of the biomarker. In some embodiments, portions or fragments of biomarkers can be detected or measured, for example, by an antibody or other specific binding agent. In some embodiments, a measurable aspect of the biomarker is associated with a given state of the patient, such as a particular stage of cancer. For biomarkers that are detected at the protein or RNA level, such measurable aspects may include, for example, the presence, absence, or concentration, i.e., expression level, of the biomarker in a cancer patient, or biological sample obtained from the cancer patient. For biomarkers that are detected at the nucleic acid level, such measurable aspects may include, for example, allelic versions of the biomarker or type, rate, and/or degree of mutation of the biomarker, also referred to herein as mutation status.

For biomarkers that are detected based on expression level of protein or RNA, expression level measured between different phenotypic statuses can be considered different, for example, if the mean or median expression level of the biomarker in the different groups is calculated to be statistically significant. Common tests for statistical significance include, among others, t-test, ANOVA, Kruskal-Wallis, Wilcoxon, Mann-Whitney, Significance Analysis of Microarrays, odds ratio, etc. Biomarkers, alone or in combination, provide measures of relative likelihood that a subject belongs to one phenotypic status or another. Therefore, they are useful, inter alia, as markers for disease and as indicators that particular therapeutic treatment regimens will likely result in beneficial patient outcomes.

Biomarkers include, but are not limited, the genes listed in Table 1. In one embodiment, the measurable aspect of the biomarker is its expression status. In one embodiment, the measurable aspect of the biomarker is its mutation status.

TABLE 1

| Gene | Gene synonym | Gene description |
|---|---|---|
| A2M | CPAMD5, FWP007, S863-7 | Alpha-2-macroglobulin |
| ABCB1 | ABC20, CD243, CLCS, GP170, MDR1, P-gp, PGY1 | ATP-binding cassette, sub-family B (MDR/TAP), member 1 |
| ABCC1 | GS-X, MRP, MRP1 | ATP-binding cassette, sub-family C (CFTR/MRP), member 1 |
| ABCC2 | CMOAT, cMRP, DJS, MRP2 | ATP-binding cassette, sub-family C (CFTR/MRP), member 2 |
| ABCC3 | cMOAT2, EST90757, MLP2, MOAT-D, MRP3 | ATP-binding cassette, sub-family C (CFTR/MRP), member 3 |
| ABCC5 | EST277145, MOAT-C, MRP5, SMRP | ATP-binding cassette, sub-family C (CFTR/MRP), member 5 |
| ABCC6 | ARA, EST349056, MLP1, MRP6, PXE, URG7 | ATP-binding cassette, sub-family C (CFTR/MRP), member 6 |
| ABCG2 | ABCP, BCRP, CD338, EST157481, MXR | ATP-binding cassette, sub-family G (WHITE), member 2 (Junior blood group) |
| ABL1 | ABL, c-ABL, JTK7, p150 | ABL proto-oncogene 1, non-receptor tyrosine kinase |
| ABL2 | ABLL, ARG | ABL proto-oncogene 2, non-receptor tyrosine kinase |
| ACAP1 | CENTB1, KIAA0050 | ArfGAP with coiled-coil, ankyrin repeat and PH domains 1 |
| ACLY | ACL, ATPCL, CLATP | ATP citrate lyase |
| ACPP | ACP-3, ACP3 | Acid phosphatase, prostate |

TABLE 1-continued

| Gene | Gene synonym | Gene description |
|---|---|---|
| ACVR1B | ActRIB, ACVRLK4, ALK4, SKR2 | Activin A receptor, type IB |
| ACVR2A | ACTRII, ACVR2 | Activin A receptor, type IIA |
| ACVR2B | ActR-IIB | Activin A receptor, type IIB |
| ADAM9 | CORD9, KIAA0021, MCMP, MDC9, Mltng | ADAM metallopeptidase domain 9 |
| ADAMTS1 | C3-C5, KIAA1346, METH1 | ADAM metallopeptidase with thrombospondin type 1 motif, 1 |
| ADAMTS14 | | ADAM metallopeptidase with thrombospondin type 1 motif, 14 |
| ADAMTS18 | ADAMTS21 | ADAM metallopeptidase with thrombospondin type 1 motif, 18 |
| ADAMTS20 | GON-1 | ADAM metallopeptidase with thrombospondin type 1 motif, 20 |
| ADAMTS3 | ADAMTS-4, KIAA0366 | ADAM metallopeptidase with thrombospondin type 1 motif, 3 |
| ADAMTS4 | ADAMTS-2, ADMP-1, KIAA0688 | ADAM metallopeptidase with thrombospondin type 1 motif, 4 |
| ADAMTS5 | ADAMTS11, ADMP-2 | ADAM metallopeptidase with thrombospondin type 1 motif, 5 |
| ADAMTS6 | ADAM-TS6 | ADAM metallopeptidase with thrombospondin type 1 motif, 6 |
| ADAMTS8 | ADAM-TS8, FLJ41712, METH2 | ADAM metallopeptidase with thrombospondin type 1 motif, 8 |
| ADAMTS9 | KIAA1312 | ADAM metallopeptidase with thrombospondin type 1 motif, 9 |
| ADM | AM | Adrenomedullin |
| ADRA1B | | Adrenoceptor alpha 1B |
| AFP | FETA, HPAFP | Alpha-fetoprotein |
| AGER | RAGE | Advanced glycosylation end product-specific receptor |
| AHR | bHLHe76 | Aryl hydrocarbon receptor |
| AHSG | A2HS, FETUA, HSGA | Alpha-2-HS-glycoprotein |
| AKAP12 | AKAP250, SSeCKS | A kinase (PRKA) anchor protein 12 |
| AKR1B1 | ALDR1, AR | Aldo-keto reductase family 1, member B1 (aldose reductase) |
| AKT1 | AKT, PKB, PRKBA, RAC | V-akt murine thymoma viral oncogene homolog 1 |
| AKT2 | | V-akt murine thymoma viral oncogene homolog 2 |
| AKT3 | PKBG, PRKBG, RAC-gamma | V-akt murine thymoma viral oncogene homolog 3 |
| ALB | | Albumin |
| ALCAM | CD166, MEMD | Activated leukocyte cell adhesion molecule |
| ALDOA | | Aldolase A, fructose-bisphosphate |
| ALDOB | | Aldolase B, fructose-bisphosphate |
| ALDOC | | Aldolase C, fructose-bisphosphate |
| ALPL | HOPS, TNSALP | Alkaline phosphatase, liver/bone/kidney |
| ALPP | | Alkaline phosphatase, placental |
| ANG | RNASE5 | Angiogenin, ribonuclease, RNase A family, 5 |
| ANGPT1 | Ang1, KIAA0003 | Angiopoietin 1 |
| ANGPT2 | Ang2 | Angiopoietin 2 |
| ANXA1 | ANX1, LPC1 | Annexin A1 |
| ANXA11 | ANX11 | Annexin A11 |
| ANXA2 | ANX2, ANX2L4, CAL1H, LIP2, LPC2D | Annexin A2 |
| ANXA4 | ANX4 | Annexin A4 |
| ANXA7 | ANX7 | Annexin A7 |
| AOC3 | HPAO, VAP-1, VAP1 | Amine oxidase, copper containing 3 |
| AP2B1 | ADTB2, CLAPB1 | Adaptor-related protein complex 2, beta 1 subunit |
| APAF1 | APAF-1, CED4 | Apoptotic peptidase activating factor 1 |
| APEX1 | APE, APE-1, APEN, APEX, APX, HAP1, REF-1, REF1 | APEX nuclease (multifunctional DNA repair enzyme) 1 |
| APOA1 | | Apolipoprotein A-I |
| APOA2 | | Apolipoprotein A-II |
| APOC1 | | Apolipoprotein C-I |
| APOC3 | | Apolipoprotein C-III |
| APOD | | Apolipoprotein D |
| APOE | AD2 | Apolipoprotein E |
| APPBP2 | Hs.84084, KIAA0228, PAT1 | Amyloid beta precursor protein (cytoplasmic tail) binding protein 2 |
| AR | AIS, DHTR, HUMARA, NR3C4, SBMA, SMAX1 | Androgen receptor |

TABLE 1-continued

| Gene | Gene synonym | Gene description |
|---|---|---|
| AREG | AREGB, SDGF | Amphiregulin |
| ARG2 | | Arginase 2 |
| ARNT | bHLHe2, HIF-1 beta | Aryl hydrocarbon receptor nuclear translocator |
| ASPH | BAH, CASQ2BP1, HAAH, JCTN | Aspartate beta-hydroxylase |
| ATM | ATA, ATC, ATD, ATDC, TEL1, TELO1 | ATM serine/threonine kinase |
| ATOH1 | bHLHa14, HATH1, MATH-1, Math1 | Atonal homolog 1 (*Drosophila*) |
| ATP7B | WND | ATPase, Cu++ transporting, beta polypeptide |
| AURKA | AIK, ARK1, AurA, BTAK, PPP1R47, STK15, STK6, STK7 | Aurora kinase A |
| AURKB | Aik2, AIM-1, ARK2, AurB, IPL1, PPP1R48, STK12, STK5 | Aurora kinase B |
| AZGP1 | ZA2G, ZAG | Alpha-2-glycoprotein 1, zinc-binding |
| B2M | | Beta-2-microglobulin |
| BAD | BBC2, BCL2L8 | BCL2-associated agonist of cell death |
| BAG1 | | BCL2-associated athanogene |
| BAI1 | | Brain-specific angiogenesis inhibitor 1 |
| BAX | BCL2L4 | BCL2-associated X protein |
| BCL11A | BCL11A-L, BCL11A-S, BCL11A-XL, CTIP1, EVI9, HBFQTL5, ZNF856 | B-cell CLL/lymphoma 11A (zinc finger protein) |
| BCL2 | Bcl-2, PPP1R50 | B-cell CLL/lymphoma 2 |
| BCL2A1 | ACC-1, ACC-2, BCL2L5, BFL1, GRS, HBPA1 | BCL2-related protein A1 |
| BCL2L1 | Bcl-X, bcl-xL, bcl-xS, BCL2L, BCLX, PPP1R52 | BCL2-like 1 |
| BCL2L2 | BCL-W, KIAA0271, PPP1R51 | BCL2-like 2 |
| BCL2L2-PABPN1 | | BCL2L2-PABPN1 readthrough |
| BCL3 | BCL4, D19S37 | B-cell CLL/lymphoma 3 |
| BCL6 | BCL5, BCL6A, LAZ3, ZBTB27, ZNF51 | B-cell CLL/lymphoma 6 |
| BDNF | | Brain-derived neurotrophic factor |
| BIRC2 | API1, c-IAP1, cIAP1, hiap-2, MIHB, RNF48 | Baculoviral IAP repeat containing 2 |
| BIRC3 | API2, c-IAP2, cIAP2, hiap-1, MALT2, MIHC, RNF49 | Baculoviral IAP repeat containing 3 |
| BIRC5 | API4, EPR-1, survivin | Baculoviral IAP repeat containing 5 |
| BIRC6 | BRUCE | Baculoviral IAP repeat containing 6 |
| BLK | MGC10442 | BLK proto-oncogene, Src family tyrosine kinase |
| BLMH | BH | Bleomycin hydrolase |
| BMI1 | PCGF4, RNF51 | BMI1 proto-oncogene, polycomb ring finger |
| BMP2 | BMP2A | Bone morphogenetic protein 2 |
| BMP4 | BMP2B | Bone morphogenetic protein 4 |
| BNIP3 | Nip3 | BCL2/adenovirus E1B 19 kDa interacting protein 3 |
| BNIP3L | BNIP3a, Nix | BCL2/adenovirus E1B 19 kDa interacting protein 3-like |
| BRCA1 | BRCC1, PPP1R53, RNF53 | Breast cancer 1, early onset |
| BRCA2 | BRCC2, FACD, FAD, FAD1, FANCD, FANCD1 | Breast cancer 2, early onset |
| BRMS1 | DKFZP564A063 | Breast cancer metastasis suppressor 1 |
| BTG2 | MGC126063, MGC126064, PC3, TIS21 | BTG family, member 2 |
| C18orf8 | HsT2591, MIC-1, MIC1 | Chromosome 18 open reading frame 8 |
| C1QBP | gC1Q-R, gC1qR, HABP1, p32, SF2p32 | Complement component 1, q subcomponent binding protein |
| C6 | | Complement component 6 |
| C7 | | Complement component 7 |
| CA8 | CALS, CARP | Carbonic anhydrase VIII |
| CALCA | CALC1 | Calcitonin-related polypeptide alpha |
| CALM1 | CALML2, CAMI, DD132, PHKD | Calmodulin 1 (phosphorylase kinase, delta) |
| CALM2 | CAMII, PHKD | Calmodulin 2 (phosphorylase kinase, delta) |
| CALM3 | PHKD | Calmodulin 3 (phosphorylase kinase, delta) |
| CALR | cC1qR, CRT, FLJ26680, RO, SSA | Calreticulin |

TABLE 1-continued

| Gene | Gene synonym | Gene description |
|---|---|---|
| CANX | CNX, IP90, P90 | Calnexin |
| CAPN6 | CalpM, CANPX, CAPNX | Calpain 6 |
| CASC3 | BTZ, MLN51 | Cancer susceptibility candidate 3 |
| CASP1 | ICE, IL1BC | Caspase 1, apoptosis-related cysteine peptidase |
| CASP10 | MCH4 | Caspase 10, apoptosis-related cysteine peptidase |
| CASP2 | ICH1, MGC2181, NEDD2, PPP1R57 | Caspase 2, apoptosis-related cysteine peptidase |
| CASP3 | apopain, CPP32, CPP32B, Yama | Caspase 3, apoptosis-related cysteine peptidase |
| CASP4 | ICE(rel)II, ICH-2, TX | Caspase 4, apoptosis-related cysteine peptidase |
| CASP5 | ICE(rel)III | Caspase 5, apoptosis-related cysteine peptidase |
| CASP6 | MCH2 | Caspase 6, apoptosis-related cysteine peptidase |
| CASP7 | CMH-1, ICE-LAP3, MCH3 | Caspase 7, apoptosis-related cysteine peptidase |
| CASP8 | Casp-8, FLICE, MACH, MCH5 | Caspase 8, apoptosis-related cysteine peptidase |
| CASP9 | APAF-3, ICE-LAP6, MCH6, PPP1R56 | Caspase 9, apoptosis-related cysteine peptidase |
| CAT | | Catalase |
| CAV1 | CAV | Caveolin 1, caveolae protein, 22 kDa |
| CBL | c-Cbl, CBL2, RNF55 | Cbl proto-oncogene, E3 ubiquitin protein ligase |
| CCKBR | | Cholecystokinin B receptor |
| CCL11 | eotaxin, MGC22554, SCYA11 | Chemokine (C-C motif) ligand 11 |
| CCL13 | CKb10, MCP-4, MGC17134, NCC-1, SCYA13, SCYL1 | Chemokine (C-C motif) ligand 13 |
| CCL14 | CKb1, HCC-1, HCC-3, MCIF, NCC-2, SCYA14, SCYL2 | Chemokine (C-C motif) ligand 14 |
| CCL16 | CKb12, HCC-4, LCC-1, LEC, LMC, Mtn-1, NCC-4, SCYA16, SCYL4 | Chemokine (C-C motif) ligand 16 |
| CCL18 | AMAC-1, CKb7, DC-CK1, DCCK1, MIP-4, PARC, SCYA18 | Chemokine (C-C motif) ligand 18 (pulmonary and activation-regulated) |
| CCL19 | CKb11, ELC, exodus-3, MIP-3b, SCYA19 | Chemokine (C-C motif) ligand 19 |
| CCL2 | GDCF-2, HC11, MCAF, MCP-1, MCP1, MGC9434, SCYA2, SMC-CF | Chemokine (C-C motif) ligand 2 |
| CCL21 | 6Ckine, CKb9, ECL, exodus-2, SCYA21, SLC, TCA4 | Chemokine (C-C motif) ligand 21 |
| CCL23 | Ckb-8, CKb8, MIP-3, MPIF-1, SCYA23 | Chemokine (C-C motif) ligand 23 |
| CCL3 | G0S19-1, LD78ALPHA, MIP-1-alpha, SCYA3 | Chemokine (C-C motif) ligand 3 |
| CCL4 | Act-2, AT744.1, LAG1, MIP-1-beta, SCYA4 | Chemokine (C-C motif) ligand 4 |
| CCL5 | D17S136E, MGC17164, RANTES, SCYA5, SISd, TCP228 | Chemokine (C-C motif) ligand 5 |
| CCL7 | FIC, MARC, MCP-3, MCP3, NC28, SCYA6, SCYA7 | Chemokine (C-C motif) ligand 7 |
| CCL8 | HC14, MCP-2, SCYA8 | Chemokine (C-C motif) ligand 8 |
| CCNA1 | CT146 | Cyclin A1 |
| CCNA2 | CCN1, CCNA | Cyclin A2 |
| CCNB1 | CCNB | Cyclin B1 |
| CCNB2 | HsT17299 | Cyclin B2 |
| CCND1 | BCL1, D11S287E, PRAD1, U21B31 | Cyclin D1 |
| CCND2 | | Cyclin D2 |
| CCNE1 | CCNE | Cyclin E1 |
| CCNE2 | CYCE2 | Cyclin E2 |
| CCNG1 | CCNG | Cyclin G1 |
| CCNG2 | | Cyclin G2 |
| CCNH | CycH, p34, p37 | Cyclin H |
| CCR10 | GPR2 | Chemokine (C-C motif) receptor 10 |
| CCR7 | BLR2, CD197, CDw197, CMKBR7, EBI1 | Chemokine (C-C motif) receptor 7 |

TABLE 1-continued

| Gene | Gene synonym | Gene description |
|---|---|---|
| CD14 | | CD14 molecule |
| CD27 | S152, TNFRSF7, Tp55 | CD27 molecule |
| CD36 | FAT, GP3B, GP4, GPIV, SCARB3 | CD36 molecule (thrombospondin receptor) |
| CD38 | | CD38 molecule |
| CD40 | Bp50, p50, TNFRSF5 | CD40 molecule, TNF receptor superfamily member 5 |
| CD40LG | CD154, CD40L, gp39, hCD40L, HIGM1, IMD3, TNFSF5, TRAP | CD40 ligand |
| CD44 | CD44R, CSPG8, HCELL, IN, MC56, MDU2, MDU3, MIC4, Pgp1 | CD44 molecule (Indian blood group) |
| CD46 | MCP, MGC26544, MIC10, TLX, TRA2.10 | CD46 molecule, complement regulatory protein |
| CD52 | CDW52 | CD52 molecule |
| CD59 | 16.3A5, EJ16, EJ30, EL32, G344, MIC11, MIN1, MIN2, MIN3, MSK21, p18-20 | CD59 molecule, complement regulatory protein |
| CD70 | CD27L, CD27LG, TNFSF7 | CD70 molecule |
| CD74 | DHLAG | CD74 molecule, major histocompatibility complex, class II invariant chain |
| CD82 | IA4, KAI1, R2, ST6, TSPAN27 | CD82 molecule |
| CD9 | BA2, MIC3, MRP-1, P24, TSPAN29 | CD9 molecule |
| CDC16 | ANAPC6, APC6, CUT9 | Cell division cycle 16 |
| CDC20 | CDC20A, p55CDC | Cell division cycle 20 |
| CDC25A | | Cell division cycle 25A |
| CDC25B | | Cell division cycle 25B |
| CDC25C | CDC25, PPP1R60 | Cell division cycle 25C |
| CDC34 | E2-CDC34, UBC3, UBE2R1 | Cell division cycle 34 |
| CDC37 | P50CDC37 | Cell division cycle 37 |
| CDC6 | CDC18L | Cell division cycle 6 |
| CDH1 | CD324, UVO, uvomorulin | Cadherin 1, type 1, E-cadherin (epithelial) |
| CDH17 | cadherin, HPT-1 | Cadherin 17, LI cadherin (liver-intestine) |
| CDH5 | 7B4, CD144 | Cadherin 5, type 2 (vascular endothelium) |
| CDK1 | CDC2, CDC28A | Cyclin-dependent kinase 1 |
| CDK2 | | Cyclin-dependent kinase 2 |
| CDK4 | PSK-J3 | Cyclin-dependent kinase 4 |
| CDK6 | PLSTIRE | Cyclin-dependent kinase 6 |
| CDK7 | CAK, CAK1, CDKN7, MO15, STK1 | Cyclin-dependent kinase 7 |
| CDKN1A | CAP20, CDKN1, CIP1, P21, p21CIP1, p21Cip1/Waf1, SDI1, WAF1 | Cyclin-dependent kinase inhibitor 1A (p21, Cip1) |
| CDKN1C | BWCR, BWS, KIP2, P57 | Cyclin-dependent kinase inhibitor 1C (p57, Kip2) |
| CDKN2A | ARF, CDK4I, CDKN2, CMM2, INK4, INK4a, MLM, MTS1, p14, p14ARF, p16, p16INK4a, p19, p19Arf | Cyclin-dependent kinase inhibitor 2A |
| CEACAM5 | CD66e, CEA | Carcinoembryonic antigen-related cell adhesion molecule 5 |
| CEACAM6 | CD66c, NCA | Carcinoembryonic antigen-related cell adhesion molecule 6 (non-specific cross reacting antigen) |
| CENPF | hcp-1 | Centromere protein F, 350/400 kDa |
| CFHR1 | CFHL, CFHL1, CFHL1P, CFHR1P, FHR1, H36-1, H36-2, HFL1, HFL2 | Complement factor H-related 1 |
| CFLAR | c-FLIP, CASH, CASP8AP1, Casper, CLARP, FLAME, FLIP, I-FLICE, MRIT | CASP8 and FADD-like apoptosis regulator |
| CFTR | ABC35, ABCC7, CF, CFTR/MRP, dJ760C5.1, MRP7, TNR-CFTR | Cystic fibrosis transmembrane conductance regulator (ATP-binding cassette sub-family C, member 7) |
| CGA | FSHA, GPHa, GPHA1, HCG, LHA, TSHA | Glycoprotein hormones, alpha polypeptide |

TABLE 1-continued

| Gene | Gene synonym | Gene description |
| --- | --- | --- |
| CGB | CGB3 | Chorionic gonadotropin, beta polypeptide |
| CGB5 | HCG | Chorionic gonadotropin, beta polypeptide 5 |
| CGB7 | CG-beta-a | Chorionic gonadotropin, beta polypeptide 7 |
| CGB8 | | Chorionic gonadotropin, beta polypeptide 8 |
| CHD7 | CRG, FLJ20357, FLJ20361, KIAA1416 | Chromodomain helicase DNA binding protein 7 |
| CHEK1 | CHK1 | Checkpoint kinase 1 |
| CHEK2 | bA444G7, CDS1, CHK2, HuCds1, PP1425, RAD53 | Checkpoint kinase 2 |
| CHFR | FLJ10796, RNF196 | Checkpoint with forkhead and ring finger domains, E3 ubiquitin protein ligase |
| CHGA | | Chromogranin A (parathyroid secretory protein 1) |
| CHI3L1 | GP39, YKL40 | Chitinase 3-like 1 (cartilage glycoprotein-39) |
| CHP2 | | Calcineurin-like EF-hand protein 2 |
| CIB2 | DFNB48, KIP2, USH1J | Calcium and integrin binding family member 2 |
| CKB | CKBB | Creatine kinase, brain |
| CKS1B | CKS1, ckshs1 | CDC28 protein kinase regulatory subunit 1B |
| CKS2 | | CDC28 protein kinase regulatory subunit 2 |
| CLDN3 | C7orf1, CPE-R2, CPETR2, HRVP1, RVP1 | Claudin 3 |
| CLDN4 | CPE-R, CPETR, CPETR1, hCPE-R, WBSCR8 | Claudin 4 |
| CLDN7 | CEPTRL2, CPETRL2, Hs.84359 | Claudin 7 |
| CLEC3B | TN, TNA | C-type lectin domain family 3, member B |
| CLIC1 | NCC27, p64CLCP | Chloride intracellular channel 1 |
| CLIP1 | CLIP, CLIP-170, CLIP170, CYLN1, RSN | CAP-GLY domain containing linker protein 1 |
| CLSTN1 | CDHR12, CSTN1, KIAA0911 | Calsyntenin 1 |
| CLU | APOJ, CLI, CLU1, CLU2, KUB1, SGP-2, SP-40, TRPM-2 | Clusterin |
| CNN1 | Sm-Calp, SMCC | Calponin 1, basic, smooth muscle |
| CNTF | HCNTF | Ciliary neurotrophic factor |
| COL11A1 | CO11A1, COLL6, STL2 | Collagen, type XI, alpha 1 |
| COL17A1 | BP180, BPAG2 | Collagen, type XVII, alpha 1 |
| COL18A1 | KNO, KNO1, KS | Collagen, type XVIII, alpha 1 |
| COL1A1 | OI4 | Collagen, type I, alpha 1 |
| COL1A2 | OI4 | Collagen, type I, alpha 2 |
| COL4A2 | DKFZp686I14213, FLJ22259 | Collagen, type IV, alpha 2 |
| COL4A3 | | Collagen, type IV, alpha 3 (Goodpasture antigen) |
| COL4A4 | CA44 | Collagen, type IV, alpha 4 |
| COL4A5 | ASLN, ATS | Collagen, type IV, alpha 5 |
| COL6A1 | | Collagen, type VI, alpha 1 |
| COX17 | | COX17 cytochrome c oxidase copper chaperone |
| CP | | Ceruloplasmin (ferroxidase) |
| CRABP1 | CRABP, CRABP-I, CRABPI, RBP5 | Cellular retinoic acid binding protein 1 |
| CRADD | RAIDD | CASP2 and RIPK1 domain containing adaptor with death domain |
| CREBBP | CBP, KAT3A, RSTS, RTS | CREB binding protein |
| CRP | PTX1 | C-reactive protein, pentraxin-related |
| CRYAB | CRYA2, HSPB5 | Crystallin, alpha B |
| CSE1L | CAS, CSE1, XPO2 | CSE1 chromosome segregation 1-like (yeast) |
| CSF1 | M-CSF, MCSF, MGC31930 | Colony stimulating factor 1 (macrophage) |
| CSF1R | C-FMS, CD115, CSFR, FMS | Colony stimulating factor 1 receptor |
| CSF2 | GM-CSF, GMCSF | Colony stimulating factor 2 (granulocyte-macrophage) |
| CSF2RA | CD116, CSF2R | Colony stimulating factor 2 receptor, alpha, low-affinity (granulocyte-macrophage) |

TABLE 1-continued

| Gene | Gene synonym | Gene description |
|---|---|---|
| CSF3 | C17orf33, G-CSF, GCSF, MGC45931 | Colony stimulating factor 3 (granulocyte) |
| CSN1S1 | CASA, CSN1 | Casein alpha s1 |
| CSNK1E | CKIE, CKIepsilon, HCKIE | Casein kinase 1, epsilon |
| CSNK2A1 | | Casein kinase 2, alpha 1 polypeptide |
| CSNK2A2 | CSNK2A1 | Casein kinase 2, alpha prime polypeptide |
| CSNK2B | | Casein kinase 2, beta polypeptide |
| CST3 | | Cystatin C |
| CST6 | | Cystatin E/M |
| CSTA | STF1, STFA | Cystatin A (stefin A) |
| CSTB | CST6, EPM1, PME, STFB | Cystatin B (stefin B) |
| CTAG1A | ESO1, LAGE2A | Cancer/testis antigen 1A |
| CTAG1B | CT6.1, CTAG, CTAG1, ESO1, LAGE2A, LAGE2B, NY-ESO-1 | Cancer/testis antigen 1B |
| CTAG2 | CAMEL, CT6.2a, CT6.2b, ESO2, LAGE-1, LAGE-1a LAGE-1b, LAGE1, MGC138724, MGC3803 | Cancer/testis antigen 2 |
| CTGF | CCN2, IGFBP8 | Connective tissue growth factor |
| CTNNB1 | armadillo, beta-catenin, CTNNB | Catenin (cadherin-associated protein), beta 1, 88 kDa |
| CTNNBL1 | C20orf33, FLJ21108, NAP, NYD-SP19, P14, P14L | Catenin, beta like 1 |
| CTSB | | Cathepsin B |
| CTSD | CLN10, CPSD | Cathepsin D |
| CTSH | ACC-4, ACC-5, CPSB | Cathepsin H |
| CTSL | CTSL1, FLJ31037 | Cathepsin L |
| CUL2 | | Cullin 2 |
| CUL5 | VACM-1 | Cullin 5 |
| CXCL1 | FSP, GRO1, GROa, MGSA, MGSA-a, NAP-3, SCYB1 | Chemokine (C—X—C motif) ligand 1 (melanoma growth stimulating activity, alpha) |
| CXCL10 | C7, crg-2, gIP-10, IFI10, INP10, IP-10, mob-1, SCYB10 | Chemokine (C—X—C motif) ligand 10 |
| CXCL13 | ANGIE, ANGIE2, BCA-1 BLC, BLR1L, SCYB13 | Chemokine (C—X—C motif) ligand 13 |
| CXCL2 | CINC-2a, GRO2, GROb, MGSA-b, MIP-2a, SCYB2 | Chemokine (C—X—C motif) ligand 2 |
| CXCL5 | ENA-78, SCYB5 | Chemokine (C—X—C motif) ligand 5 |
| CXCL8 | 3-10C, AMCF-I, b-ENAP, GCP-1, GCP1, IL-8, IL8, K60, LECT, LUCT, LYNAP, MDNCF, MONAP, NAF, NAP-1, NAP1, SCYB8, TSG-1 | Chemokine (C—X—C motif) ligand 8 |
| CXCL9 | CMK, crg-10, Humig, MIG, SCYB9 | Chemokine (C—X—C motif) ligand 9 |
| CXCR1 | CD181, CDw128a, CKR-1 CMKAR1, IL8RA | Chemokine (C—X—C motif) receptor 1 |
| CXCR2 | CD182, CMKAR2, IL8RB | Chemokine (C—X—C motif) receptor 2 |
| CXCR4 | CD184, D2S201E, fusin, HM89, HSY3RR, LESTR, NPY3R, NPYR, NPYY3R | Chemokine (C—X—C motif) receptor 4 |
| CYB5R3 | DIA1 | Cytochrome b5 reductase 3 |
| CYP19A1 | ARO, ARO1, aromatase, CPV1, CYAR, CYP19, P-450AROM | Cytochrome P450, family 19, subfamily A, polypeptide 1 |
| CYP1A2 | CP12, P3-450 | Cytochrome P450, family 1, subfamily A, polypeptide 2 |
| CYP2C19 | CPCJ, CYP2C, P450IIC19 | Cytochrome P450, family 2, subfamily C, polypeptide 19 |
| CYP2E1 | CYP2E | Cytochrome P450, family 2, subfamily E, polypeptide 1 |
| CYP3A4 | CYP3A3 | Cytochrome P450, family 3, subfamily A, polypeptide 4 |
| CYP3A5 | CP35, P450PCN3, PCN3 | Cytochrome P450, family 3, subfamily A, polypeptide 5 |
| DAD1 | OST2 | Defender against cell death 1 |
| DAPK1 | DAPK | Death-associated protein kinase 1 |
| DAXX | DAP6 | Death-domain associated protein |
| DBI | ACBD1, ACBP | Diazepam binding inhibitor (GABA receptor modulator, acyl-CoA binding protein) |
| DCC | IGDCC1, NTN1R1 | DCC netrin 1 receptor |
| DCDC1 | | Doublecortin domain containing 1 |

TABLE 1-continued

| Gene | Gene synonym | Gene description |
|---|---|---|
| DCN | DSPG2, SLRR1B | Decorin |
| DDB2 | DDBB, FLJ34321, UV-DDB2 | Damage-specific DNA binding protein 2, 48 kDa |
| DDIT3 | CHOP, CHOP10, GADD153 | DNA-damage-inducible transcript 3 |
| DEFA1 | DEF1, DEFA2, HNP-1, MRS | Defensin, alpha 1 |
| DEFA1B | | Defensin, alpha 1B |
| DEFA3 | DEF3, FINP-3 | Defensin, alpha 3, neutrophil-specific |
| DEK | D6S231E | DEK proto-oncogene |
| DES | CMD1I, CSM1, CSM2 | Desmin |
| DHFR | | Dihydrofolate reductase |
| DIAPH3 | AN, AUNA1, DRF3, FLJ34705, NSDAN | Diaphanous-related formin 3 |
| DLC1 | ARHGAP7, DLC-1, HP, p122-RhoGAP, STARD12 | DLC1 Rho GTPase activating protein |
| DNAJC2 | MPHOSPH11, MPP11, ZRF1, ZUO1, zuotin | DnaJ (Hsp40) homolog, subfamily C, member 2 |
| DST | BP240, BPA, BPAG1, CATX-15, FLJ13425, FLJ21489, FLJ30627, FLJ32235, KIAA0728, MACF2 | Dystonin |
| DUSP1 | CL100, HVH1, MKP-1, PTPN10 | Dual specificity phosphatase 1 |
| DUSP14 | MKP-L, MKP6 | Dual specificity phosphatase 14 |
| DUSP4 | HVH2, MKP-2, TYP | Dual specificity phosphatase 4 |
| DVL3 | KIAA0208 | Dishevelled segment polarity protein 3 |
| DYNLL1 | DLC1, DLC8, DNCL1, hdlc1, LC8, PIN | Dynein, light chain, LC8-type 1 |
| DYRK2 | | Dual-specificity tyrosine-(Y)-phosphorylation regulated kinase 2 |
| E2F1 | RBBP3, RBP3 | E2F transcription factor 1 |
| E2F3 | | E2F transcription factor 3 |
| E2F5 | | E2F transcription factor 5, p130-binding |
| EBAG9 | EB9, RCAS1 | Estrogen receptor binding site associated, antigen, 9 |
| EDN1 | ET1 | Endothelin 1 |
| EEF2 | EEF-2, EF2 | Eukaryotic translation elongation factor 2 |
| EFNA1 | ECKLG, EPLG1, LERK1, TNFAIP4 | Ephrin-A1 |
| EFNA2 | ELF-1, EPLG6, LERK6 | Ephrin-A2 |
| EFNA5 | AF1, EPLG7, LERK7 | Ephrin-A5 |
| EFNB1 | CFNS, Elk-L, EPLG2, LERK2 | Ephrin-B1 |
| EFNB2 | EPLG5, Htk-L, HTKL, LERK5, MGC126226, MGC126227, MGC126228 | Ephrin-B2 |
| EFNB3 | EPLG8, LERK-8 | Ephrin-B3 |
| EGF | | Epidermal growth factor |
| EGFR | ERBB, ERBB1 | Epidermal growth factor receptor |
| EGR1 | AT225, G0S30, KROX-24, NGFI-A, TIS8, ZIF-268, ZNF225 | Early growth response 1 |
| EI24 | EPG4, PIG8, TP53I8 | Etoposide induced 2.4 |
| EIF3H | eIF3-gamma, eIF3-p40, eIF3h, EIF3S3 | Eukaryotic translation initiation factor 3, subunit H |
| EIF4E | EIF4E1, EIF4EL1, EIF4F | Eukaryotic translation initiation factor 4E |
| EIF4EBP1 | 4E-BP1, PHAS-I | Eukaryotic translation initiation factor 4E binding protein 1 |
| EIF4G1 | EIF4F, EIF4G, p220, PARK18 | Eukaryotic translation initiation factor 4 gamma, 1 |
| EIF4H | KIAA0038, WBSCR1, WSCR1 | Eukaryotic translation initiation factor 4H |
| EIF5A | EIF-5A, EIF5A1, MGC104255, MGC99547 | Eukaryotic translation initiation factor 5A |
| ELANE | ELA2, HLE, HNE, NE | Elastase, neutrophil expressed |
| ELK3 | ERP, NET, SAP2 | ELK3, ETS-domain protein (SRF accessory protein 2) |
| ENC1 | ENC-1, KLHL37, NRPB, PIG10, TP53I10 | Ectodermal-neural cortex 1 (with BTB domain) |
| ENG | CD105, END, HHT1, ORW, ORW1 | Endoglin |
| ENO1 | ENO1L1, MBP-1, MPB1, PPH | Enolase 1, (alpha) |

TABLE 1-continued

| Gene | Gene synonym | Gene description |
|---|---|---|
| ENO2 | | Enolase 2 (gamma, neuronal) |
| ENPP2 | ATX, PD-IALPHA, PDNP2 | Ectonucleotide pyrophosphatase/phosphodiesterase 2 |
| EPAS1 | bHLHe73, HIF2A, HLF, MOP2, PASD2 | Endothelial PAS domain protein 1 |
| EPCAM | 17-1A, 323/A3, CD326, CO-17A, EGP-2, EGP34, EGP40, Ep-CAM, ESA, GA733-2, HEA125, KS1/4, KSA, Ly74, M4S1, MH99, MIC18, MK-1, MOC31, TACST-1, TACSTD1, TROP1 | Epithelial cell adhesion molecule |
| EPHA1 | EPH, EPHT, EPHT1 | EPH receptor A1 |
| EPHA2 | ECK | EPH receptor A2 |
| EPHA3 | ETK, ETK1, HEK, HEK4, TYRO4 | EPH receptor A3 |
| EPHA4 | Hek8, TYRO1 | EPH receptor A4 |
| EPHA7 | Hek11 | EPH receptor A7 |
| EPHA8 | EEK, Hek3 | EPH receptor A8 |
| EPHB2 | DRT, EPHT3, ERK, Hek5, Tyro5 | EPH receptor B2 |
| EPHB3 | ETK2, Hek2, Tyro6 | EPH receptor B3 |
| EPHB4 | HTK, Tyro11 | EPH receptor B4 |
| EPHX1 | EPHX | Epoxide hydrolase 1, microsomal (xenobiotic) |
| EPO | EP | Erythropoietin |
| EPOR | | Erythropoietin receptor |
| ERBB2 | CD340, HER-2, HER2, NEU, NGL | V-erb-b2 avian erythroblastic leukemia viral oncogene homolog 2 |
| ERBB3 | HER3, LCCS2 | V-erb-b2 avian erythroblastic leukemia viral oncogene homolog 3 |
| ERBB4 | ALS19 | V-erb-b2 avian erythroblastic leukemia viral oncogene homolog 4 |
| ERCC1 | RAD10 | Excision repair cross-complementation group 1 |
| ERCC2 | EM9, MAG, MGC102762, MGC126218, MGC126219, TFIIH, XPD | Excision repair cross-complementation group 2 |
| ERCC3 | BTF2, GTF2H, RAD25, TFIIH, XPB | Excision repair cross-complementation group 3 |
| ERCC4 | FANCQ, RAD1, XPF | Excision repair cross-complementation group 4 |
| ERCC5 | ERCM2, XPGC | Excision repair cross-complementation group 5 |
| ERCC6 | ARMD5, CKN2, CSB, RAD26 | Excision repair cross-complementation group 6 |
| ESR1 | Era, ESR, NR3A1 | Estrogen receptor 1 |
| ESR2 | Erb, NR3A2 | Estrogen receptor 2 (ER beta) |
| ETHE1 | HSCO, YF13H12 | Ethylmalonic encephalopathy 1 |
| ETV4 | E1A-F, E1AF, PEA3 | Ets variant 4 |
| ETV5 | ERM | Ets variant 5 |
| EXT1 | LGCR, LGS, ttv | Exostosin glycosyltransferase 1 |
| EZH2 | ENX-1, EZH1, KMT6, KMT6A | Enhancer of zeste 2 polycomb repressive complex 2 subunit |
| EZR | VIL2 | Ezrin |
| F13A1 | F13A | Coagulation factor XIII, A1 polypeptide |
| F13B | FXIIIB | Coagulation factor XIII, B polypeptide |
| F2 | | Coagulation factor II (thrombin) |
| F3 | CD142 | Coagulation factor III (thromboplastin, tissue factor) |
| FABP1 | L-FABP | Fatty acid binding protein 1, liver |
| FABP2 | I-FABP | Fatty acid binding protein 2, intestinal |
| FABP4 | A-FABP, aP2 | Fatty acid binding protein 4, adipocyte |
| FABP5 | E-FABP, KFABP, PA-FABP | Fatty acid binding protein 5 (psoriasis-associated) |
| FADD | GIG3, MORT1 | Fas (TNFRSF6)-associated via death domain |
| FAF1 | CGI-03, hFAF1, HTAF1s, UBXD12, UBXN3A | Fas (TNFRSF6) associated factor 1 |
| FAM129A | C1orf24, GIG39, NIBAN | Family with sequence similarity 129, member A |
| FAP | DPPIV | Fibroblast activation protein, alpha |
| FAS | APO-1, APT1, CD95, FAS1, TNFRSF6 | Fas cell surface death receptor |
| FASLG | APT1LG1, CD178, FasL, TNFSF6 | Fas ligand (TNF superfamily, member 6) |

TABLE 1-continued

| Gene | Gene synonym | Gene description |
|---|---|---|
| FASN | FAS, SDR27X1 | Fatty acid synthase |
| FBXO6 | FBG2, FBS2, FBX6, Fbx6b | F-box protein 6 |
| FCER2 | CD23, CD23A, CLEC4J, FCE2 | Fc fragment of IgE, low affinity II, receptor for (CD23) |
| FEN1 | FEN-1, MF1, RAD2 | Flap structure-specific endonuclease 1 |
| FES | FPS | FES proto-oncogene, tyrosine kinase |
| FGA | | Fibrinogen alpha chain |
| FGB | | Fibrinogen beta chain |
| FGF1 | AFGF, ECGF, ECGF-beta, ECGFA, ECGFB, FGF-alpha, FGFA, GLIO703, HBGF1 | Fibroblast growth factor 1 (acidic) |
| FGF17 | FGF-13 | Fibroblast growth factor 17 |
| FGF18 | FGF-18, ZFGF5 | Fibroblast growth factor 18 |
| FGF19 | | Fibroblast growth factor 19 |
| FGF2 | FGFB | Fibroblast growth factor 2 (basic) |
| FGF23 | | Fibroblast growth factor 23 |
| FGF3 | HBGF-3, INT2 | Fibroblast growth factor 3 |
| FGF4 | HBGF-4, HST, HST-1, HSTF1, K-FGF, KFGF | Fibroblast growth factor 4 |
| FGF6 | | Fibroblast growth factor 6 |
| FGF7 | KGF | Fibroblast growth factor 7 |
| FGF8 | AIGF | Fibroblast growth factor 8 (androgen-induced) |
| FGF9 | | Fibroblast growth factor 9 |
| FGFR1 | BFGFR, CD331, CEK, FLG, FLT2, H2, H3, H4, H5, KAL2, N-SAM | Fibroblast growth factor receptor 1 |
| FGFR2 | BEK, CD332, CEK3, CFD1, ECT1, JWS, K-SAM, KGFR, TK14, TK25 | Fibroblast growth factor receptor 2 |
| FGFR3 | ACH, CD333, CEK2, JTK4 | Fibroblast growth factor receptor 3 |
| FGFR4 | CD334, JTK2 | Fibroblast growth factor receptor 4 |
| FGG | | Fibrinogen gamma chain |
| FHIT | AP3Aase, FRA3B | Fragile histidine triad |
| FIGF | VEGF-D, VEGFD | C-fos induced growth factor (vascular endothelial growth factor D) |
| FKBP5 | FKBP51, FKBP54, P54, PPIase, Ptg-10 | FK506 binding protein 5 |
| FKBP8 | FKBP38, FKBPr38 | FK506 binding protein 8, 38 kDa |
| FLT1 | FLT, VEGFR1 | Fms-related tyrosine kinase 1 |
| FLT4 | PCL, VEGFR3 | Fms-related tyrosine kinase 4 |
| FMO5 | | Flavin containing monooxygenase 5 |
| FN1 | CIG, FINC, GFND2, LETS, MSF | Fibronectin 1 |
| FOLH1 | FOLH, GCP2, GCPII, NAALAD1, NAALAdase, PSM, PSMA | Folate hydrolase (prostate-specific membrane antigen) 1 |
| FOS | AP-1, c-fos | FBJ murine osteosarcoma viral oncogene homolog |
| FOSL1 | fra-1 | FOS-like antigen 1 |
| FOXJ1 | FKHL13, HFH-4, HFH4 | Forkhead box J1 |
| FOXM1 | FKHL16, HFH-11, HNF-3, INS-1, MPHOSPH2, MPP2, TGT3, trident | Forkhead box M1 |
| FOXO1 | FKH1, FKHR, FOXO1A | Forkhead box O1 |
| FOXO3 | AF6q21, FKHRL1, FOXO2, FOXO3A | Forkhead box O3 |
| FOXQ1 | HFH1 | Forkhead box Q1 |
| FSCN1 | FLJ38511, p55, SNL | Fascin actin-bundling protein 1 |
| FSHB | | Follicle stimulating hormone, beta polypeptide |
| FST | FS | Follistatin |
| FTH1 | FHC, FTH, FTHL6, PIG15, PLIF | Ferritin, heavy polypeptide 1 |
| FTL | MGC71996, NBIA3 | Ferritin, light polypeptide |
| FZD1 | DKFZp564G072 | Frizzled class receptor 1 |
| FZD2 | | Frizzled class receptor 2 |
| G6PD | G6PD1 | Glucose-6-phosphate dehydrogenase |
| GADD45A | DDIT1, GADD45 | Growth arrest and DNA-damage-inducible, alpha |
| GADD45G | CR6, DDIT2, GADD45gamma, GRP17 | Growth arrest and DNA-damage-inducible, gamma |
| GAS1 | | Growth arrest-specific 1 |
| GAST | GAS | Gastrin |
| GATA3 | HDR | GATA binding protein 3 |
| GCLM | GLCLR | Glutamate-cysteine ligase, modifier subunit |

TABLE 1-continued

| Gene | Gene synonym | Gene description |
|---|---|---|
| GDF15 | MIC-1, MIC1, NAG-1, PDF, PLAB, PTGFB | Growth differentiation factor 15 |
| GDNF | ATF1, ATF2, HFB1-GDNF | Glial cell derived neurotrophic factor |
| GH1 | GH, GH-N, GHN, hGH-N | Growth hormone 1 |
| GH2 | GH-V, GH2, GHL, GHV, hGH-V | Growth hormone 2 |
| GJA1 | CX43, GJAL, ODD, ODDD, ODOD, SDTY3 | Gap junction protein, alpha 1, 43 kDa |
| GJB5 | CX31.1 | Gap junction protein, beta 5, 31.1 kDa |
| GLO1 | GLOD1 | Glyoxalase I |
| GMNN | Gem | Geminin, DNA replication inhibitor |
| GNAS | GNAS1, GNASXL, GPSA, NESP, NESP55, SCG6 | GNAS complex locus |
| GPA33 | A33 | Glycoprotein A33 (transmembrane) |
| GPC3 | DGSX, OCI-5, SDYS, SGB, SGBS, SGBS1 | Glypican 3 |
| GPI | AMF, NLK | Glucose-6-phosphate isomerase |
| GPX1 | | Glutathione peroxidase 1 |
| GPX2 | GSHPX-GI | Glutathione peroxidase 2 (gastrointestinal) |
| GRB10 | | Growth factor receptor-bound protein 10 |
| GRB2 | NCKAP2 | Growth factor receptor-bound protein 2 |
| GRB7 | | Growth factor receptor-bound protein 7 |
| GSK3A | | Glycogen synthase kinase 3 alpha |
| GSN | DKFZp313L0718 | Gelsolin |
| GSR | | Glutathione reductase |
| GSTM1 | GST1, H-B, MU | Glutathione S-transferase mu 1 |
| GSTM3 | GST5 | Glutathione S-transferase mu 3 (brain) |
| GSTP1 | FAEES3, GST3, GSTP | Glutathione S-transferase pi 1 |
| HDAC10 | DKFZP761B039 | Histone deacetylase 10 |
| HDAC2 | RPD3, YAF1 | Histone deacetylase 2 |
| HDAC5 | FLJ90614, KIAA0600, NY-CO-9 | Histone deacetylase 5 |
| HGF | DFNB39, F-TCF, HGFB, HPTA, SF | Hepatocyte growth factor (hepapoietin A; scatter factor) |
| HGFAC | HGFA, HGFAP | HGF activator |
| HIF1A | bHLHe78, HIF-1alpha, HIF1, MOP1, PASD8 | Hypoxia inducible factor 1, alpha subunit (basic helix-loop-helix transcription factor) |
| HIP1R | FLJ14000, HIP12, HIP3, ILWEQ, KIAA0655 | Huntingtin interacting protein 1 related |
| HIST1H2AC | H2AFL | Histone cluster 1, H2ac |
| HK1 | | Hexokinase 1 |
| HK2 | | Hexokinase 2 |
| HLA-G | | Major histocompatibility complex, class I, G |
| HMGA1 | HMGIY | High mobility group AT-hook 1 |
| HMGA2 | BABL, HMGIC, LIPO | High mobility group AT-hook 2 |
| HMOX1 | bK286B10, HO-1 | Heme oxygenase (decycling) 1 |
| HOXA5 | HOX1, HOX1C | Homeobox A5 |
| HOXA9 | HOX1, HOX1G | Homeobox A9 |
| HP | | Haptoglobin |
| HPGD | SDR36C1 | Hydroxyprostaglandin dehydrogenase 15-(NAD) |
| HPN | TMPRSS1 | Hepsin |
| HRAS | HRAS1 | Harvey rat sarcoma viral oncogene homolog |
| HSF1 | HSTF1 | Heat shock transcription factor 1 |
| HSP90AA1 | FLJ31884, Hsp89, Hsp90, HSP90N, HSPC1, HSPCA | Heat shock protein 90 kDa alpha (cytosolic), class A member 1 |
| HSP90AB1 | HSPC2, HSPCB | Heat shock protein 90 kDa alpha (cytosolic), class B member 1 |
| HSP90B1 | GP96, GRP94, TRA1 | Heat shock protein 90 kDa beta (Grp94), member 1 |
| HSPA1A | HSP70-1, HSPA1 | Heat shock 70 kDa protein 1A |
| HSPA1B | HSP70-2 | Heat shock 70 kDa protein 1B |
| HSPA1L | HSP70-HOM, hum70t | Heat shock 70 kDa protein 1-like |
| HSPA2 | | Heat shock 70 kDa protein 2 |
| HSPA4 | HS24/P52, HSPH2 | Heat shock 70 kDa protein 4 |
| HSPA8 | HSC70, HSC71, HSP73, HSPA10 | Heat shock 70 kDa protein 8 |
| HSPB1 | Hs.76067, Hsp25, HSP27, HSP28 | Heat shock 27 kDa protein 1 |
| HSPD1 | GROEL, HSP60, SPG13 | Heat shock 60 kDa protein 1 (chaperonin) |

TABLE 1-continued

| Gene | Gene synonym | Gene description |
| --- | --- | --- |
| HSPE1 | CPN10, GROES | Heat shock 10 kDa protein 1 |
| HSPH1 | HSP105A, HSP105B, KIAA0201, NY-CO-25 | Heat shock 105 kDa/110 kDa protein 1 |
| IBSP | BSP, BSP-II, SP-II | Integrin-binding sialoprotein |
| ICAM1 | BB2, CD54 | Intercellular adhesion molecule 1 |
| ID1 | bHLHb24, dJ857M17.1.2 | Inhibitor of DNA binding 1, dominant negative helix-loop-helix protein |
| ID2 | bHLHb26, GIG8 | Inhibitor of DNA binding 2, dominant negative helix-loop-helix protein |
| ID3 | bHLHb25, HEIR-1 | Inhibitor of DNA binding 3, dominant negative helix-loop-helix protein |
| IDO1 | IDO, INDO | Indoleamine 2,3-dioxygenase 1 |
| IFNA1 | IFL, IFN, IFN-ALPHA, IFN-alphaD, IFNA13, IFNA@ | Interferon, alpha 1 |
| IFNA13 | | Interferon, alpha 13 |
| IFNAR1 | IFNAR, IFRC | Interferon (alpha, beta and omega) receptor 1 |
| IFNAR2 | IFNABR | Interferon (alpha, beta and omega) receptor 2 |
| IFNB1 | IFB, IFF, IFNB | Interferon, beta 1, fibroblast |
| IFNG | | Interferon, gamma |
| IGF1 | IGF-1, IGF1A, IGFI | Insulin-like growth factor 1 (somatomedin C) |
| IGF1R | CD221, IGFIR, IGFR, JTK13, MGC18216 | Insulin-like growth factor 1 receptor |
| IGF2 | C11orf43, FLJ44734, IGF-II | Insulin-like growth factor 2 |
| IGF2R | CD222, CIMPR, M6P-R, MPR1, MPRI | Insulin-like growth factor 2 receptor |
| IGFBP2 | IBP2 | Insulin-like growth factor binding protein 2, 36 kDa |
| IGFBP3 | BP-53, IBP3 | Insulin-like growth factor binding protein 3 |
| IL10 | CSIF, IL-10, IL10A, TGIF | Interleukin 10 |
| IL11 | AGIF, IL-11 | Interleukin 11 |
| IL12A | CLMF, IL-12A, NFSK, NKSF1, p35 | Interleukin 12A |
| IL13 | ALRH, BHR1, IL-13, MGC116786, MGC116788, MGC116789, P600 | Interleukin 13 |
| IL13RA2 | CD213a2, CT19, IL-13R, IL13BP | Interleukin 13 receptor, alpha 2 |
| IL15 | IL-15, MGC9721 | Interleukin 15 |
| IL16 | FLJ16806, FLJ42735, HsT19289, IL-16, LCF, prIL-16 | Interleukin 16 |
| IL17A | CTLA8, IL-17, IL-17A, IL17 | Interleukin 17A |
| IL17B | IL-17B, IL-20, MGC138900, MGC138901, NIRF, ZCYTO7 | Interleukin 17B |
| IL18 | IGIF, IL-18, IL-1g, IL1F4 | Interleukin 18 |
| IL1A | IL-1A, IL1, IL1-ALPHA, IL1F1 | Interleukin 1, alpha |
| IL1B | IL-1B, IL1-BETA, IL1F2 | Interleukin 1, beta |
| IL1R1 | CD121A, D2S1473, IL1R, IL1RA | Interleukin 1 receptor, type I |
| IL1R2 | CD121b, IL1RB | Interleukin 1 receptor, type II |
| IL1RN | ICIL-1RA, IL-1RN, IL1F3, IL1RA, IRAP, MGC10430 | Interleukin 1 receptor antagonist |
| IL2 | IL-2, TCGF | Interleukin 2 |
| IL24 | C49A, FISP, IL-24, IL10B mda-7, Mob-5, ST16 | Interleukin 24 |
| IL2RA | CD25, IDDM10, IL2R | Interleukin 2 receptor, alpha |
| IL2RB | CD122, IL15RB | Interleukin 2 receptor, beta |
| IL2RG | CD132, CIDX, IMD4, SCIDX1 | Interleukin 2 receptor, gamma |
| IL4 | BCGF-1, BCGF1, BSF1, IL-4, MGC79402 | Interleukin 4 |
| IL4R | CD124 | Interleukin 4 receptor |
| IL5 | EDF, IL-5, TRF | Interleukin 5 |
| IL6 | BSF2, HGF, HSF, IFNB2, IL-6 | Interleukin 6 |
| IL6R | CD126 | Interleukin 6 receptor |
| IL6ST | CD130, GP130 | Interleukin 6 signal transducer |
| IL7 | IL-7 | Interleukin 7 |
| IL9 | HP40, IL-9, P40 | Interleukin 9 |

TABLE 1-continued

| Gene | Gene synonym | Gene description |
|---|---|---|
| ILF3 | DRBP76, MPHOSPH4, MPP4, NF90, NFAR-1 | Interleukin enhancer binding factor 3, 90 kDa |
| ILK | | Integrin-linked kinase |
| INHBA | | Inhibin, beta A |
| INHBB | | Inhibin, beta B |
| INS | IDDM1, IDDM2 | Insulin |
| IRF1 | MAR | Interferon regulatory factor 1 |
| IRF4 | LSIRF, MUM1 | Interferon regulatory factor 4 |
| ITGA1 | CD49a, VLA1 | Integrin, alpha 1 |
| ITGA2 | CD49B | Integrin, alpha 2 (CD49B, alpha 2 subunit of VLA-2 receptor) |
| ITGA2B | CD41, CD41B, GP2B, PPP1R93 | Integrin, alpha 2b (platelet glycoprotein IIb of IIb/IIIa complex, antigen CD41) |
| ITGA3 | CD49c, GAP-B3, MSK18, VCA-2, VLA3a | Integrin, alpha 3 (antigen CD49C, alpha 3 subunit of VLA-3 receptor) |
| ITGA4 | CD49D | Integrin, alpha 4 (antigen CD49D, alpha 4 subunit of VLA-4 receptor) |
| ITGA5 | CD49e, FNRA | Integrin, alpha 5 (fibronectin receptor, alpha polypeptide) |
| ITGA6 | CD49f | Integrin, alpha 6 |
| ITGAM | CD11B, CR3A, MAC-1 | Integrin, alpha M (complement component 3 receptor 3 subunit) |
| ITGAV | CD51, MSK8, VNRA, VTNR | Integrin, alpha V |
| ITGB1 | CD29, FNRB, GPIIA, MDF2, MSK12 | Integrin, beta 1 (fibronectin receptor, beta polypeptide, antigen CD29 includes MDF2, MSK12) |
| ITGB3 | CD61, GP3A, GPIIIa | Integrin, beta 3 (platelet glycoprotein IIIa, antigen CD61) |
| ITGB4 | CD104 | Integrin, beta 4 |
| ITGB5 | | Integrin, beta 5 |
| ITGB6 | | Integrin, beta 6 |
| ITGB8 | | Integrin, beta 8 |
| ITIH4 | H4P, IHRP, ITIHL1 | Inter-alpha-trypsin inhibitor heavy chain family, member 4 |
| JKAMP | C14orf100, CDA06, HSPC213, HSPC327, JAMP | JNK1/MAPK8-associated membrane protein |
| JTB | hJT | Jumping translocation breakpoint |
| JUN | AP-1, c-Jun | Jun proto-oncogene |
| JUND | AP-1 | Jun D proto-oncogene |
| JUP | CTNNG, DP3, DPIII, PDGB, PKGB | Junction plakoglobin |
| KAT2B | GCN5, GCN5L, P/CAF, PCAF | K(lysine) acetyltransferase 2B |
| KDR | CD309, FLK1, VEGFR, VEGFR2 | Kinase insert domain receptor (a type III receptor tyrosine kinase) |
| KIF2A | HK2, KIF2 | Kinesin heavy chain member 2A |
| KIF2C | CT139, KNSL6, MCAK | Kinesin family member 2C |
| KISS1 | | KiSS-1 metastasis-suppressor |
| KIT | C-Kit, CD117, PBT, SCFR | V-kit Hardy-Zuckerman 4 feline sarcoma viral oncogene homolog |
| KITLG | FPH2, Kitl, KL-1, MGF, SCF, SF | KIT ligand |
| KLF4 | EZF, GKLF | Kruppel-like factor 4 (gut) |
| KLF5 | BTEB2, CKLF, IKLF | Kruppel-like factor 5 (intestinal) |
| KLK10 | NES1, PRSSL1 | Kallikrein-related peptidase 10 |
| KLK11 | PRSS20, TLSP | Kallikrein-related peptidase 11 |
| KLK13 | KLK-L4 | Kallikrein-related peptidase 13 |
| KLK14 | KLK-L6 | Kallikrein-related peptidase 14 |
| KLK15 | ACO, HSRNASPH, prostinogen | Kallikrein-related peptidase 15 |
| KLK2 | | Kallikrein-related peptidase 2 |
| KLK3 | APS, PSA | Kallikrein-related peptidase 3 |
| KLK4 | EMSP, EMSP1, KLK-L1, PRSS17, PSTS | Kallikrein-related peptidase 4 |
| KLK5 | KLK-L2, SCTE | Kallikrein-related peptidase 5 |
| KLK6 | Bssp, Klk7, neurosin, PRSS18, PRSS9 | Kallikrein-related peptidase 6 |
| KLK7 | PRSS6, SCCE | Kallikrein-related peptidase 7 |
| KLK8 | HNP, neuropsin, ovasin, PRSS19, TADG14 | Kallikrein-related peptidase 8 |
| KLRK1 | CD314, D12S2489E, KLR, NKG2-D, NKG2D | Killer cell lectin-like receptor subfamily K, member 1 |
| KRAS | KRAS1, KRAS2 | Kirsten rat sarcoma viral oncogene homolog |
| KRT13 | CK13, K13, MGC161462, MGC3781 | Keratin 13 |

TABLE 1-continued

| Gene | Gene synonym | Gene description |
|---|---|---|
| KRT14 | EBS3, EBS4 | Keratin 14 |
| KRT15 | CK15, K15, K1CO | Keratin 15 |
| KRT17 | PCHC1 | Keratin 17 |
| KRT18 | | Keratin 18 |
| KRT19 | CK19, K19, K1CS, MGC15366 | Keratin 19 |
| KRT4 | CK4, CYK4, K4 | Keratin 4 |
| KRT8 | CARD2, CK8, CYK8, K2C8, K8, KO | Keratin 8 |
| LALBA | LYZL7 | Lactalbumin, alpha- |
| LAMB1 | CLM | Laminin, beta 1 |
| LAMC1 | LAMB2 | Laminin, gamma 1 (formerly LAMB2) |
| LCN1 | MGC71975, PMFA, TLC, TP, VEGP | Lipocalin 1 |
| LDHA | | Lactate dehydrogenase A |
| LEP | OB, OBS | Leptin |
| LGALS3 | GALIG, LGALS2, MAC-2 | Lectin, galactoside-binding, soluble, 3 |
| LGALS3BP | 90K, BTBD17B, CyCAP, gp90, M2BP, MAC-2-BP, TANGO10B | Lectin, galactoside-binding, soluble, 3 binding protein |
| LGALS4 | GAL4 | Lectin, galactoside-binding, soluble, 4 |
| LGI1 | EPITEMPIN, EPT, ETL1, IB1099 | Leucine-rich, glioma inactivated 1 |
| LGMN | LGMN1, PRSC1 | Legumain |
| LHB | CGB4, hLHB, LSH-B | Luteinizing hormone beta polypeptide |
| LHX1 | LIM-1, LIM1 | LIM homeobox 1 |
| LIF | CDF, DIA, HILDA | Leukemia inhibitory factor |
| LIG4 | | Ligase IV, DNA, ATP-dependent |
| LIMK1 | LIMK | LIM domain kinase 1 |
| LMNA | CMD1A, HGPS, LGMD1B, LMN1, LMNL1, PRO1 | Lamin A/C |
| LRP1B | LRP-DIT, LRPDIT | Low density lipoprotein receptor-related protein 1B |
| LRP6 | ADCAD2 | Low density lipoprotein receptor-related protein 6 |
| LTA | LT, TNFB, TNFSF1 | Lymphotoxin alpha |
| LTA4H | | Leukotriene A4 hydrolase |
| LTB | p33, TNFC, TNFSF3 | Lymphotoxin beta (TNF superfamily, member 3) |
| LTBR | D12S370, TNF-R-III, TNFCR, TNFR-RP, TNFR2-RP, TNFRSF3 | Lymphotoxin beta receptor (TNFR superfamily, member 3) |
| LTF | HLF2 | Lactotransferrin |
| MAD2L1 | HSMAD2, MAD2 | MAD2 mitotic arrest deficient-like 1 (yeast) |
| MAD2L2 | MAD2B, POLZ2, REV7 | MAD2 mitotic arrest deficient-like 2 (yeast) |
| MAGEA3 | CT1.3, HIP8, HYPD, MAGE3, MGC14613 | Melanoma antigen family A, 3 |
| MAGEA4 | CT1.4, MAGE-41, MAGE-X2, MAGE4, MAGE4A, MAGE4B, MGC21336 | Melanoma antigen family A, 4 |
| MAGEA6 | CT1.6, MAGE6 | Melanoma antigen family A, 6 |
| MAGEB5 | CT3.3, MAGE-B5 | Melanoma antigen family B, 5 |
| MAGEB6 | CT3.4, FLJ40242, MAGE-B6, MAGEB6A | Melanoma antigen family B, 6 |
| MAGEC1 | CT7, CT7.1, MAGE-C1, MGC39366 | Melanoma antigen family C, 1 |
| MAGEC2 | CT10, MAGE-C2, MAGEE1 | Melanoma antigen family C, 2 |
| MAGEC3 | CT7.2, HCA2, MAGE-C3 | Melanoma antigen family C, 3 |
| MAGED1 | DLXIN-1, NRAGE | Melanoma antigen family D, 1 |
| MAGED2 | 11B6, BCG1, HCA10, JCL-1, MAGE-D2, MAGED, MGC8386 | Melanoma antigen family D, 2 |
| MAGI1 | AIP3, BAIAP1, BAP1, MAGI-1, TNRC19, WWP3 | Membrane associated guanylate kinase, WW and PDZ domain containing 1 |
| MAP2K1 | MAPKK1, MEK1, PRKMK1 | Mitogen-activated protein kinase kinase 1 |
| MAP2K2 | MEK2, PRKMK2 | Mitogen-activated protein kinase kinase 2 |
| MAP2K4 | JNKK1, MEK4, MKK4, PRKMK4, SERK1 | Mitogen-activated protein kinase kinase 4 |
| MAPK1 | ERK, ERK2, MAPK2, p41mapk, PRKM1, PRKM2 | Mitogen-activated protein kinase 1 |
| MAPK14 | CSBP1, CSBP2, CSPB1, Mxi2, p38, PRKM14, PRKM15 | Mitogen-activated protein kinase 14 |

TABLE 1-continued

| Gene | Gene synonym | Gene description |
|---|---|---|
| MAPK3 | ERK1, p44erk1, p44mapk, PRKM3 | Mitogen-activated protein kinase 3 |
| MAPK7 | BMK1, ERK5, PRKM7 | Mitogen-activated protein kinase 7 |
| MAPK8 | JNK, JNK1, PRKM8, SAPK1 | Mitogen-activated protein kinase 8 |
| MAPKAPK2 | | Mitogen-activated protein kinase-activated protein kinase 2 |
| MBD1 | CXXC3, PCM1 | Methyl-CpG binding domain protein 1 |
| MBD2 | | Methyl-CpG binding domain protein 2 |
| MBD4 | MED1 | Methyl-CpG binding domain protein 4 |
| MCL1 | BCL2L3, Mcl-1 | Myeloid cell leukemia 1 |
| MCM2 | BM28, CCNL1, cdc19, CDCL1, D3S3194, KIAA0030 | Minichromosome maintenance complex component 2 |
| MCM3 | | Minichromosome maintenance complex component 3 |
| MCM5 | CDC46 | Minichromosome maintenance complex component 5 |
| MCM7 | CDC47, MCM2, PPP1R104 | Minichromosome maintenance complex component 7 |
| MDH1 | | Malate dehydrogenase 1, NAD (soluble) |
| MDK | FLJ27379, MK, NEGF2 | Midkine (neurite growth-promoting factor 2) |
| MDM2 | HDM2, MGC5370 | MDM2 proto-oncogene, E3 ubiquitin protein ligase |
| MECP2 | MRX16, MRX79, RTT | Methyl CpG binding protein 2 |
| MED1 | CRSP1, CRSP200, DRIP230, PBP, PPARBP, PPARGBP, RB18A, TRAP220, TRIP2 | Mediator complex subunit 1 |
| MET | HGFR, RCCP2 | MET proto-oncogene, receptor tyrosine kinase |
| MFGE8 | BA46, EDIL1, hP47, HsT19888, MFG-E8, OAcGD3S, SED1, SPAG10 | Milk fat globule-EGF factor 8 protein |
| MGMT | | O-6-methylguanine-DNA methyltransferase |
| MIA | CD-RAP | Melanoma inhibitory activity |
| MIF | GIF, GLIF | Macrophage migration inhibitory factor (glycosylation-inhibiting factor) |
| MKI67 | MIB-, PPP1R105 | Marker of proliferation Ki-67 |
| MLH1 | COCA2, FCC2, HNPCC, HNPCC2 | MutL homolog 1 |
| MLLT11 | AF1Q | Myeloid/lymphoid or mixed-lineage leukemia (trithorax homolog, Drosophila); translocated to, 11 |
| MME | CALLA, CD10, NEP | Membrane metallo-endopeptidase |
| MMP1 | CLG | Matrix metallopeptidase 1 (interstitial collagenase) |
| MMP10 | STMY2 | Matrix metallopeptidase 10 (stromelysin 2) |
| MMP11 | STMY3 | Matrix metallopeptidase 11 (stromelysin 3) |
| MMP12 | HME | Matrix metallopeptidase 12 (macrophage elastase) |
| MMP13 | CLG3 | Matrix metallopeptidase 13 (collagenase 3) |
| MMP14 | MT1-MMP | Matrix metallopeptidase 14 (membrane-inserted) |
| MMP15 | MT2-MMP, MTMMP2, SMCP-2 | Matrix metallopeptidase 15 (membrane-inserted) |
| MMP16 | C8orf57, DKFZp761D112, MT3-MMP | Matrix metallopeptidase 16 (membrane-inserted) |
| MMP2 | CLG4, CLG4A, TBE-1 | Matrix metallopeptidase 2 (gelatinase A, 72 kDa gelatinase, 72 kDa type IV collagenase) |
| MMP3 | STMY, STMY1 | Matrix metallopeptidase 3 (stromelysin 1, progelatinase) |
| MMP7 | MPSL1, PUMP-1 | Matrix metallopeptidase 7 (matrilysin, uterine) |
| MMP8 | CLG1 | Matrix metallopeptidase 8 (neutrophil collagenase) |
| MMP9 | CLG4B | Matrix metallopeptidase 9 (gelatinase B, 92 kDa gelatinase, 92 kDa type IV collagenase) |

TABLE 1-continued

| Gene | Gene synonym | Gene description |
|---|---|---|
| MPO | | Myeloperoxidase |
| MRE11A | ATLD, MRE11 | MRE11 meiotic recombination 11 homolog A (*S. cerevisiae*) |
| MSH6 | GTBP | MutS homolog 6 |
| MSLN | CAK1, MPF | Mesothelin |
| MSMB | IGBF, MSP, MSPB, PN44, PRPS, PSP, PSP-94, PSP57, PSP94 | Microseminoprotein, beta- |
| MSR1 | CD204, SCARA1 | Macrophage scavenger receptor 1 |
| MT1A | MT1, MT1S | Metallothionein 1A |
| MT1G | MT1, MT1K | Metallothionein 1G |
| MTA1 | | Metastasis associated 1 |
| MUC1 | ADMCKD, ADMCKD1, CD227, MCD, MCKD, MCKD1, PEM, PUM | Mucin 1, cell surface associated |
| MUTYH | MYH | MutY homolog |
| MVP | LRP, VAULT1 | Major vault protein |
| MXI1 | hHI, Hc11, MAD2, MXD2 MXI | MAX interactor 1, dimerization protein |
| MYBL2 | B-MYB, BMYB | V-myb avian myeloblastosis viral oncogene homolog-like 2 |
| MYC | bHLHe39, c-Myc, MYCC | V-myc avian myelocytomatosis viral oncogene homolog |
| MYOCD | MYCD | Myocardin |
| MYOD1 | bHLHc1, MYF3, MYOD, PUM | Myogenic differentiation 1 |
| MYOG | bHLHc3, MYF4 | Myogenin (myogenic factor 4) |
| NAGA | D22S674 | N-acetylgalactosaminidase, alpha- |
| NAIP | BIRC1, NLRB1 | NLR family, apoptosis inhibitory protein |
| NAMPT | PBEF, PBEF1 | Nicotinamide phosphoribosyltransferase |
| NAT2 | AAC2 | N-acetyltransferase 2 (arylamine N-acetyltransferase) |
| NCAM1 | CD56, NCAM | Neural cell adhesion molecule 1 |
| NCOA3 | ACTR, AIB1, bHLHe42, CAGH16, KAT13B, p/CIP, RAC3, SRC-3, SRC3, TNRC16, TRAM-1 | Nuclear receptor coactivator 3 |
| NDRG1 | CAP43, DRG1, NDR1, RTP, TDD5 | N-myc downstream regulated 1 |
| NEDD8 | Nedd-8 | Neural precursor cell expressed, developmentally down-regulated 8 |
| NEO1 | HsT17534, IGDCC2, NGN, NTN1R2 | Neogenin 1 |
| NFKB1 | KBF1, NF-kappaB, NF-kB1, NFkappaB, NFKB-p50, p105, p50 | Nuclear factor of kappa light polypeptide gene enhancer in B-cells 1 |
| NFKB2 | LYT-10, NF-kB2, p105, p52 | Nuclear factor of kappa light polypeptide gene enhancer in B-cells 2 (p49/p100) |
| NFKBIA | IkappaBalpha, IKBA, MAD-3, NFKBI | Nuclear factor of kappa light polypeptide gene enhancer in B-cells inhibitor, alpha |
| NFKBIE | IKBE | Nuclear factor of kappa light polypeptide gene enhancer in B-cells inhibitor, epsilon |
| NGF | NGFB | Nerve growth factor (beta polypeptide) |
| NGFR | CD271, p75NTR, TNFRSF16 | Nerve growth factor receptor |
| NKX3-1 | BAPX2, NKX3.1, NKX3A | NK3 homeobox 1 |
| NME1 | NDPKA, NM23, NM23-H1 | NME/NM23 nucleoside diphosphate kinase 1 |
| NME2 | NDPKB, NM23-H2 | NME/NM23 nucleoside diphosphate kinase 2 |
| NOS1 | nNOS, NOS | Nitric oxide synthase 1 (neuronal) |
| NOS2 | HEP-NOS, iNOS, NOS, NOS2A | Nitric oxide synthase 2, inducible |
| NOS3 | ECNOS, eNOS | Nitric oxide synthase 3 (endothelial cell) |
| NOTCH1 | TAN1 | Notch 1 |
| NOTCH2 | | Notch 2 |
| NOTCH3 | CADASIL, CASIL | Notch 3 |
| NQO1 | DHQU, DIA4, DTD, NMOR1, QR1 | NAD(P)H dehydrogenase, quinone 1 |
| NR0B1 | AHC, AHCH, DAX1, DSS, NR0B1 | Nuclear receptor subfamily 0, group B, member 1 |

TABLE 1-continued

| Gene | Gene synonym | Gene description |
| --- | --- | --- |
| NRG1 | GGF, HGL, HRG, NDF, NRG1-IT2 | Neuregulin 1 |
| NRG2 | Don-1, HRG2, NTAK | Neuregulin 2 |
| NRG3 | | Neuregulin 3 |
| NRP1 | CD304, NRP, VEGF165R | Neuropilin 1 |
| NRP2 | VEGF165R2 | Neuropilin 2 |
| NTF3 | NGF2 | Neurotrophin 3 |
| NTF4 | GLC1O, NT-4/5, NTF5 | Neurotrophin 4 |
| NTHL1 | NTH1, OCTS3 | Nth endonuclease III-like 1 (*E. coli*) |
| NTN1 | NTN1L | Netrin 1 |
| NTRK1 | MTC, TRK, TRKA | Neurotrophic tyrosine kinase, receptor, type 1 |
| NTRK2 | TRKB | Neurotrophic tyrosine kinase, receptor, type 2 |
| NTRK3 | TRKC | Neurotrophic tyrosine kinase, receptor, type 3 |
| NUDT1 | MTH1 | Nudix (nucleoside diphosphate linked moiety X)-type motif 1 |
| NUMB | C14orf41 | Numb homolog (*Drosophila*) |
| OGG1 | HMMH, HOGG1, MUTM, OGH1 | 8-oxoguanine DNA glycosylase |
| OR51E2 | PSGR | Olfactory receptor, family 51, subfamily E, member 2 |
| ORM1 | | Orosomucoid 1 |
| OSM | MGC20461 | Oncostatin M |
| PAGE4 | CT16.7, GAGEC1, PAGE-4 | P antigen family, member 4 (prostate associated) |
| PAPPA | ASBABP2, DIPLA1, IGFBP-4ase, PAPA, PAPP-A, PAPPA1 | Pregnancy-associated plasma protein A, pappalysin 1 |
| PARP1 | ADPRT, PARP, PPOL | Poly (ADP-ribose) polymerase 1 |
| PARVB | CGI-56 | Parvin, beta |
| PAX5 | BSAP | Paired box 5 |
| PAX8 | | Paired box 8 |
| PCNA | | Proliferating cell nuclear antigen |
| PDGFA | PDGF-A, PDGF1 | Platelet-derived growth factor alpha polypeptide |
| PDGFB | SIS, SSV | Platelet-derived growth factor beta polypeptide |
| PDGFRA | CD140a, PDGFR2 | Platelet-derived growth factor receptor, alpha polypeptide |
| PDGFRB | CD140b, JTK12, PDGFR, PDGFR1 | Platelet-derived growth factor receptor, beta polypeptide |
| PDZD4 | FLJ34125, KIAA1444, LU1, PDZK4, PDZRN4L | PDZ domain containing 4 |
| PF4 | CXCL4, SCYB4 | Platelet factor 4 |
| PGC | | Progastricsin (pepsinogen C) |
| PGF | D12S1900, PGFL, PLGF, PlGF-2, SHGC-10760 | Placental growth factor |
| PGR | NR3C3, PR | Progesterone receptor |
| PHF20 | C20orf104, dJ1121G12.1, TDRD20A | PHD finger protein 20 |
| PIGR | | Polymeric immunoglobulin receptor |
| PIK3CA | PI3K | Phosphatidylinositol-4,5-bisphosphate 3-kinase, catalytic subunit alpha |
| PIK3R1 | GRB1, p85, p85-ALPHA | Phosphoinositide-3-kinase, regulatory subunit 1 (alpha) |
| PIK3R2 | p85, P85B | Phosphoinositide-3-kinase, regulatory subunit 2 (beta) |
| PIK3R3 | p55 | Phosphoinositide-3-kinase, regulatory subunit 3 (gamma) |
| PIM1 | PIM | Pim-1 proto-oncogene, serine/threonine kinase |
| PIM2 | | Pim-2 proto-oncogene, serine/threonine kinase |
| PIM3 | | Pim-3 proto-oncogene, serine/threonine kinase |
| PIN1 | dod | Peptidylprolyl cis/trans isomerase, NIMA-interacting 1 |
| PIP4K2B | PIP5K2B, PIP5KIIB, PIP5KIIbeta | Phosphatidylinositol-5-phosphate 4-kinase, type II, beta |
| PKM | OIP3, PK3, PKM2, THBP1 | Pyruvate kinase, muscle |
| PLAT | | Plasminogen activator, tissue |
| PLAU | UPA, URK | Plasminogen activator, urokinase |
| PLAUR | CD87, UPAR, URKR | Plasminogen activator, urokinase receptor |
| PLG | | Plasminogen |
| PLK1 | PLK | Polo-like kinase 1 |

TABLE 1-continued

| Gene | Gene synonym | Gene description |
| --- | --- | --- |
| PLP1 | GPM6C, PLP, SPG2 | Proteolipid protein 1 |
| PMEPA1 | STAG1, TMEPAI | Prostate transmembrane protein, androgen induced 1 |
| PML | MYL, RNF71, TRIM19 | Promyelocytic leukemia |
| PMP22 | GAS-3, HNPP, Sp110 | Peripheral myelin protein 22 |
| PNMT | PENT | Phenylethanolamine N-methyltransferase |
| POMC | ACTH, CLIP, LPH, MSH, NPP, POC | Proopiomelanocortin |
| PON1 | ESA, PON | Paraoxonase 1 |
| POSTN | OSF-2, periostin, PN | Periostin, osteoblast specific factor |
| POU2F2 | OCT2, OTF2 | POU class 2 homeobox 2 |
| PPA2 | FLJ20459 | Pyrophosphatase (inorganic) 2 |
| PPARG | NR1C3, PPARG1, PPARG2, PPARgamma | Peroxisome proliferator-activated receptor gamma |
| PPARGC1A | PGC1, PGC1A, PPARGC1 | Peroxisome proliferator-activated receptor gamma, coactivator 1 alpha |
| PPM1D | PP2C-DELTA, Wip1 | Protein phosphatase, Mg2+/Mn2+ dependent, 1D |
| PPP1R15A | GADD34 | Protein phosphatase 1, regulatory subunit 15A |
| PPY | PNP | Pancreatic polypeptide |
| PRDM13 | | PR domain containing 13 |
| PRDM16 | KIAA1675, MEL1, MGC166915, PFM13 | PR domain containing 16 |
| PRDX2 | MGC4104, NKEFB, PRP, PRX2, PRXII, TDPX1, TSA | Peroxiredoxin 2 |
| PRDX4 | AOE37-2 | Peroxiredoxin 4 |
| PRKCA | PKCA | Protein kinase C, alpha |
| PRKCB | PKCB, PRKCB1, PRKCB2 | Protein kinase C, beta |
| PRKCE | | Protein kinase C, epsilon |
| PRKCH | PKC-L, PKCL, PRKCL | Protein kinase C, eta |
| PRKCI | DXS1179E, PKCI | Protein kinase C, iota |
| PRKCQ | | Protein kinase C, theta |
| PRKDC | DNA-PKcs, DNAPK, DNPK1, HYRC, HYRC1, p350, XRCC7 | Protein kinase, DNA-activated, catalytic polypeptide |
| PRL | | Prolactin |
| PROC | | Protein C (inactivator of coagulation factors Va and VIIIa) |
| PRSS1 | TRY1 | Protease, serine, 1 (trypsin 1) |
| PSCA | | Prostate stem cell antigen |
| PSMD4 | AF, AF-1, Rpn10, S5A | Proteasome (prosome, macropain) 26S subunit, non-ATPase, 4 |
| PTCH1 | BCNS, NBCCS, PTCH | Patched 1 |
| PTCH2 | | Patched 2 |
| PTGS1 | COX1, PGHS-1, PTGHS | Prostaglandin-endoperoxide synthase 1 (prostaglandin G/H synthase and cyclooxygenase) |
| PTGS2 | COX2 | Prostaglandin-endoperoxide synthase 2 (prostaglandin G/H synthase and cyclooxygenase) |
| PTH | PTH1 | Parathyroid hormone |
| PTHLH | HHM, PLP, PTHR, PTHRP | Parathyroid hormone-like hormone |
| PTK2 | FADK, FAK, FAK1, PPP1R71 | Protein tyrosine kinase 2 |
| PTN | HBGF8, HBNF, NEGF1 | Pleiotrophin |
| PTPRO | GLEPP1, NPHS6, PTP-oc, PTP-U2, PTPU2 | Protein tyrosine phosphatase, receptor type, O |
| PTTG1 | EAP1, HPTTG, PTTG, securin, TUTR1 | Pituitary tumor-transforming 1 |
| PURA | PUR-ALPHA, PUR1, PURALPHA | Purine-rich element binding protein A |
| PZP | CPAMD6 | Pregnancy-zone protein |
| RAB11FIP3 | eferin, KIAA0665, Rab11-FIP3 | RAB11 family interacting protein 3 (class II) |
| RAB18 | | RAB18, member RAS oncogene family |
| RAB25 | CATX-8 | RAB25, member RAS oncogene family |
| RAC1 | p21-Rac1, Rac-1, TC-25 | Ras-related C3 botulinum toxin substrate 1 (rho family, small GTP binding protein Rac1) |
| RAD23A | HHR23A, MGC111083 | RAD23 homolog A (*S. cerevisiae*) |
| RAD23B | HHR23B, HR23B, P58 | RAD23 homolog B (*S. cerevisiae*) |
| RAD51 | BRCC5, HsRad51, HsT16930, RAD51A, RECA | RAD51 recombinase |

TABLE 1-continued

| Gene | Gene synonym | Gene description |
| --- | --- | --- |
| RAD51D | HsTRAD, R51H3, RAD51L3, Trad | RAD51 paralog D |
| RAD52 | | RAD52 homolog (*S. cerevisiae*) |
| RAD54B | RDH54 | RAD54 homolog B (*S. cerevisiae*) |
| RAF1 | c-Raf, CRAF, Raf-1 | Raf-1 proto-oncogene, serine/threonine kinase |
| RARA | NR1B1, RAR | Retinoic acid receptor, alpha |
| RARB | HAP, NR1B2, RRB2 | Retinoic acid receptor, beta |
| RARG | NR1B3, RARC | Retinoic acid receptor, gamma |
| RASA1 | CM-AVM, GAP, p120GAP, p120RASGAP, RASA | RAS p21 protein activator (GTPase activating protein) 1 |
| RB1 | OSRC, PPP1R130, RB | Retinoblastoma 1 |
| RBBP4 | lin-53, NURF55, RbAp48 | Retinoblastoma binding protein 4 |
| RBL1 | cp107, p107, PRB1 | Retinoblastoma-like 1 |
| RBL2 | p130, Rb2 | Retinoblastoma-like 2 |
| RBM6 | 3G2, DEF-3, DEF3, g16, NY-LU-12 | RNA binding motif protein 6 |
| RBP4 | | Retinol binding protein 4, plasma |
| REL | c-Rel, I-Rel | V-rel avian reticuloendotheliosis viral oncogene homolog |
| RELA | NFKB3, p65 | V-rel avian reticuloendotheliosis viral oncogene homolog A |
| RELB | REL-B | V-rel avian reticuloendotheliosis viral oncogene homolog B |
| RET | CDHF12, CDHR16, HSCR1, MEN2A, MEN2B, MTC1, PTC, RET51 | Ret proto-oncogene |
| RHOA | ARH12, ARHA, Rho12, RhoA, RHOH12 | Ras homolog family member A |
| RHOB | ARH6, ARHB, MST081, RhoB, RHOH6 | Ras homolog family member B |
| RHOC | ARH9, ARHC, RhoC | Ras homolog family member C |
| RPA2 | | Replication protein A2, 32 kDa |
| RPL27 | L27 | Ribosomal protein L27 |
| RPS3 | FLJ26283, FLJ27450, MGC87870, S3 | Ribosomal protein S3 |
| RPS6KA1 | HU-1, RSK, RSK1 | Ribosomal protein S6 kinase, 90 kDa, polypeptide 1 |
| RPS6KA3 | CLS, HU-3, MRX19, RSK, RSK2 | Ribosomal protein S6 kinase, 90 kDa, polypeptide 3 |
| RXRA | NR2B1 | Retinoid X receptor, alpha |
| RXRB | H-2RIIBP, NR2B2, RCoR-1 | Retinoid X receptor, beta |
| RXRG | NR2B3 | Retinoid X receptor, gamma |
| S100A1 | S100-alpha, S100A | S100 calcium binding protein A1 |
| S100A2 | CAN19, S100L | S100 calcium binding protein A2 |
| S100A4 | 18A2, 42A, CAPL, FSP1, MTS1, P9KA, PEL98 | S100 calcium binding protein A4 |
| S100A6 | 2A9, CABP, CACY, PRA | S100 calcium binding protein A6 |
| S100A7 | PSOR1, S100A7c | S100 calcium binding protein A7 |
| S100A8 | 60B8AG, CAGA, CFAG, CGLA, MRP8, P8 | S100 calcium binding protein A8 |
| S100A9 | 60B8AG, CAGB, CFAG, CGLB, LIAG, MAC387, MIF, MRP14, NIF, P14 | S100 calcium binding protein A9 |
| S100B | S100beta | S100 calcium binding protein B |
| S1PR1 | CD363, D1S3362, edg-1, EDG1 | Sphingosine-1-phosphate receptor 1 |
| SAA1 | PIG4, SAA, TP53I4 | Serum amyloid A1 |
| SAA2 | | Serum amyloid A2 |
| SART1 | Ara1, SNRNP110, Snu66 | Squamous cell carcinoma antigen recognized by T cells |
| SCGB1A1 | CC10, CC16, CCSP, UGB | Secretoglobin, family 1A, member 1 (uteroglobin) |
| SCGB1D2 | LIPB, LPHB | Secretoglobin, family 1D, member 2 |
| SCGB2A1 | LPHC, MGB2, MGC71973, UGB3 | Secretoglobin, family 2A, member 1 |
| SCGB2A2 | MGB1, MGC71974, UGB2 | Secretoglobin, family 2A, member 2 |
| SDC1 | CD138, SDC, SYND1, syndecan | Syndecan 1 |
| SELE | CD62E, ELAM, ELAM1, ESEL | Selectin E |
| SELL | CD62L, hLHRc, LAM-1, LAM1, Leu-8, LNHR, LSEL, Lyam-1, LYAM1, PLNHR | Selectin L |
| SELP | CD62, CD62P, GMP140, GRMP, PADGEM, PSEL | Selectin P (granule membrane protein 140 kDa, antigen CD62) |

TABLE 1-continued

| Gene | Gene synonym | Gene description |
|---|---|---|
| SEMA3B | LUCA-1, SemA, sema5, SEMAA, semaV | Sema domain, immunoglobulin domain (Ig), short basic domain, secreted, (semaphorin) 3B |
| 2-Sep | DIFF6, hNedd5, KIAA0158, NEDD5, Pnutl3 | Septin 2 |
| SERPINA1 | A1A, A1AT, AAT, alpha-1-antitrypsin, alpha1 AT, PI, PI1 | Serpin peptidase inhibitor, clade A (alpha-1 antiproteinase, antitrypsin), member 1 |
| SERPINA3 | AACT, ACT, alpha-1-antichymotrypsin | Serpin peptidase inhibitor, clade A (alpha-1 antiproteinase, antitrypsin), member 3 |
| SERPINA5 | PAI3, PCI, PLANH3, PROCI | Serpin peptidase inhibitor, clade A (alpha-1 antiproteinase, antitrypsin), member 5 |
| SERPINB2 | HsT1201, PAI2, PLANH2 | Serpin peptidase inhibitor, clade B (ovalbumin), member 2 |
| SERPINB3 | HsT1196, SCC, SCCA1, T4-A | Serpin peptidase inhibitor, clade B (ovalbumin), member 3 |
| SERPINB4 | LEUPIN, PI11, SCCA-2, SCCA1, SCCA2 | Serpin peptidase inhibitor, clade B (ovalbumin), member 4 |
| SERPINE1 | PAI, PAI1, PLANH1 | Serpin peptidase inhibitor, clade E (nexin, plasminogen activator inhibitor type 1), member 1 |
| SERPINF1 | EPC-1, PEDF, PIG35 | Serpin peptidase inhibitor, clade F (alpha-2 antiplasmin, pigment epithelium derived factor), member 1 |
| SFN | YWHAS | Stratifin |
| SHBG | ABP, MGC126834, MGC138391, TEBG | Sex hormone-binding globulin |
| SIRT2 | SIR2L | Sirtuin 2 |
| SKP2 | FBL1, FBXL1, p45 | S-phase kinase-associated protein 2, E3 ubiquitin protein ligase |
| SLC19A1 | FOLT | Solute carrier family 19 (folate transporter), member 1 |
| SLC2A1 | DYT18, GLUT, GLUT1, HTLVR | Solute carrier family 2 (facilitated glucose transporter), member 1 |
| SLC3A2 | 4F2, 4F2HC, 4T2HC, CD98, CD98HC, MDU1, NACAE | Solute carrier family 3 (amino acid transporter heavy chain), member 2 |
| SLPI | ALK1, ALP, BLPI, HUSI, HUSI-I, WAP4, WFDC4 | Secretory leukocyte peptidase inhibitor |
| SMAD1 | JV4-1, MADH1, MADR1 | SMAD family member 1 |
| SMAD2 | JV18-1, MADH2, MADR2 | SMAD family member 2 |
| SMAD3 | HsT17436, JV15-2, MADH3 | SMAD family member 3 |
| SMAD4 | DPC4, MADH4 | SMAD family member 4 |
| SMYD3 | KMT3E, ZMYND1, ZNFN3A1 | SET and MYND domain containing 3 |
| SOD1 | ALS, ALS1, IPOA | Superoxide dismutase 1, soluble |
| SOD2 | | Superoxide dismutase 2, mitochondrial |
| SOX1 | | SRY (sex determining region Y)-box 1 |
| SOX9 | CMD1, CMPD1, SRA1 | SRY (sex determining region Y)-box 9 |
| SP1 | | Sp1 transcription factor |
| SPARC | ON | Secreted protein, acidic, cysteine-rich (osteonectin) |
| SPARCL1 | MAST9 | SPARC-like 1 (hevin) |
| SPINK1 | PCTT, PSTI, Spink3, TATI | Serine peptidase inhibitor, Kazal type 1 |
| SPINT1 | HAI, MANSC2 | Serine peptidase inhibitor, Kunitz type 1 |
| SPINT2 | HAI-2, Kop | Serine peptidase inhibitor, Kunitz type, 2 |
| SPP1 | BNSP, BSPI, ETA-1, OPN | Secreted phosphoprotein 1 |
| SPRR1B | GADD33, SPRR1 | Small proline-rich protein 1B |
| SPRR3 | | Small proline-rich protein 3 |
| SPRY1 | hSPRY1 | Sprouty homolog 1, antagonist of FGF signaling (*Drosophila*) |
| SRC | ASV, c-src, SRC1 | SRC proto-oncogene, non-receptor tyrosine kinase |
| SRD5A1 | | Steroid-5-alpha-reductase, alpha polypeptide 1 (3-oxo-5 alpha-steroid delta 4-dehydrogenase alpha 1) |
| SRD5A2 | | Steroid-5-alpha-reductase, alpha polypeptide 2 (3-oxo-5 alpha-steroid delta 4-dehydrogenase alpha 2) |
| SST | SMST | Somatostatin |
| SSX2 | CT5.2a, HD21, HOM-MEL-40, MGC119055, MGC15364, MGC3884, SSX | Synovial sarcoma, X breakpoint 2 |

TABLE 1-continued

| Gene | Gene synonym | Gene description |
|---|---|---|
| SSX2B | CT5.2b | Synovial sarcoma, X breakpoint 2B |
| ST14 | HAI, MT-SP1, PRSS14, SNC19, TMPRSS14 | Suppression of tumorigenicity 14 (colon carcinoma) |
| STARD3 | es64, MLN64 | StAR-related lipid transfer (START) domain containing 3 |
| STAT4 | | Signal transducer and activator of transcription 4 |
| STAT5A | MGF, STAT5 | Signal transducer and activator of transcription 5A |
| STEAP1 | PRSS24, STEAP | Six transmembrane epithelial antigen of the prostate 1 |
| STMN | C1orf215, FLJ32206, Lag, LAP18, OP18, PP17, PP19, PR22, SMN | Stathmin 1 |
| STRAP | MAWD, pt-wd, UNRIP | Serine/threonine kinase receptor associated protein |
| STT3A | ITM1, MGC9042, STT3-A, TMC | STT3A, subunit of the oligosaccharyltransferase complex (catalytic) |
| SULT1E1 | EST, STE | Sulfotransferase family 1E, estrogen-preferring, member 1 |
| TAGLN | DKFZp686P11128, SM22, SMCC, TAGLN1, WS3-10 | Transgelin |
| TDRD6 | bA446F17.4, CT41.2, NY-CO-45, SPATA36 | Tudor domain containing 6 |
| TEK | CD202b, TIE-2, TIE2, VMCM, VMCM1 | TEK tyrosine kinase, endothelial |
| TERT | EST2, hEST2, TCS1, TP2, TRT | Telomerase reverse transcriptase |
| TF | PRO1557, PRO2086 | Transferrin |
| TFAP2B | AP2-B | Transcription factor AP-2 beta (activating enhancer binding protein 2 beta) |
| TFDP1 | Dp-1, DP1, DRTF1 | Transcription factor Dp-1 |
| TFDP2 | Dp-2 | Transcription factor Dp-2 (E2F dimerization partner 2) |
| TFF1 | BCEI, D21S21, HP1.A, HPS2, pNR-2, pS2 | Trefoil factor 1 |
| TFF2 | SML1 | Trefoil factor 2 |
| TFF3 | HITF, ITF | Trefoil factor 3 (intestinal) |
| TFRC | CD71, p90, TFR1 | Transferrin receptor |
| TG | AITD3, TGN | Thyroglobulin |
| TGFA | | Transforming growth factor, alpha |
| TGFB1 | CED, DPD1, TGFB, TGFbeta | Transforming growth factor, beta 1 |
| TGFB2 | | Transforming growth factor, beta 2 |
| TGFB3 | ARVD, ARVD1 | Transforming growth factor, beta 3 |
| TGFBR3 | betaglycan, BGCAN | Transforming growth factor, beta receptor III |
| TGM4 | TGP | Transglutaminase 4 |
| TGM7 | TGMZ | Transglutaminase 7 |
| THBS1 | THBS, THBS-1, TSP, TSP-1, TSP1 | Thrombospondin 1 |
| THBS2 | TSP2 | Thrombospondin 2 |
| THBS4 | | Thrombospondin 4 |
| THPO | MGDF, MPLLG, TPO | Thrombopoietin |
| THRA | AR7, EAR-7.1/EAR-7.2, ERBA, ERBA1, NR1A1, THRA1, THRA2, THRA3 | Thyroid hormone receptor, alpha |
| THRB | ERBA-BETA, ERBA2, GRTH, NR1A2, PRTH, THR1, THRB1, THRB2 | Thyroid hormone receptor, beta |
| TIE1 | JTK14, TIE | Tyrosine kinase with immunoglobulin-like and EGF-like domains 1 |
| TIMP1 | CLGI, EPO, TIMP | TIMP metallopeptidase inhibitor 1 |
| TIMP2 | CSC-21K | TIMP metallopeptidase inhibitor 2 |
| TIMP3 | SFD | TIMP metallopeptidase inhibitor 3 |
| TK1 | | Thymidine kinase 1, soluble |
| TMF1 | ARA160, TMF | TATA element modulatory factor 1 |
| TMPRSS2 | PRSS10 | Transmembrane protease, serine 2 |
| TMPRSS3 | DFNB10, DFNB8 | Transmembrane protease, serine 3 |
| TNC | DFNA56, HXB, MGC167029, TN | Tenascin C |
| TNF | DIF, TNF-alpha, TNFA, TNFSF2 | Tumor necrosis factor |
| TNFAIP2 | B94, EXOC3L3 | Tumor necrosis factor, alpha-induced protein 2 |

TABLE 1-continued

| Gene | Gene synonym | Gene description |
| --- | --- | --- |
| TNFAIP3 | A20, OTUD7C | Tumor necrosis factor, alpha-induced protein 3 |
| TNFRSF10A | Apo2, CD261, DR4, TRAILR-1 | Tumor necrosis factor receptor superfamily, member 10a |
| TNFRSF10B | CD262, DR5, KILLER, TRAIL-R2, TRICK2A, TRICKB | Tumor necrosis factor receptor superfamily, member 10b |
| TNFRSF10C | CD263, DcR1, LIT, TRAILR3, TRID | Tumor necrosis factor receptor superfamily, member 10c, decoy without an intracellular domain |
| TNFRSF10D | CD264, DcR2, TRAILR4, TRUNDD | Tumor necrosis factor receptor superfamily, member 10d, decoy with truncated death domain |
| TNFRSF11B | OCIF, OPG, TR1 | Tumor necrosis factor receptor superfamily, member 11b |
| TNFRSF12A | CD266, FN14, TweakR | Tumor necrosis factor receptor superfamily, member 12A |
| TNFRSF14 | ATAR, CD270, HVEA, HVEM, LIGHTR, TR2 | Tumor necrosis factor receptor superfamily, member 14 |
| TNFRSF1A | CD120a, TNF-R, TNF-R-I, TNF-R55, TNFAR, TNFR1, TNFR60 | Tumor necrosis factor receptor superfamily, member 1A |
| TNFRSF1B | CD120b, p75, TNF-R-II, TNF-R75, TNFBR, TNFR2, TNFR80 | Tumor necrosis factor receptor superfamily, member 1B |
| TNFRSF4 | ACT35, CD134, OX40, TXGP1L | Tumor necrosis factor receptor superfamily, member 4 |
| TNFRSF8 | CD30, D1S166E, KI-1 | Tumor necrosis factor receptor superfamily, member 8 |
| TNFRSF9 | 4-1BB, CD137, ILA | Tumor necrosis factor receptor superfamily, member 9 |
| TNFSF10 | Apo-2L, CD253, TL2, TRAIL | Tumor necrosis factor (ligand) superfamily, member 10 |
| TNFSF11 | CD254, ODF, OPGL, RANKL, TRANCE | Tumor necrosis factor (ligand) superfamily, member 11 |
| TNFSF13 | APRIL, CD256 | Tumor necrosis factor (ligand) superfamily, member 13 |
| TNFSF13B | BAFF, BLYS, CD257, TALL-1, TALL1, THANK, TNFSF20 | Tumor necrosis factor (ligand) superfamily, member 13b |
| TNFSF4 | CD252, gp34, OX-40L, TXGP1 | Tumor necrosis factor (ligand) superfamily, member 4 |
| TNFSF8 | CD153, CD30LG | Tumor necrosis factor (ligand) superfamily, member 8 |
| TNK2 | ACK, ACK1, p21cdc42Hs | Tyrosine kinase, non-receptor, 2 |
| TOP2A | TOP2 | Topoisomerase (DNA) II alpha 170 kDa |
| TP53 | LFS1, p53 | Tumor protein p53 |
| TP53BP2 | 53BP2, ASPP2, PPP1R13A | Tumor protein p53 binding protein 2 |
| TPD52 | D52, hD52, N8L | Tumor protein D52 |
| TPI1 | | Triosephosphate isomerase 1 |
| TPM1 | C15orf13, CMH3 | Tropomyosin 1 (alpha) |
| TPM2 | AMCD1, DA1, NEM4 | Tropomyosin 2 (beta) |
| TPX2 | C20orf1, C20orf2, DIL-2, p100 | TPX2, microtubule-associated |
| TRAF1 | EBI6 | TNF receptor-associated factor 1 |
| TRAF2 | TRAP3 | TNF receptor-associated factor 2 |
| TRAF4 | CART1, MLN62, RNF83 | TNF receptor-associated factor 4 |
| TRIM25 | EFP, RNF147, ZNF147 | Tripartite motif containing 25 |
| TRIP4 | HsT17391, ZC2HC5 | Thyroid hormone receptor interactor 4 |
| TRO | KIAA1114, MAGE-D3, MAGED3 | Trophinin |
| TSG101 | TSG10, VPS23 | Tumor susceptibility 101 |
| TSPAN8 | CO-029, TM4SF3 | Tetraspanin 8 |
| TSPO | BZRP, DBI, IBP, MBR, mDRC, PBR, pk18, PKBS | Translocator protein (18 kDa) |
| TTR | CTS, CTS1, HsT2651, PALB | Transthyretin |
| TUSC2 | C3orf11, FUS1, PAP, PDAP2 | Tumor suppressor candidate 2 |
| TWIST1 | ACS3, bHLHa38, BPES2, BPES3, CRS, CRS1, H-twist, SCS, TWIST | Twist family bHLH transcription factor 1 |
| TXLNA | DKFZp451J0118 | Taxilin alpha |
| TYMP | ECGF1, MNGIE | Thymidine phosphorylase |
| TYMS | HsT422, TMS, TS, Tsase | Thymidylate synthetase |
| TYRO3 | Brt, Dtk, RSE, Sky, Tif | TYRO3 protein tyrosine kinase |
| UBA1 | A1S9T, CFAP124, GXP1, POC20, UBE1, UBE1X | Ubiquitin-like modifier activating enzyme 1 |

TABLE 1-continued

| Gene | Gene synonym | Gene description |
| --- | --- | --- |
| UBE2C | UBCH10 | Ubiquitin-conjugating enzyme E2C |
| UBE2I | UBC9 | Ubiquitin-conjugating enzyme E2I |
| UBE2N | MGC8489, UBC13, UbcH-ben | Ubiquitin-conjugating enzyme E2N |
| UGT1A10 | UGT1J | UDP glucuronosyltransferase 1 family, polypeptide A10 |
| UGT1A3 | UGT1C | UDP glucuronosyltransferase 1 family, polypeptide A3 |
| UGT1A4 | HUG-BR2, UGT1D | UDP glucuronosyltransferase 1 family, polypeptide A4 |
| UGT1A8 | UGT1H | UDP glucuronosyltransferase 1 family, polypeptide A8 |
| UGT1A9 | HLUGP4, LUGP4, UGT1AI | polypeptide A9 |
| USH1C | AIE-75, DFNB18, harmonin, NY-CO-37, NY-CO-38, PDZ-73, PDZ73, PDZD7C | Usher syndrome 1C (autosomal recessive, severe) |
| VAMP3 | CEB | Vesicle-associated membrane protein 3 |
| VCAM1 | CD106 | Vascular cell adhesion molecule 1 |
| VEGFA | VEGF, VEGF-A, VPF | Vascular endothelial growth factor A |
| VEGFB | VEGFL, VRF | Vascular endothelial growth factor B |
| VEGFC | VRP | Vascular endothelial growth factor C |
| VHL | VHL1 | Von Hippel-Lindau tumor suppressor, E3 ubiquitin protein ligase |
| VIL1 | D2S1471, VIL | Villin 1 |
| VIP | | Vasoactive intestinal peptide |
| VTN | VN | Vitronectin |
| VWF | F8VWF | Von Willebrand factor |
| WEE1 | | WEE1 G2 checkpoint kinase |
| WFDC2 | dJ461P17.6, EDDM4, HE4, WAP5 | WAP four-disulfide core domain 2 |
| WISP1 | CCN4 | WNT1 inducible signaling pathway protein 1 |
| WNT1 | INT1 | Wingless-type MMTV integration site family, member 1 |
| WNT2 | INT1L1, IRP | Wingless-type MMTV integration site family member 2 |
| WRN | RECQ3, RECQL2 | Werner syndrome, RecQ helicase-like |
| WT1 | AWT1, GUD, WAGR, WIT-2 | Wilms tumor 1 |
| XBP1 | XBP2 | X-box binding protein 1 |
| XIAP | API3, BIRC4, hILP | X-linked inhibitor of apoptosis |
| XPA | XP1, XPAC | Xeroderma pigmentosum, complementation group A |
| XPC | RAD4, XPCC | Xeroderma pigmentosum, complementation group C |
| XRCC2 | | X-ray repair complementing defective repair in Chinese hamster cells 2 |
| XRCC3 | | X-ray repair complementing defective repair in Chinese hamster cells 3 |
| XRCC4 | | X-ray repair complementing defective repair in Chinese hamster cells 4 |
| XRCC5 | KARP-1, KU80, Ku86, KUB2 | X-ray repair complementing defective repair in Chinese hamster cells 5 (double-strand-break rejoining) |
| XRCC6 | D22S671, D22S731, G22P1, KU70, ML8 | X-ray repair complementing defective repair in Chinese hamster cells 6 |
| YBX1 | BP-8, CSDA2, CSDB, DBPB, MDR-NF1, NSEP-1, NSEP1, YB-1, YB1 | Y box binding protein 1 |
| YWHAB | YWHAA | Tyrosine 3-monooxygenase/tryptophan 5-monooxygenase activation protein, beta |
| YWHAE | FLJ45465 | Tyrosine 3-monooxygenase/tryptophan 5-monooxygenase activation protein, epsilon |
| YWHAH | YWHA1 | Tyrosine 3-monooxygenase/tryptophan 5-monooxygenase activation protein, eta |
| ZBTB16 | PLZF, ZNF145 | Zinc finger and BTB domain containing 16 |
| ZMAT3 | FLJ12296, MGC10613, PAG608, WIG-1, WIG1 | Zinc finger, matrin-type 3 |

In one embodiment, the biomarker is MYC. In one embodiment, the measurable aspect of MYC is its expression status. In one embodiment, the biomarker is overexpression of MYC.

Thus, in certain aspects of the disclosure, the biomarker is MYC which is differentially present in a subject of one phenotypic status, e.g., a patient having cancer, e.g., hepatocellular carcinoma (HCC), glioblastomas (GBM), lung cancer, breast cancer, head and neck cancer, prostate cancer, melanoma, or colorectal cancer, as compared with another phenotypic status, e.g., a normal undiseased subject or a patient having cancer without overexpression MYC.

In one embodiment, the biomarker is MCL1. In one embodiment, the measurable aspect of MCL1 is its expression status. In one embodiment, the biomarker is overexpression of MCL1.

A biomarker is differentially present between different phenotypic status groups if the mean or median expression or mutation levels of the biomarker is calculated to be different, i.e., higher or lower, between the groups. Thus, biomarkers provide an indication that a subject, e.g., a cancer patient, belongs to one phenotypic status or another.

Thus, in certain aspects of the disclosure, the biomarker is MCL1 which is differentially present, i.e., overexpressed, in a subject of one phenotypic status, e.g., a patient having cancer, e.g., hepatocellular carcinoma (HCC), glioblastomas (GBM), lung cancer, breast cancer, head and neck cancer, prostate cancer, melanoma, colorectal cancer, medulloblastoma, or general brain tumors, as compared with another phenotypic status, e.g., an undiseased patient or a cancer patient without overexpression MCL1.

In addition to individual biological compounds, e.g., MYC or MCL1, the term "biomarker" as used herein is meant to include groups, sets, or arrays of multiple biological compounds. For example, the combination of MYC and MCL1 may comprise a biomarker. The term "biomarker" may comprise one, two, three, four, five, six, seven, eight, nine, ten, fifteen, twenty, twenty five, thirty, or more, biological compounds.

The determination of the expression level or mutation status of a biomarker in a patient can be performed using any of the many methods known in the art. Any method known in the art for quantitating specific proteins and/or detecting MYC and/or MCL1 expression, or the expression or mutation levels of any other biomarker in a patient or a biological sample may be used in the methods of the disclosure. Examples include, but are not limited to, PCR (polymerase chain reaction), or RT-PCR, Northern blot, Western blot, ELISA (enzyme linked immunosorbent assay), RIA (radioimmunoassay), gene chip analysis of RNA expression, immunohistochemistry or immunofluorescence. See, e.g., Slagle et al. Cancer 83:1401 (1998). Certain embodiments of the disclosure include methods wherein biomarker RNA expression (transcription) is determined. Other embodiments of the disclosure include methods wherein protein expression in the biological sample is determined. See, for example, Harlow et al., Antibodies: A Laboratory Manual, Cold Spring Harbor Laboratory, Cold Spring Harbor, N.Y., (1988) and Ausubel et al., Current Protocols in Molecular Biology, John Wiley & Sons, New York 3rd Edition, (1995). For northern blot or RT-PCR analysis, RNA is isolated from the tumor tissue sample using RNAse free techniques. Such techniques are commonly known in the art.

In one embodiment of the disclosure, a biological sample is obtained from the patient and cells in the biopsy are assayed for determination of biomarker expression or mutation status.

In one embodiment of the disclosure, PET imaging is used to determine biomarker expression.

In another embodiment of the disclosure, Northern blot analysis of biomarker transcription in a tumor cell sample is performed. Northern analysis is a standard method for detection and/or quantitation of mRNA levels in a sample. Initially, RNA is isolated from a sample to be assayed using Northern blot analysis. In the analysis, the RNA samples are first separated by size via electrophoresis in an agarose gel under denaturing conditions. The RNA is then transferred to a membrane, crosslinked and hybridized with a labeled probe. Typically, Northern hybridization involves polymerizing radiolabeled or nonisotopically labeled DNA, in vitro, or generation of oligonucleotides as hybridization probes. Typically, the membrane holding the RNA sample is prehybridized or blocked prior to probe hybridization to prevent the probe from coating the membrane and, thus, to reduce non-specific background signal. After hybridization, typically, unhybridized probe is removed by washing in several changes of buffer. Stringency of the wash and hybridization conditions can be designed, selected and implemented by any practitioner of ordinary skill in the art. Detection is accomplished using detectably labeled probes and a suitable detection method. Radiolabeled and non-radiolabeled probes and their use are well known in the art. The presence and or relative levels of expression of the biomarker being assayed can be quantified using, for example, densitometry.

In another embodiment of the disclosure, biomarker expression and/or mutation status is determined using RT-PCR. RT-PCR allows detection of the progress of a PCR amplification of a target gene in real time. Design of the primers and probes required to detect expression and/or mutation status of a biomarker of the disclosure is within the skill of a practitioner of ordinary skill in the art. RT-PCR can be used to determine the level of RNA encoding a biomarker of the disclosure in a tumor tissue sample. In an embodiment of the disclosure, RNA from the biological sample is isolated, under RNAse free conditions, than converted to DNA by treatment with reverse transcriptase. Methods for reverse transcriptase conversion of RNA to DNA are well known in the art. A description of PCR is provided in the following references: Mullis et al., *Cold Spring Harbor Symp. Quant. Biol.* 51:263 (1986); EP 50,424; EP 84,796; EP 258,017; EP 237,362; EP 201,184; U.S. Pat. Nos. 4,683,202; 4,582,788; 4,683,194.

RT-PCR probes depend on the 5'-3' nuclease activity of the DNA polymerase used for PCR to hydrolyze an oligonucleotide that is hybridized to the target amplicon (biomarker gene). RT-PCR probes are oligonucleotides that have a fluorescent reporter dye attached to the 5, end and a quencher moiety coupled to the 3' end (or vice versa). These probes are designed to hybridize to an internal region of a PCR product. In the unhybridized state, the proximity of the fluor and the quench molecules prevents the detection of fluorescent signal from the probe. During PCR amplification, when the polymerase replicates a template on which an RT-PCR probe is bound, the 5'-3' nuclease activity of the polymerase cleaves the probe. This decouples the fluorescent and quenching dyes and FRET no longer occurs. Thus, fluorescence increases in each cycle, in a manner proportional to the amount of probe cleavage. Fluorescence signal emitted from the reaction can be measured or followed over time using equipment which is commercially available using routine and conventional techniques.

In another embodiment of the disclosure, expression of proteins encoded by biomarkers are detected by western blot analysis. A western blot (also known as an immunoblot) is a method for protein detection in a given sample of tissue homogenate or extract. It uses gel electrophoresis to separate denatured proteins by mass. The proteins are then transferred out of the gel and onto a membrane (e.g., nitrocellulose or polyvinylidene fluoride (PVDF)), where they are detected using a primary antibody that specifically bind to the protein. The bound antibody can then detected by a secondary antibody that is conjugated with a detectable label (e.g., biotin, horseradish peroxidase or alkaline phosphatase). Detection of the secondary label signal indicates the presence of the protein.

In another embodiment of the disclosure, the expression of a protein encoded by a biomarker is detected by enzyme-linked immunosorbent assay (ELISA). In one embodiment of the disclosure, "sandwich ELISA" comprises coating a plate with a capture antibody; adding sample wherein any antigen present binds to the capture antibody; adding a detecting antibody which also binds the antigen; adding an enzyme-linked secondary antibody which binds to detecting antibody; and adding substrate which is converted by an enzyme on the secondary antibody to a detectable form. Detection of the signal from the secondary antibody indicates presence of the biomarker antigen protein.

In another embodiment of the disclosure, the expression of a biomarker is evaluated by use of a gene chip or microarray. Such techniques are within ordinary skill held in the art.

The present disclosure also provides the following particular embodiments with respect to biomarkers:

Embodiment I

A method of treating a patient having cancer, the method comprising administering to the patient a therapeutically effective amount of a TG02 polymorphic form, wherein one or more of the genes listed in Table 1 is differentially present in a biological sample taken from the patient as compared with a biological sample taken from a subject of another phenotypic status.

Embodiment II

The method of Embodiment I, wherein MYC overexpression is present in a sample taken from the patient.

Embodiment III

The method of Embodiments I or II, wherein MCL1 overexpression is present in a sample taken from the patient.

Embodiment IV

The method of any one of Embodiments I-III further comprising administering to the patient a therapeutically effective amount of an immune checkpoint inhibitor.

Embodiment V

The method of Embodiment IV, wherein the TG02 polymorphic form is administered to the patient before an immune checkpoint inhibitor.

Embodiment VI

The method of Embodiment IV, wherein the TG02 polymorphic form is administered to the patient after an immune checkpoint inhibitor.

Embodiment VII

The method of Embodiment IV, wherein the TG02 polymorphic form is administered to the patient at the same time as an immune checkpoint inhibitor.

Embodiment VIII

The method of any one of Embodiments IV-VII, wherein the immune checkpoint inhibitor is selected from the group consisting of a PD-1 inhibitor, a PD-L inhibitor, a CTLA-4 inhibitor, a LAG3 inhibitor, a TIM3 inhibitor, and a cd47 inhibitor.

Embodiment IX

The method of Embodiment VIII, wherein the immune checkpoint inhibitor is a PD-1 inhibitor.

Embodiment X

The method of Embodiment IX, wherein the PD-1 inhibitor is an anti-PD-1 antibody.

Embodiment XI

The method of Embodiment X, wherein the anti-PD-1 antibody is selected from the group consisting of nivolumab, pembrolizumab, pidilizumab and STI-1110.

Embodiment XII

The method of Embodiment VIII, wherein the immune checkpoint inhibitor is a PD-L1 inhibitor.

Embodiment XIII

The method of Embodiment XII, wherein the PD-L1 inhibitor is an anti-PD-L1 antibody.

Embodiment XIV

The method of Embodiment XII, wherein the anti-PD-L1 antibody is selected from the group consisting of avelumab, atezolizumab, durvalumab, and STI-1014

Embodiment XV

The method of Embodiment VIII, wherein the immune checkpoint inhibitor is an anti-CTLA-4 inhibitor.

Embodiment XVI

The method of Embodiment XV, wherein the CTLA-4 inhibitor is an anti-CTLA-4 antibody.

Embodiment XVII

The method of Embodiment XVI, wherein the anti-CTLA-4 antibody is selected from the group consisting of ipilimumab and tremelimumab.

Embodiment XVIII

The method of Embodiment VIII, wherein immune checkpoint inhibitor is a LAG3 inhibitor.

Embodiment XIX

The method of Embodiment XVII, wherein the LAG3 inhibitor is an anti-LAG3 antibody.

Embodiment XX

The method of Embodiment XIX, wherein the anti-LAG3 antibody is GSK2831781.

Embodiment XXI

The method of Embodiment XX, wherein the immune checkpoint inhibitor is a TIM3 inhibitor.

Embodiment XXII

The method of Embodiment XXI, wherein the TIM3 inhibitor is an anti-TIM3 antibody.

Embodiment XXIII

The method of any one of Embodiments I-III further comprising administering to the patient a therapeutically effective amount of an alkylating agent.

Embodiment XXIV

The method of Embodiment XXIII, wherein the TG02 polymorphic form is administered to the patient before the alkylating agent.

Embodiment XXV

The method of Embodiment XXIII, wherein the TG02 polymorphic form is administered to the patient after the alkylating agent.

Embodiment XXVI

The method of Embodiment XXIII, wherein a therapeutically effective amount of the TG02 polymorphic form is administered to the patient at the same time as the alkylating agent.

Embodiment XXVII

The method of any one of Embodiments XXIII-XXVI, wherein the alkylating agent is temozolimide.

Embodiment XXVIII

The method of any one of Embodiments I-III further comprising administering to the patient a therapeutically effective amount of a protein kinase inhibitor.

Embodiment XXIX

The method of Embodiment XXVIII, wherein the TG02 polymorphic form is administered to the patient before the protein kinase inhibitor.

Embodiment XXX

The method of Embodiment XXVIII, wherein the TG02 polymorphic form is administered to the patient after the protein kinase inhibitor.

Embodiment XXXI

The method of Embodiment XXVIII, wherein a therapeutically effective amount of TG02 is administered to the patient at the same time as the protein kinase inhibitor.

Embodiment XXXII

The method of any one of Embodiments XXVIII-XXXI, wherein the protein kinase inhibitor is sorafenib.

Embodiment XXXIII

The method of any one of Embodiments I-III further comprising administering to the patient a therapeutically effective amount of a proteasome inhibitor.

Embodiment XXXIV

The method of Embodiment XXXIII, wherein the TG02 polymorphic form is administered to the patient before the proteasome inhibitor.

Embodiment XXXV

The method of Embodiment XXXIII, wherein the TG02 polymorphic form is administered to the patient after the proteasome inhibitor.

Embodiment XXXVI

The method of Embodiment XXXIII, wherein a therapeutically effective amount of the TG02 polymorphic form is administered to the patient at the same time as the proteasome inhibitor.

Embodiment XXXVII

The method of any one of Embodiments XXXIII-XXXVI, wherein the proteasome inhibitor is bortezomib.

Embodiment XXXVIII

The method of any one of Embodiments XXXIII-XXXVI, wherein the proteasome inhibitor is carfilizomib.

Embodiment XXXIX

The method of any one of Embodiments I-III further comprising administering to the patient a therapeutically effective amount of a topoisomerase II inhibitor.

Embodiment XL

The method of Embodiment XXXIX, wherein the TG02 polymorphic form is administered to the patient before the topoisomerase II inhibitor.

Embodiment XLI

The method of Embodiment XXXIX, wherein the TG02 polymorphic form is administered to the patient after the topoisomerase II inhibitor.

Embodiment XLII

The method of Embodiment XXXIX, wherein a therapeutically effective amount of the TG02 polymorphic form is administered to the patient at the same time as the topoisomerase II inhibitor.

Embodiment XLIII

The method of any one of Embodiments XXXIX-XLII, wherein the topoisomerase II inhibitor is doxorubicin.

Embodiment XLIV

The method of any one of Embodiments I-III further comprising administering to the patient a therapeutically effective amount of a platinum coordinating complex.

Embodiment XLV

The method of Embodiment XLIV, wherein the TG02 polymorphic form is administered to the patient before the platinum coordinating complex.

Embodiment XLVI

The method of Embodiment XLIV, wherein the TG02 polymorphic form is administered to the patient after the platinum coordinating complex.

Embodiment XLVII

The method of Embodiment XLIV, wherein a therapeutically effective amount of the TG02 polymorphic form is administered to the patient at the same time as the platinum coordinating complex.

Embodiment XLVIII

The method of any one of Embodiments XLIV-XLVII, wherein the platinum coordinating complex is cisplatin.

Embodiment XLIX

The method of any one of Embodiments I-III further comprising administering to the patient a therapeutically effective amount of lenalidomide.

Embodiment L

The method of Embodiment XLIX, wherein the TG02 polymorphic form is administered to the patient before lenalidomide.

Embodiment LI

The method of Embodiment XLIX, wherein the TG02 polymorphic form is administered to the patient after lenalidomide.

Embodiment LII

The method of Embodiment XLIX, wherein a therapeutically effective amount of the TG02 polymorphic form is administered to the patient at the same time as lenalidomide.

Embodiment LIII

The method of any one of Embodiments I-III further comprising administering to the patient a therapeutically effective amount of radiotherapy.

Embodiment LIV

The method of Embodiment LIII, wherein the TG02 polymorphic form is administered to the patient before radiotherapy.

Embodiment LV

The method of Embodiment LIII, wherein the TG02 polymorphic form is administered to the patient after radiotherapy.

Embodiment LVI

The method of Embodiment LIII, wherein a therapeutically effective amount of the TG02 polymorphic form is administered to the patient at the same time as radiotherapy.

Embodiment LVII

A method of treating a patient having cancer, the method comprising administering to the patient therapeutically effective amounts of a TG02 polymorphic form and an immune checkpoint inhibitor.

Embodiment LVIII

The method of Embodiment LVII, wherein the TG02 polymorphic form is administered to the patient before the immune checkpoint inhibitor.

Embodiment LIX

The method of Embodiment LVII, wherein the TG02 polymorphic form is administered to the patient after the immune checkpoint inhibitor.

Embodiment LX

The method of Embodiment LVII, wherein the TG02 polymorphic form is administered to the patient at the same time as the immune checkpoint inhibitor.

Embodiment LXI

The method of any one of Embodiments LVII-LX, wherein immune checkpoint inhibitor is selected from the group consisting of a PD-1 inhibitor, a PD-L1 inhibitor, a CTLA-4 inhibitor, a LAG3 inhibitor, and a TIM3 inhibitor.

Embodiment LXII

The method of LXI, wherein the immune checkpoint inhibitor is a PD-1 inhibitor.

Embodiment LXIII

The method of Embodiment LXII, wherein the PD-1 inhibitor is an anti-PD-1 antibody.

Embodiment LXIV

The method of Embodiment LXIII, wherein the anti-PD-1 antibody is selected from the group consisting of nivolumab, pembrolizumab, pidilizumab and STI-1110.

Embodiment LXV

The method of Embodiment LXI, wherein the immune checkpoint inhibitor is a PD-L1 inhibitor.

Embodiment LXVI

The method of Embodiment LXV, wherein the PD-L1 inhibitor is an anti-PD-L1 antibody.

Embodiment LXVII

The method of Embodiment LXVI, wherein the anti-PD-L1 antibody is selected from the group consisting of avelumab, atezolizumab, durvalumab, and STI-1014

Embodiment LXVIII

The method of Embodiment LXI, wherein the immune checkpoint inhibitor is an anti-CTLA-4 inhibitor.

Embodiment LXIX

The method of Embodiment LXVIII, wherein the CTLA-4 inhibitor is an anti-CTLA-4 antibody.

Embodiment LXX

The method of Embodiment LXIX, wherein the anti-CTLA-4 antibody is selected from the group consisting of ipilimumab and tremelimumab.

Embodiment LXXI

The method of Embodiment LXI, wherein the immune checkpoint inhibitor is a LAG3 inhibitor.

Embodiment LXXII

The method of Embodiment LXXI, wherein the LAG3 inhibitor is an anti-LAG3 antibody.

Embodiment LXXIII

The method of Embodiment LXXII, wherein the anti-LAG3 antibody is GSK2831781.

Embodiment LXXIV

The method of Embodiment LXI, wherein the immune checkpoint inhibitor is a TIM3 inhibitor.

Embodiment LXXV

The method of Embodiment LXXIV, wherein the TIM3 inhibitor is an anti-TIM3 antibody.

Embodiment LXXVI

A method of treating a patient having cancer, the method comprising administering to the patient therapeutically effective amounts of a TG02 polymorphic form and an alkylating agent.

Embodiment LXXVII

The method of Embodiment LXXVI, wherein the TG02 polymorphic form is administered to the patient before the alkylating agent.

Embodiment LXXVIII

The method of Embodiment LXXVI, wherein the TG02 polymorphic form is administered to the patient after the alkylating agent.

Embodiment LXXIX

The method of Embodiment LXXVI, wherein the TG02 polymorphic form is administered to the patient at the same time as the alkylating agent.

Embodiment LXXX

The method of any one of Embodiments LXXVI-LXXIX, wherein the alkylating agent is temozolimide.

Embodiment LXXXI

A method of treating a patient having cancer, the method comprising administering to the patient therapeutically effective amounts of a TG02 polymorphic form and a protein kinase inhibitor.

Embodiment LXXXII

The method of Embodiment LXXXI, wherein the TG02 polymorphic form is administered to the patient before the protein kinase inhibitor.

Embodiment LXXXIII

The method of Embodiment LXXX, wherein the TG02 polymorphic form is administered to the patient after the protein kinase inhibitor.

Embodiment LXXXIV

The method of Embodiment LXXX, wherein a therapeutically effective amount of the TG02 polymorphic form is administered to the patient at the same time as the protein kinase inhibitor.

Embodiment LXXXV

The method of any one of Embodiments LXXXI-LXXXIV, wherein the protein kinase inhibitor is sorafenib.

Embodiment LXXXVI

A method of treating a patient having cancer, the method comprising administering to the patient therapeutically effective amounts of a TG02 polymorphic form and a proteasome inhibitor.

Embodiment LXXXVII

The method of Embodiment LXXXVI, wherein the TG02 polymorphic form is administered to the patient before the proteasome inhibitor.

Embodiment LXXXVIII

The method of Embodiment LXXXVI, wherein the TG02 polymorphic form is administered to the patient after the proteasome inhibitor.

Embodiment LXXXIX

The method of Embodiment LXXXVI, wherein a therapeutically effective amount of the TG02 polymorphic form is administered to the patient at the same time as the proteasome inhibitor.

Embodiment XC

The method of any one of Embodiments LXXXVI-LXXXIX, wherein the proteasome inhibitor is bortezomib.

Embodiment XCI

The method of any one of Embodiments LXXXVI-LXXXIX, wherein the proteasome inhibitor is carfilizomib.

Embodiment XCII

A method of treating a patient having cancer, the method comprising administering to the patient therapeutically effective amounts of the TG02 polymorphic form and a topoisomerase II inhibitor.

Embodiment XCIII

The method of Embodiment XCII, wherein the TG02 polymorphic form is administered to the patient before the topoisomerase II inhibitor.

Embodiment XCIV

The method of Embodiment XCII, wherein the TG02 polymorphic form is administered to the patient after the topoisomerase II inhibitor.

Embodiment XCV

The method of Embodiment XCII, wherein a therapeutically effective amount of the TG02 polymorphic form is administered to the patient at the same time as the topoisomerase II inhibitor.

Embodiment XCVI

The method of any one of Embodiments XCII-XCV, wherein the topoisomerase II inhibitor is doxorubicin.

Embodiment XCVII

A method of treating a patient having cancer, the method comprising administering to the patient therapeutically effective amounts of a TG02 polymorphic form and a platinum coordinating complex.

Embodiment XCVIII

The method of Embodiment XCVII, wherein the TG02 polymorphic form is administered to the patient before the platinum coordinating complex.

Embodiment XCIX

The method of Embodiment XCVII, wherein the TG02 polymorphic form is administered to the patient after the platinum coordinating complex.

Embodiment C

The method of Embodiment XCVII, wherein a therapeutically effective amount of the TG02 polymorphic form is administered to the patient at the same time as the platinum coordinating complex.

Embodiment CI

The method of any one of Embodiments XCVII-C, wherein the platinum coordinating complex is cisplatin.

Embodiment CII

A method of treating a patient having cancer, the method comprising administering to the patient therapeutically effective amounts of a TG02 polymorphic form and lenalidomide.

Embodiment CIII

The method of Embodiment CII, wherein the TG02 polymorphic form is administered to the patient before lenalidomide.

Embodiment CIV

The method of Embodiment CII, wherein the TG02 polymorphic form is administered to the patient after lenalidomide.

Embodiment CV

The method of Embodiment CII, wherein a therapeutically effective amount of the TG02 polymorphic form is administered to the patient at the same time as lenalidomide.

Embodiment CVI

A method of treating a patient having cancer, the method comprising administering to the patient therapeutically effective amounts of a TG02 polymorphic form and radiotherapy.

Embodiment CVII

The method of Embodiment CVI, wherein the TG02 polymorphic form is administered to the patient before radiotherapy.

Embodiment CVIII

The method of Embodiment CVI, wherein the TG02 polymorphic form is administered to the patient after radiotherapy.

Embodiment CIX

The method of Embodiment CVI, wherein a therapeutically effective amount of the TG02 polymorphic form is administered to the patient at the same time as radiotherapy

Embodiment CX

The method of any one of Embodiments I-CIX, wherein the cancer is a solid tumor.

Embodiment CXI

The method of any one of Embodiments I-CIX, wherein the cancer is a hematological malignancy.

Embodiment CXII

The method of any one of Embodiments I-CIX, wherein the cancer any one or more of the cancers of Table 2.

Embodiment CXIII

The method of Embodiment CXII, wherein the cancer is selected from the group consisting of hepatocellular carcinoma, glioblastoma, lung cancer, breast cancer, head and neck cancer, prostate cancer, melanoma, and colorectal cancer.

Embodiment CXIV

The method of Embodiment CXII, wherein the cancer is multiple myeloma.

Embodiment CXV

The method of any one of Embodiments I-CXIV, wherein the cancer has become resistant to conventional treatments.

Embodiment CXVI

A kit comprising a TG02 polymorphic form and an immune checkpoint inhibitor, an alkylating agent, a protein kinase inhibitor, a proteasome inhibitor, a topoisomerase II inhibitor, a platinum coordinating complex, or lenalidomide, and instructions for administering the TG02 polymorphic form and the immune checkpoint inhibitor, alkylating agent, protein kinase inhibitor, proteasome inhibitor, topoisomerase II inhibitor, platinum coordinating complex, or lenalidomide, to a patient having cancer.

Embodiment CXVII

A method of treating a patient having cancer, the method comprising administering a therapeutically effective amount of a TG02 polymorphic form to the patient, wherein cells of the patient contain a biomarker, and the biomarker is overexpression of MCL-1, overexpression of MYC, or co-overexpression of MCL-1 and MYC.

Embodiment CXVIII

A method of treating a patient having cancer, the method comprising:
(a) determining the expression level of MCL-1, MYC, or MCL-1 and MYC, in a biological sample from the patient, and when the expression level is determined to be higher than that of a control sample, e.g., a sample from a normal undiseased patient or a patient having cancer without overexpression of MCL-1, MYC, or MCL-1 and MYC,
(b) administering to the patient a therapeutically effective amount of a TG02 polymorphic form.

Embodiment CXIX

A method for treating a cancer that overexpresses MCL-1, MYC, or MCL-1 and MYC, in a patient, the method comprising administering to the patient a therapeutically effective amount of a TG02 polymorphic form.

Embodiment CXX

A method of treating a human patient having cancer, the method comprising:
(a) obtaining a biological sample from the patient;
(b) determining whether to biological sample co-overexpresses MCL-1 and MYC; and
(c) administering to the patient a therapeutically effective amount of a TG02 polymorphic form if the biological sample indicates co-overexpression of MCL-1 and MYC.

Embodiment CXXI

A method of treating a human patient having cancer, the method comprising:
(a) measuring the MCL-1 expression level in a biological sample collected from the patient prior to administering a TG02 polymorphic form to the subject;
(b) determining whether the MCL-1 expression level is higher than a predetermined threshold standard; and
(c) administering a therapeutically effective amount of the TG02 polymorphic form and, optionally, a MCL-1 inhibitor, to the patient if the MCL-1 expression level is higher than the predetermined threshold standard.

Embodiment CXXII

A method of treating a human patient having cancer, the method comprising:
(a) measuring the MYC expression level in a biological sample collected from the patient prior to administering a TG02 polymorphic form to the subject;
(b) determining whether the MYC expression level is higher than a predetermined threshold standard; and
(c) administering a therapeutically effective amount of the TG02 polymorphic form and, optionally, a MYC inhibitor, to the patient if the MYC expression level is higher than the predetermined threshold standard.

Embodiment CXXIII

The method of any one of Embodiments CXVII-CXXII, wherein at least one additional anticancer agent is administered to the patient.

Embodiment CXXIV

The method of Embodiment CXXIII, wherein the at least one additional anticancer agent is an anti-PD-1 antibody.

Embodiment CXXV

The method of Embodiment CXXIII, wherein the at least one additional anticancer agent is radiation.

Embodiment CXXVI

The method of Embodiment CXXIII, wherein the at least one additional anticancer agent is temozolomide.

Embodiment CXXVII

The method of any one of Embodiments CXVII-CXXVI, wherein the cancer is selected from the group consisting of glioblastoma, hepatocellular carcinoma, non-small cell and small-cell lung cancer, head and neck cancer, colorectal carcinoma, and triple-negative breast cancer.

Embodiment CXXVIII

A method of treating a human patient having glioblastoma, the method comprising administering therapeutically effective amounts of a TG02 polymorphic form and an anti-PD-1 antibody to the patient.

Embodiment CXXIX

A method of treating a human patient having glioblastoma, the method comprising administering therapeutically effective amounts of a TG02 polymorphic form and radiation to the patient.

Embodiment CXXX

A method of treating a human patient having glioblastoma, the method comprising administering therapeutically effective amounts of a TG02 polymorphic form and temozolomide to the patient.

Embodiment CXXXI

A method of treating a human patient having hepatocellular carcinoma, the method comprising administering therapeutically effective amounts of a TG02 polymorphic form and sorafenib or regorafenib to the patient.

Embodiment CXXXII

A method of treating a human patient having multiple myeloma, the method comprising administering therapeutically effective amounts of a TG02 polymorphic form and bortezomib, carfilzomib, or lenalidomide to the patient.

Embodiment CXXXIII

A method of treating a human patient having chronic lymphocytic leukemia, the method comprising administering therapeutically effective amounts of a TG02 polymorphic form and ibrutinib or idelalisib to the patient.

Embodiment CXXXIV

A method of treating a human patient having acute myeloid leukemia, the method comprising administering therapeutically effective amounts of a TG02 polymorphic form and cytarabine (Ara-C) to the patient.

Embodiment CXXXV

A method of treating a human patient having triple-negative breast cancer, the method comprising administering therapeutically effective amounts of a TG02 polymorphic form and doxorubicin to the patient.

Embodiment CXXXVI

A method of treating a human patient having small-cell lung cancer, the method comprising administering therapeutically effective amounts of a TG02 polymorphic form and ciplatin to the patient.

Embodiment CXXXVII

A method of treating a human patient having cancer, the method comprising administering therapeutically a effective amount of a TG02 polymorphic form to the patient.

Embodiment CXXXVIII

A method of treating a human patient having acute leukemia, multiple myeloma, glioblastoma, hepatocellular carcinoma, non-small cell cancer, small-cell lung cancer, head and neck cancer, colorectal carcinoma, or triple-negative breast cancer, the method comprising administering therapeutically a effective amount of a TG02 polymorphic form to the patient.

Embodiment CXXXVIX

The method of any one of Embodiments I-CXXXVIII, wherein the TG02 polymorphic form is TG02 Form X (citrate).

The disclosure is also directed to the following particular embodiments.

Embodiment 1

A TG02 polymorphic form selected from the group consisting of:

Form X (citrate) characterized as having a powder x-ray diffraction pattern with peaks 15.2, 15.5, 21.7, 22.1, 23.0, 26.2, and 29.9 degrees 2Θ;

Form I (FB) characterized as having a powder x-ray diffraction pattern with peaks at 6.077, 17.675, 17.994, 18.475, 19.135, and 19.727 degrees 2Θ;

Form II (FB) characterized as having a powder x-ray diffraction pattern with peaks at 8.238, 11.607, 16.683, 17.153, and 19.073 degrees 2Θ;

Form III (FB) characterized as having a powder x-ray diffraction pattern with peaks at 6.236, 17.674, 17.769, 19.056, 19.082, 21.631, and 25.596 degrees 2Θ;

Form IV (FB) characterized as having a powder x-ray diffraction pattern with peaks at 8.484, 17.409, 18.807, 19.299, and 22.616 degrees 2Θ;

Form V (FB) characterized as having a powder x-ray diffraction pattern with peaks at 7.151, 14.299, 19.114, 19.185, and 21.495 degrees 2Θ;

Form VI (HCl) characterized as having a powder x-ray diffraction pattern with peaks at 8.055, 12.695, 15.868, 16.664, 18.460, 19.392, 22.103, 24.552, and 25.604 degrees 2Θ;

Form VII (HCl) characterized as having a powder x-ray diffraction pattern with peaks at 6.601, 12.691, 13.364, 21.785, 23.554, and 27.007 degrees 2Θ; and Form VIII (HCl) characterized as having a powder x-ray diffraction pattern with peaks at 12.994, 16.147, 22.211, 23.305, and 24.586 degrees 2Θ.

Embodiment 2

The TG02 polymorphic form of Embodiment 1 which is Form X (citrate).

Embodiment 3

The TG02 polymorphic form of Embodiments 1 or 2 having an average particle size distribution of about 10 μm or less.

Embodiment 4

The TG02 polymorphic form of Embodiment 3 having an average particle size distribution of about 1 μm or less.

Embodiment 5

A pharmaceutical composition comprising the TG02 polymorphic form of any one of Embodiments 1-4 and one or more pharmaceutically acceptable excipients.

Embodiment 6

The composition of Embodiment 5, wherein at least one of the one or more pharmaceutically acceptable excipients are selected from the group consisting of silicified microcrystalline cellulose, hypromellose 2910, crospvidone, and magnesium stearate.

Embodiment 7

The composition of Embodiment 6, wherein at least one of the one or more pharmaceutically acceptable excipients is silicified microcrystalline cellulose.

Embodiment 8

A method of treating a patient having cancer, the method comprising administering to the patient a therapeutically effective amount of the TG02 polymorphic form of any one of Embodiments 1-4.

Embodiment 9

A method of treating a patient having cancer, the method comprising administering to the patient a therapeutically effective amount of the TG02 polymorphic form of any one of Embodiments 1-4, wherein MYC overexpression, MCL1 overexpression, or MYC and MCL1 overexpression is differentially present in the patient as compared with a subject of another phenotypic status.

Embodiment 10

The method of Embodiment 9, wherein MYC overexpression is differentially present in a sample taken from the patient.

Embodiment 11

The method of Embodiment 9, wherein MCL1 overexpression is differentially present in a sample taken from the patient.

Embodiment 12

The method of Embodiment 9, wherein MYC and MCL1 overexpression is differentially present in a biological sample taken from the patient

Embodiment 13

The method of any one of Embodiments 8-12 further comprising administering to the patient a therapeutically effective amount of a second therapeutic agent.

Embodiment 14

The method of Embodiment 13, wherein the second therapeutic agent is selected from the group consisting of temozolomide, daunorubicin, doxorubicin, epirubicin, idarubicin, valrubicin, cisplatin, bortezomib, carfilzomib, lenalidomide, sorafenib, and radiotherapy.

Embodiment 15

The method of Embodiment 13, wherein the second therapeutic agent is an immune checkpoint inhibitor.

Embodiment 16

The method of Embodiment 15, wherein the immune checkpoint inhibitor is a PD-1 inhibitor or a PD-L1 inhibitor.

Embodiment 17

The method of Embodiment 16, wherein the PD-1 inhibitor is an anti-PD-1 antibody.

Embodiment 18

The method of Embodiment 17, wherein the anti-PD-1 antibody is selected from the group consisting of nivolumab, pembrolizumab, pidilizumab and STI-1110.

Embodiment 19

The method of Embodiment 16, wherein the PD-L1 inhibitor is an anti-PD-L1 antibody.

Embodiment 20

The method of Embodiment 19, wherein the anti-PD-L1 antibody is selected from the group consisting of avelumab, atezolizumab, durvalumab, and STI-1014

Embodiment 21

The method of any one of Embodiments 8-20, wherein the cancer is a solid tumor.

Embodiment 22

The method of any one of Embodiments 8-20, wherein the cancer is a hematological malignancy.

Embodiment 23

The method of any one of Embodiments 8-20, wherein the cancer any one or more of the cancers of Table 2.

Embodiment 24

The method of Embodiment 23, wherein the cancer is selected from the group consisting of multiple myeloma, hepatocellular carcinoma, glioblastoma, lung cancer, breast cancer, head and neck cancer, prostate cancer, melanoma, and colorectal cancer.

Embodiment 25

The method of any one of Embodiments 8-24, wherein the cancer has become resistant to conventional treatments.

Embodiment 26

The TG02 polymorphic form of any one of Embodiments 1-4 for use in the treatment of cancer.

Embodiment 27

The TG02 polymorphic form for use of Embodiment 26, wherein the cancer is a solid tumor.

Embodiment 28

The TG02 polymorphic form for use of Embodiment 26, wherein the cancer is a hematological malignancy.

Embodiment 29

The TG02 polymorphic form for use of Embodiment 26, wherein the cancer any one or more of the cancers of Table 2.

Embodiment 30

The TG02 polymorphic form for use of Embodiment 26, wherein the cancer is selected from the group consisting of multiple myeloma, hepatocellular carcinoma, glioblastoma, lung cancer, breast cancer, head and neck cancer, prostate cancer, melanoma, and colorectal cancer.

Embodiment 31

Use of the TG02 polymorphic form of any one of Embodiments 1-4 for the manufacture of a medicament for treatment of cancer.

Embodiment 32

The use of the TG02 polymorphic form of Embodiment 31, wherein the cancer is a solid tumor.

Embodiment 33

The use of the TG02 polymorphic form of Embodiment 31, wherein the cancer is a hematological malignancy.

Embodiment 34

The use of the TG02 polymorphic form of Embodiment 31, wherein the cancer any one or more of the cancers of Table 2.

Embodiment 35

The use of the TG02 polymorphic form of Embodiment 31, wherein the cancer is selected from the group consisting of multiple myeloma, hepatocellular carcinoma, glioblastoma, lung cancer, breast cancer, head and neck cancer, prostate cancer, melanoma, and colorectal cancer.

Embodiment 36

The pharmaceutical composition of Embodiment 4 for use in treating cancer.

Embodiment 37

The pharmaceutical composition of Embodiment 36, wherein the cancer is a solid tumor.

Embodiment 38

The pharmaceutical composition of Embodiment 36, wherein the cancer is a hematological malignancy.

Embodiment 39

The pharmaceutical composition of Embodiment 36, wherein the cancer any one or more of the cancers of Table 2.

Embodiment 40

The pharmaceutical composition of Embodiment 36, wherein the cancer is selected from the group consisting of multiple myeloma, hepatocellular carcinoma, glioblastoma, lung cancer, breast cancer, head and neck cancer, prostate cancer, melanoma, and colorectal cancer.

Embodiment 41

A kit comprising the TG02 polymorphic form of any one of Embodiments 1-4 and instructions for administering the TG02 polymorphic form to a patient having cancer.

Embodiment 42

The kit of Embodiment 41 further comprising an immune checkpoint inhibitor or alkylating agent.

Embodiment 43

The kit of Embodiment 42 further comprising instructions for administering the immune checkpoint inhibitor or alkylating agent to the patient.

Embodiment 44

A method of making the composition of Embodiment 5, the method comprising admixing the TG02 polymorphic form and one or more pharmaceutically acceptable excipients.

Embodiment 45

The method of Embodiment 44, wherein the TG02 polymorphic form is Form X (citrate).

Embodiment 46

A method of making the TG02 Form X (citrate) of Embodiment 2, the method comprising:
(a) combining a solution of citric acid in ethanol with a solution of TG02 free base in DMSO/ethanol;
(b) heating the solution of (a) at about 70° C. for at least about 15 minutes to give a solution comprising TG02 citrate;
(c) cooling the solution of (b) comprising TG02 citrate to about 5° C. to give a crystalline solid; and (d) isolating the crystalline solid of (c) to give TG02 Form X (citrate).

Embodiment 47

The method of Embodiment 13, wherein the second therapeutic agent is regorafenib.

V. Definitions

The term "TG02" as used herein refers to (16E)-14-methyl-20-oxa-5,7,14,26-tetraazatetracyclo[19.3.1.1(2,6).1 (8,12)]heptacosa-1 (25),2(26),3,5,8(27),9,11,16,21,23-decaene.

The term "TG02 free base" or "TG02 FB" refers to the free base of (16E)-14-methyl-20-oxa-5,7,14,26-tetraazatetracyclo[19.3.1.1(2,6).1(8,12)]heptacosa-1(25),2(26),3,5,8 (27),9,11,16,21,23-decaene.

The term "TG02 acid addition salt" or "TG02 salt" refers to a pharmaceutically acceptable acid addition salt of (16E)-14-methyl-20-oxa-5,7,14,26-tetraazatetracyclo[19.3.1.1(2, 6).1(8,12)]heptacosa-1(25),2(26),3,5,8(27),9,11,16,21,23-decaene. Examples of acids which can be employed to form pharmaceutically acceptable acid addition salts include inorganic acids such as nitric, boric, hydrochloric, hydrobromic, sulfuric, and phosphoric, and organic acids such as oxalic, maleic, succinic, and citric. Nonlimiting examples of salts of TG02 include, but are not limited to, the hydrochloride, hydrobromide, hydroiodide, sulfate, bisulfate, 2-hydroxyethanesulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts.

The term "TG02 citrate" or "TG02 CA" refers to the citrate salt of (16E)-14-methyl-20-oxa-5,7,14,26-tetraazatetracyclo[19.3.1.1(2,6).1(8,12)]heptacosa-1(25),2(26),3,5,8 (27),9,11,16,21,23-decaene. This is also known as (16E)-14-methyl-20-oxa-5,7,14,26-tetraazatetracyclo[19.3.1.1(2, 6).1(8,12)]heptacosa-1 (25),2(26),3,5,8(27),9,11,16,21,23-decaene—citric acid.

The term "TG02 HCl" refers to the hydrochloric acid salt of (16E)-14-methyl-20-oxa-5,7,14,26-tetraazatetracyclo [19.3.1.1(2,6).1(8,12)]heptacosa-1(25),2(26),3,5,8(27),9,11, 16,21,23-decaene. This is also known as (16E)-14-methyl-20-oxa-5,7,14,26-tetraazatetracyclo[19.3.1.1(2,6).1(8,12)] heptacosa-1(25),2(26),3,5,8(27),9,11,16,21,23-decaene—hydrochloric acid.

The term "TG02 polymorphic forms" as used herein refers to crystalline polymorphic forms of TG02 free base and TG02 acid addition salts. TG02 polymorphic forms include, but are not limited to, any one or more of TG02 Form I (FB), TG02 Form II (FB), TG02 Form III (FB), TG02 Form IV (FB), TG02 Form V (FB), TG02 Form VI (HCl), TG02 Form VII (HCl), TG02 Form VIII (HCl), or TG02 Form X (citrate). In one embodiment, the TG02 polymorphic form is TG02 Form X (citrate).

The term "biological sample" as used herein refers any tissue or fluid from a patient that is suitable for detecting a biomarker, such as MYC and/or MCL1 expression status. Examples of useful biological samples include, but are not limited to, biopsied tissues and/or cells, e.g., solid tumor, lymph gland, inflamed tissue, tissue and/or cells involved in a condition or disease, blood, plasma, serous fluid, cerebrospinal fluid, saliva, urine, lymph, cerebral spinal fluid, and the like. Other suitable biological samples will be familiar to those of ordinary skill in the relevant arts. A biological sample can be analyzed for biomarker expression and/or mutation using any technique known in the art and can be obtained using techniques that are well within the scope of ordinary knowledge of a clinical practioner. In one embodiment of the disclosure, the biological sample comprises blood cells.

The terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language, e.g., "such as," provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number ±10%. Thus, "about 10" means 9 to 11.

As used herein, the term "substantially pure" with reference to a particular TG02 polymorphic form means that the polymorphic form comprises about 10% or less, e.g., about 9%, about 8%, about 7%, about 6%, about 5%, about 4%, about 3%, about 2%, or about 1%, or less, by weight, of any other physical, e.g., crystalline and/or amorphous, forms of TG02.

As used herein, the term "pure" with reference to a particular TG02 polymorphic form means that the polymorphic form comprises about 1% or less, e.g., about 0.9%, about 0.8%, about 0.7%, about 0.6%, about 0.5%, about 0.4%, about 0.3%, about 0.2%, or about 0.1%, or less, by weight, of any other physical forms of TG02. In one embodiment, a "pure" polymorphic form contains no PXRD-detectable amount of any other physical forms of TG02.

As used herein, the term "amorphous" refers to a solid form of TG02 that lacks the long-range order characteristic of a crystal, i.e., the solid is non-crystalline.

As used herein, the term "essentially the same" with reference to PXRD peak positions and relative intensities means that peak position and intensity variability are taken into account when comparing PXRD diffractograms. PXRD peak positions can show inter-apparatus variability as much as ±0.2° and be "essentially the same." Relative peak intensities can also show inter-apparatus variability due to degree of crystallinity, orientation, prepared sample surface, and other factors known to those skilled in the art, and should be taken as qualitative measures only.

As used herein, the term "micronization" refers to a process or method by which the size of a population of particles is reduced, typically to the micron scale.

As used herein, the term "micron" or "m" refer to "micrometer," which is $1\times10^{-6}$ meter.

As used herein, the term "average particle size distribution" or "$D_{50}$" is the diameter where 50 mass-% of the particles have a larger equivalent diameter, and the other 50 mass-% have a smaller equivalent diameter as determined by laser diffraction using Malvern Master Sizer Microplus equipment or its equivalent.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. However, in one embodiment, administration of a TG02 polymorphic form and/or an immune checkpoint inhibitor leads to complete remission of the cancer.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that causes a therapeutic response, e.g., normalization of blood counts, decrease in the rate of tumor growth, decrease in tumor mass, decrease in the number of metastases, increase in time to tumor progression, and/or increase patient survival time by at least about 2%. In other embodiments, a therapeutically effective amount will refer to the amount of a therapeutic agent that causes a therapeutic response of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100%, or more.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and act in concert. For example, a TG02 polymorphic form can be administered at the same time or sequentially in any order at different points in time as the immune checkpoint inhibitor and/or the optional therapeutic agent. The TG02 polymorphic form and the immune checkpoint inhibitor and/or the optional therapeutic agent can be administered separately, in any appropriate form and by any suitable route. When the TG02 polymorphic form and the immune checkpoint inhibitor and/or the optional therapeutic agent are not administered concurrently, it is understood that they can be administered in any order to a patient in need thereof. For example, the TG02 polymorphic form can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the immune checkpoint inhibitor, to an individual in need thereof. In various embodiments, the TG02 polymorphic form and the immune checkpoint inhibitor are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart. In one embodiment, the TG02 polymorphic form is administered 3-7 days prior to the day the immune checkpoint inhibitor is administered. In another embodiment, the TG02 polymorphic form is also administered on the day the immune checkpoint inhibitor is administered and continues to be administered until disease progression or TG02 therapy is no longer beneficial.

EXAMPLES

General Instrument and Methodology Details

X-Ray Powder Diffraction

X-ray Powder Diffraction (XRPD or PXRD) diffractograms were collected on a Bruker AXS C2 GADDS, Bruker AXS DB Advance, PANalytical Empyrean, or similar diffractometer using Cu Kα radiation.

Bruker AXS C2 GADDS Diffractometer

XRPD diffractograms were collected on a Bruker AXS C2 GADDS diffractometer using Cu Kαo radiation (40 kV, 40 mA), an automated XYZ stage, a laser video microscope for auto-sample positioning and a Vantec-500 2-dimensional area detector. X-ray optics consists of a single Gobel multilayer mirror coupled with a pinhole collimator of 0.3 mm.

The beam divergence, i.e. the effective size of the X-ray beam on the sample, was approximately 4 mm. A Θ-Θ continuous scan mode was employed with a sample detector distance of 20 ecm which gives an effective 2Θ range of 1.5°-32.5°. Typically, the sample was exposed to the X-ray beam for 120 seconds. The software used for data collection and analysis was GADDS for Win7/XP and Diffrac Plus EVA, respectively.

Samples run under ambient conditions were prepared as flat plate specimens using powder as received without grinding. Samples were prepared and analysed on either a glass slide or glass frit. Samples were lightly pressed onto a glass slide to obtain a flat surface for analysis. A glass frit filter block was used to isolate and analyse solids from suspensions by adding a small amount of suspension directly to the glass frit before filtration under a light vacuum.

For variable temperature (VT) experiments samples were mounted on an Anton Paar DHS 900 hot stage at ambient conditions. The sample was then heated to the appropriate temperature at 20° C./min and subsequently held isothermally for 1 minute before data collection was initiated. Samples were prepared and analysed on a silicon wafer mounted to the hot stage using a heat-conducting compound.

Bruker AXS DB Advance Diffractometer

XRPD diffractograms were collected on a Bruker D8 diffractometer using Cu Kα radiation (40 kV, 40 rnA) and a θ-2θ goniometer fitted with aGe monochromator. The incident beam passes through a 2.0 mm divergence slit followed by a 0.2 mm anti-scatter slit and knife edge. The diffracted beam passes through an 8.0 mm receiving slit with 2.50 Soller slits followed by the Lynxeye Detector. The software used for data collection and analysis was Diffrac Plus XRD Commander and Diffrac Plus EVA respectively.

Samples were run under ambient conditions as flat plate specimens using powder as received. The sample was prepared on a polished, zero-background (510) silicon wafer by gently pressing onto the flat surface or packed into a cut cavity. The sample was rotated in its own plane.

The details of the standard data collection method are: Angular range: 2 to 42° 2Θ; Step size: 0.05° 2 Θ; and Collection time: 0.5 s/step (total collection time: 6.40 min).

PANalytical Empyrean Diffractometer

XRPD diffractograms were collected on a PANalytical Empyrean diffractometer using Cu Kα radiation (45 kV, 40 rnA) in transmission geometry. A 0.5° slit, 4 mm mask and 0.04 rad Soller slits with a focusing mirror were used on the incident beam. A PIXcel$^{3D}$ detector, placed on the diffracted beam, was fitted with a receiving slit and 0.04 rad Soller slits. The software used for data collection was X'Pert Data Collector using X'Pert Operator Interface. The data were analysed and presented using Diffrac Plus EVA or HighScore Plus.

Samples were prepared and analysed in either a metal or Millipore 96 well-plate in transmission mode. X-ray transparent film was used between the metal sheets on the metal well-plate and powders (approximately 1-2 mg) were used as received. The Millipore plate was used to isolate and analyse solids from suspensions by adding a small amount of suspension directly to the plate before filtration under a light vacuum.

The scan mode for the metal plate used the gonic scan axis, whereas a 2θ scan was utilised for the Millipore plate.

The details of the standard screening data collection method are: Angular range: 2.5 to 32.0° 2Θ; Step size: 0.0130° 2Θ; and Collection time: 12.75 s/step (total collection time of 2.07 min).

The software used for data collection was X'Pert Data Collector and the data were analysed and presented using Diffrac Plus EVA or Highscore Plus.

Samples were prepared and analysed in an Anton Paar chromed sample holder.

Nuclear Magnetic Resonance (NMR)

$^1$H NMR spectra were collected on a Bruker 400 MHz instrument equipped with an auto-sampler and controlled by a DRX400 console. Samples were prepared in DMSO-d6 solvent, unless otherwise stated. Automated experiments were acquired using ICON-NMR configuration within Topspin software, using standard Brukerloaded experiments ($^1$H, $^{13}$C {$^1$H}, DEPT135). Off-line analysis was performed using ACD Spectrus Processor.

Differential Scanning Calorimetry (DSC)

DSC data were collected on a TA Instruments Q2000 equipped with a 50 position auto-sampler. Typically, 0.5-1.5 mg of each sample, in a pin-holed aluminium pan, was heated at either 2° C./min or 10° C./min from 25° C. to 250° C. A purge of dry nitrogen at 50 ml/min was maintained over the sample. The instrument control software was Advantage for Q Series and Thermal Advantage and the data were analysed using Universal Analysis or TRIOS.

Thermo-Gravimetric Analysis (TGA)

TGA data were collected on a TA Instruments Q500 TGA, equipped with a 16 position auto-sampler. Typically, 3-6 mg of each sample was loaded onto a pre-tared aluminium DSC pan and heated at 10° C./min from ambient temperature to 350° C. A nitrogen purge at 60 ml/min was maintained over the sample.

The instrument control software was Advantage for Q Series and Thermal Advantage and the data were analysed using Universal Analysis or TRIOS.

Polarised Light Microscopy (PLM)

Samples were analysed on a Leica LM/DM polarised light microscope with a digital video camera for image capture. A small amount of each sample was placed on a glass slide, with or without immersion oil, and covered with a glass slip. The sample was viewed with appropriate magnification and partially polarised light, coupled to a λ false-colour filter. Images were captured using StudioCapture or Image ProPlus software.

Gravimetric Vapour Sorption (GVS)

Sorption isotherms were obtained using a SMS DVS Intrinsic moisture sorption analyser, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite.

The sample was recovered after completion of the isotherm and re-analysed by XRPD.

Water Determination by Karl Fischer Titration (KF)

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. An average of these results is presented unless otherwise stated. Data collection and analysis were performed using Tiamo software.

Thermodynamic Aqueous Solubility

Aqueous solubility was determined by suspending sufficient compound in relevant media to give a maximum final concentration of ≥10 mg/ml of the parent freeform of the compound. The suspension was equilibrated at 25° C., on a Heidolph plate shaker set to 750 rpm for 24 hours. The pH of the saturated solution was then measured and the suspension filtered through a glass fibre C filter (particle retention 1.2 m) and diluted appropriately. Quantitation was by HPLC with reference to a standard solution of approximately 0.15 mg/ml in DMSO. Different volumes of the standard, diluted and undiluted sample solutions were injected. The solubility was calculated using the peak areas determined by integration of the peak found at the same retention time as the principal peak in the standard injection.

Light Stability Trials

Solid and liquid samples were exposed to accelerated stress conditions using an Atlas CPS+ light box. Samples were prepared for analysis in duplicate in clear glass vials with closed lids for the liquid samples and open vials for the solid samples. Two of the vials were exposed to light conditions and the other vial was wrapped in aluminium foil to act as reference material. The sample thickness of solid samples was no more than −3 mm.

Exposure to light was effected by a combination of a single quartz glass filter with two window glass filters to reduce the effects of UV light upon the test samples. Temperature effects on the samples were reduced by attaching a chiller unit to the light box. Analysis of the samples was performed by HPLC Example 1

Preparation of TG02 Free Base Polymorphic Forms

Form I (FB)

Preparation: NaHCO$_3$ (aq) was added to a mixture containing TG02.2HCl and DCM adjusting pH to 8. The separated organic layer was concentrated till near dryness to give TG02 Form I (FB).

Characterization: The PXRD of TG02 Form I (FB) is shown in FIG. 3. Table 3 lists the peak positions, d values, and relative peak intensities of TG02 Form I (FB).

TABLE 3

| Index | Angle (2-Theta °) | d Value (Å) | Relative Intensity |
|---|---|---|---|
| 1 | 6.077 | 14.53102 | 100.0% |
| 2 | 8.840 | 9.99553 | 0.8% |
| 3 | 10.404 | 8.49596 | 2.2% |
| 4 | 13.368 | 6.61832 | 2.0% |
| 5 | 14.031 | 6.30672 | 3.7% |
| 6 | 14.628 | 6.05083 | 7.0% |
| 7 | 17.675 | 5.01390 | 11.6% |
| 8 | 17.994 | 4.92580 | 6.5% |
| 9 | 18.475 | 4.79867 | 38.5% |
| 10 | 19.135 | 4.63446 | 7.2% |
| 11 | 19.727 | 4.49685 | 10.1% |
| 12 | 19.913 | 4.45515 | 5.4% |
| 13 | 21.698 | 4.09257 | 3.9% |
| 14 | 22.460 | 3.95543 | 3.1% |
| 15 | 24.749 | 3.59448 | 1.9% |
| 16 | 25.456 | 3.49626 | 5.3% |
| 17 | 25.833 | 3.44601 | 2.2% |
| 18 | 26.209 | 3.39751 | 3.6% |
| 19 | 26.527 | 3.35744 | 4.0% |
| 20 | 26.882 | 3.31396 | 0.8% |
| 21 | 28.004 | 3.18361 | 1.6% |
| 22 | 28.625 | 3.11602 | 0.5% |
| 23 | 28.857 | 3.09142 | 0.7% |
| 24 | 29.725 | 3.00315 | 1.9% |
| 25 | 30.305 | 2.94692 | 0.4% |
| 26 | 31.009 | 2.88160 | 0.3% |
| 27 | 31.689 | 2.82135 | 0.8% |
| 28 | 32.160 | 2.78109 | 0.6% |
| 29 | 33.741 | 2.65431 | 0.5% |
| 30 | 34.293 | 2.61283 | 0.4% |
| 31 | 35.029 | 2.55957 | 0.5% |

Form II (FB)

Preparation: K$_2$CO$_3$ (aq) was added to a solution containing TG02HCl and MeOH at 40-60° C. adjusting pH to 8-9. The product was filtered and dried to give TG02 Form II (FB).

Characterization: The PXRD of TG02 Form II (FB) is shown in FIG. 4. Table 4 lists the peak positions, d values, and relative peak intensities of TG02 Form II (FB).

TABLE 4

| Index | Angle (2-Theta °) | d Value (Å) | Relative Intensity |
|---|---|---|---|
| 1 | 6.025 | 14.65812 | 1.4% |
| 2 | 6.954 | 12.70150 | 7.9% |
| 3 | 8.238 | 10.72461 | 100.0% |
| 4 | 10.036 | 8.80626 | 0.7% |
| 5 | 11.607 | 7.61760 | 25.9% |
| 6 | 14.563 | 6.07746 | 1.0% |
| 7 | 15.299 | 5.78667 | 0.5% |
| 8 | 16.683 | 5.30984 | 22.1% |
| 9 | 17.153 | 5.16540 | 26.0% |
| 10 | 18.064 | 4.90672 | 1.6% |
| 11 | 18.546 | 4.78043 | 10.1% |
| 12 | 19.073 | 4.64946 | 40.0% |
| 13 | 21.013 | 4.22436 | 2.5% |
| 14 | 21.294 | 4.16916 | 4.6% |
| 15 | 22.342 | 3.97608 | 12.7% |
| 16 | 23.516 | 3.78001 | 4.5% |
| 17 | 24.029 | 3.70051 | 0.5% |
| 18 | 24.518 | 3.62784 | 1.5% |
| 19 | 25.204 | 3.53068 | 4.6% |
| 20 | 26.225 | 3.39544 | 2.7% |
| 21 | 26.509 | 3.35968 | 3.0% |
| 22 | 26.954 | 3.30524 | 2.5% |
| 23 | 27.212 | 3.27451 | 1.2% |
| 24 | 27.755 | 3.21161 | 1.5% |
| 25 | 28.047 | 3.17886 | 1.2% |
| 26 | 29.133 | 3.06275 | 1.2% |
| 27 | 31.644 | 2.82522 | 1.5% |
| 28 | 32.026 | 2.79241 | 1.8% |
| 29 | 33.634 | 2.66252 | 0.6% |
| 30 | 38.906 | 2.31296 | 0.4% |

Form III (FB)

Preparation: A solution of TG02 free base in DCM was swapped with toluene. After cooling to 20-30° C., the product was filtered and dried to give TG02 Form III (FB).

Characterization: The PXRD of TG02 Form III (FB) is shown in FIG. 5. Table 5 lists the peak positions, d values, and relative peak intensities of TG02 Form III (FB).

TABLE 5

| Index | Angle (2-Theta °) | d Value (Å) | Relative Intensity |
|---|---|---|---|
| 1 | 6.236 | 14.16204 | 100.0% |
| 2 | 10.734 | 8.23523 | 10.4% |
| 3 | 12.791 | 6.91506 | 3.7% |
| 4 | 13.957 | 6.34010 | 14.8% |
| 5 | 14.987 | 5.90674 | 9.4% |
| 6 | 15.053 | 5.88077 | 10.9% |
| 7 | 15.486 | 5.71739 | 26.2% |
| 8 | 15.599 | 5.67617 | 29.6% |
| 9 | 16.650 | 5.32029 | 1.3% |

TABLE 5-continued

| Index | Angle (2-Theta °) | d Value (Å) | Relative Intensity |
|---|---|---|---|
| 10 | 17.674 | 5.01413 | 89.8% |
| 11 | 17.769 | 4.98765 | 93.6% |
| 12 | 18.162 | 4.88050 | 13.2% |
| 13 | 18.649 | 4.75417 | 25.4% |
| 14 | 18.726 | 4.73479 | 27.5% |
| 15 | 19.056 | 4.65350 | 37.8% |
| 16 | 19.082 | 4.64721 | 38.9% |
| 17 | 19.676 | 4.50833 | 22.2% |
| 18 | 19.619 | 4.52115 | 23.3% |
| 19 | 21.718 | 4.08873 | 22.6% |
| 20 | 21.000 | 4.22691 | 7.8% |
| 21 | 21.536 | 4.12288 | 26.5% |
| 22 | 21.594 | 4.11207 | 29.9% |
| 23 | 21.631 | 4.10514 | 30.9% |
| 24 | 23.109 | 3.84567 | 4.7% |
| 25 | 24.800 | 3.58719 | 25.1% |
| 26 | 25.596 | 3.47737 | 44.3% |
| 27 | 26.589 | 3.34973 | 13.0% |
| 28 | 27.675 | 3.22071 | 11.4% |
| 29 | 27.857 | 3.20014 | 11.8% |
| 30 | 27.981 | 3.18625 | 9.7% |
| 31 | 29.046 | 3.07175 | 7.8% |
| 32 | 29.288 | 3.04691 | 4.0% |

Form IV (FB)

Preparation: A warm solution containing TG02 free base and DMF was cooled to 20-30° C. The product was filtered and dried to give TG02 Form IV (FB).

Characterization: The PXRD of TG02 Form IV (FB) is shown in FIG. 6. Table 6 lists the peak positions, d values, and relative peak intensities of TG02 Form IV (FB).

TABLE 6

| Index | Angle (2-Theta °) | d Value (Å) | Relative Intensity |
|---|---|---|---|
| 1 | 7.143 | 12.36611 | 14.9% |
| 2 | 7.184 | 12.29422 | 13.7% |
| 3 | 8.484 | 10.41370 | 67.9% |
| 4 | 11.850 | 7.46220 | 42.0% |
| 5 | 14.826 | 5.97050 | 9.4% |
| 6 | 15.597 | 5.67675 | 4.0% |
| 7 | 15.933 | 5.55779 | 3.3% |
| 8 | 16.957 | 5.22453 | 31.4% |
| 9 | 17.169 | 5.16040 | 21.5% |
| 10 | 17.409 | 5.08997 | 61.1% |
| 11 | 17.573 | 5.04269 | 17.0% |
| 12 | 18.311 | 4.84106 | 10.5% |
| 13 | 18.807 | 4.71465 | 93.2% |
| 14 | 19.299 | 4.59553 | 48.3% |
| 15 | 19.773 | 4.48636 | 11.0% |
| 16 | 21.337 | 4.16085 | 16.2% |
| 17 | 21.519 | 4.12623 | 27.5% |
| 18 | 22.616 | 3.92843 | 100.0% |
| 19 | 23.749 | 3.74353 | 7.5% |
| 20 | 24.791 | 3.58845 | 15.6% |
| 21 | 25.126 | 3.54135 | 8.3% |
| 22 | 25.448 | 3.49736 | 11.3% |
| 23 | 26.468 | 3.36482 | 12.1% |
| 24 | 26.729 | 3.33250 | 13.9% |
| 25 | 27.180 | 3.27825 | 23.7% |
| 26 | 27.970 | 3.18744 | 4.7% |
| 27 | 29.384 | 3.03719 | 6.3% |
| 28 | 30.310 | 2.94650 | 3.3% |
| 29 | 31.344 | 2.85159 | 8.2% |
| 30 | 31.867 | 2.80594 | 9.4% |
| 31 | 38.475 | 2.33792 | 4.7% |

Form V (FB)

Preparation: A warm solution containing TG02 free base and DMSO/acetone or NMP/acetone or DMF/EtOAc was cooled to 20-30° C. The product was filtered and dried to give TG02 Form V (FR).

Characterization: The PXRD of TG02 Form V (FB) is shown in FIG. 7. Table 7 lists the peak positions, d values, and relative peak intensities of TG02 Form V (FB).

TABLE 7

| Index | Angle (2-Theta °) | d Value (Å) | Relative Intensity |
|---|---|---|---|
| 1 | 7.087 | 12.46270 | 12.1% |
| 2 | 7.151 | 12.35255 | 100.0% |
| 3 | 8.271 | 10.68141 | 2.0% |
| 4 | 8.416 | 10.49824 | 4.0% |
| 5 | 10.245 | 8.62705 | 0.4% |
| 6 | 11.657 | 7.58525 | 1.3% |
| 7 | 11.739 | 7.53278 | 2.9% |
| 8 | 14.053 | 6.29687 | 0.3% |
| 9 | 14.299 | 6.18933 | 6.1% |
| 10 | 15.478 | 5.72033 | 0.7% |
| 11 | 16.858 | 5.25516 | 2.7% |
| 12 | 17.163 | 5.16220 | 1.2% |
| 13 | 17.336 | 5.11121 | 2.1% |
| 14 | 18.751 | 4.72848 | 1.8% |
| 15 | 19.114 | 4.63953 | 5.9% |
| 16 | 19.185 | 4.62256 | 7.4% |
| 17 | 21.259 | 4.17594 | 0.9% |
| 18 | 21.495 | 4.13071 | 9.7% |
| 19 | 21.867 | 4.06121 | 0.2% |
| 20 | 22.414 | 3.96346 | 0.5% |
| 21 | 23.607 | 3.76576 | 1.4% |
| 22 | 24.185 | 3.67699 | 0.2% |
| 23 | 24.711 | 3.59998 | 1.1% |
| 24 | 25.351 | 3.51045 | 0.2% |
| 25 | 26.345 | 3.38018 | 2.7% |
| 26 | 26.558 | 3.35357 | 0.3% |
| 27 | 27.092 | 3.28875 | 0.6% |
| 28 | 27.334 | 3.26010 | 0.2% |
| 29 | 29.159 | 3.06012 | 0.4% |
| 30 | 31.202 | 2.86423 | 0.6% |
| 31 | 36.149 | 2.48278 | 1.2% |
| 32 | 36.238 | 2.47691 | 0.6% |

Example 2

Preparation of TG02 HCl Polymorphic Forms

Form VI (HCl)

Preparation: A solution containing TG02·HCl (10 g), EtOH (184 mL) and water (16 mL) was heated to reflux for 1 h. The mixture was cooled to 0-5° C. and stirred for 1 h. The mixture was filtered, and the filter cake was washed with 90% EtOH (aq) and dried to give TG02 Form VI (HCl).

Characterization: The PXRD of TG02 Form VI (HCl) is shown in FIG. 8. Table 8 lists the peak positions, d values, and relative peak intensities of TG02 Form VI (HCl).

TABLE 8

| Index | Angle (2-Theta °) | d Value (Å) | Relative Intensity |
|---|---|---|---|
| 1 | 6.593 | 13.39617 | 41.8% |
| 2 | 8.055 | 10.96766 | 90.8% |
| 3 | 8.309 | 10.63284 | 45.6% |
| 4 | 9.300 | 9.50212 | 65.4% |
| 5 | 9.527 | 9.27630 | 69.2% |
| 6 | 10.843 | 8.15308 | 16.7% |
| 7 | 12.695 | 6.96730 | 96.1% |
| 8 | 12.917 | 6.84816 | 40.2% |
| 9 | 13.594 | 6.50861 | 19.1% |
| 10 | 14.505 | 6.10155 | 70.5% |
| 11 | 14.799 | 5.98113 | 18.4% |
| 12 | 15.868 | 5.58066 | 83.0% |
| 13 | 15.979 | 5.54199 | 58.7% |
| 14 | 16.289 | 5.43722 | 41.3% |

TABLE 8-continued

| Index | Angle (2-Theta °) | d Value (Å) | Relative Intensity |
|---|---|---|---|
| 15 | 16.491 | 5.37121 | 47.4% |
| 16 | 16.664 | 5.31561 | 71.7% |
| 17 | 17.409 | 5.09002 | 21.2% |
| 18 | 17.845 | 4.96641 | 34.5% |
| 19 | 18.460 | 4.80252 | 74.6% |
| 20 | 19.392 | 4.57378 | 100.0% |
| 21 | 20.553 | 4.31777 | 32.1% |
| 22 | 22.103 | 4.01853 | 49.9% |
| 23 | 22.290 | 3.98509 | 42.9% |
| 24 | 22.832 | 3.89183 | 31.6% |
| 25 | 23.197 | 3.83142 | 30.9% |
| 26 | 23.565 | 3.77237 | 56.2% |
| 27 | 24.552 | 3.62281 | 67.2% |
| 28 | 24.796 | 3.58772 | 63.8% |
| 29 | 25.353 | 3.51019 | 30.5% |
| 30 | 25.604 | 3.47630 | 63.7% |
| 31 | 26.981 | 3.30197 | 18.5% |

Form VII (HCl)

Preparation Method A: A solution containing TG02.2HCl (20 g), pyridine (60 mL) and H$_2$O (120 mL) was heated at 80° C. for 1-3 h. The mixture was cooled to 20-30° C. and stirred for 2 h. The mixture was filtered, and the filter cake was washed with H$_2$O and dried to give TG02 Form VII (HCl).

Preparation Method B: A solution containing TG02.2HCl (50 g) pyridine (150 mL) and EtOAc (300 mL) was heated at 80° C. for 2-3 h. The mixture was cooled to 20-30° C. and stirred for 2 h. The mixture was filtered, and the filter cake was washed with H2O and dried to give TG02 Form VII (HCl).

Preparation Method C: A solution containing TG02'HCl (5.7 g), EtOH (74.5 mL) and H$_2$O (8 mL) was heated at reflux for 1 h. The mixture was cooled to 0-5° C. and stirred for 1 h. The mixture was filtered, and the filter cake was washed with EtOH and dried to give TG02 Form VII (HCl).

Preparation Method D: A solution containing TG02-HCl (9.3 g) EtOH (284 mL) and H$_2$O (22 mL) was heated at reflux for 1 h. The mixture was cooled to 0-5° C. and stirred for 2 h. The mixture was filtered, and the filter cake was washed with EtOH and dried to give TG02 Form VII (HCl).

Characterization: The PXRD of TG02 Form VII (HCl) is shown in FIG. 9. Table 9 lists the peak positions, d values, and relative peak intensities of TG02 Form VII (HCl).

TABLE 9

| Index | Angle (2-Theta °) | d Value (Å) | Relative Intensity |
|---|---|---|---|
| 1 | 6.601 | 13.37949 | 100.0% |
| 2 | 9.152 | 9.65532 | 3.4% |
| 3 | 12.691 | 6.96956 | 15.3% |
| 4 | 13.364 | 6.62027 | 16.9% |
| 5 | 13.598 | 6.50683 | 6.3% |
| 6 | 14.802 | 5.98006 | 14.5% |
| 7 | 14.952 | 5.92026 | 2.1% |
| 8 | 16.061 | 5.51407 | 8.5% |
| 9 | 17.457 | 5.07590 | 2.4% |
| 10 | 18.555 | 4.77810 | 2.9% |
| 11 | 18.809 | 4.71417 | 6.5% |
| 12 | 19.548 | 4.53753 | 2.6% |
| 13 | 20.191 | 4.39445 | 3.3% |
| 14 | 20.549 | 4.31868 | 3.0% |
| 15 | 21.259 | 4.17601 | 2.7% |
| 16 | 21.025 | 4.22208 | 3.8% |
| 17 | 21.785 | 4.07639 | 10.2% |
| 18 | 22.084 | 4.02178 | 5.5% |
| 19 | 23.554 | 3.77407 | 61.2% |
| 20 | 24.135 | 3.68456 | 14.4% |
| 21 | 24.914 | 3.57101 | 8.1% |
| 22 | 25.287 | 3.51924 | 1.9% |
| 23 | 26.904 | 3.31123 | 5.1% |
| 24 | 27.007 | 3.29892 | 11.7% |
| 25 | 27.792 | 3.20747 | 4.4% |
| 26 | 28.179 | 3.16424 | 3.6% |
| 27 | 30.091 | 2.96742 | 1.2% |
| 28 | 31.007 | 2.88184 | 1.2% |
| 29 | 31.632 | 2.82632 | 3.7% |
| 30 | 33.498 | 2.67297 | 0.8% |

Form VIII (HCl)

Preparation: A solution containing TG02.HCl (77.1 g), EtOH (2340 mL) and H$_2$O (185 mL) was heated at reflux for 0.5 h. The mixture was cooled to 0-5° C. and stirred for 2 h. The mixture was filtered, and the filter cake was washed with EtOH and dried to give TG02 Form VIII (HCl). TG02 Form VIII (HCl) gradually converted to TG02 Form VI (HCl) over time.

Characterization: The PXRD of TG02 HCl Form VIII is shown in FIG. 10. Table 10 lists the peak positions, d values, and relative peak intensities of TG02 Form VII (HCl).

TABLE 10

| Index | Angle (2-Theta °) | d Value (Å) | Relative Intensity |
|---|---|---|---|
| 1 | 8.351 | 10.57951 | 29.3% |
| 2 | 9.402 | 9.39909 | 12.9% |
| 3 | 12.994 | 6.80778 | 61.4% |
| 4 | 16.147 | 5.48485 | 100.0% |
| 5 | 16.386 | 5.40540 | 31.3% |
| 6 | 16.807 | 5.27097 | 17.7% |
| 7 | 17.977 | 4.93024 | 51.8% |
| 8 | 18.624 | 4.76041 | 24.8% |
| 9 | 19.441 | 4.56226 | 51.2% |
| 10 | 20.933 | 4.24024 | 46.9% |
| 11 | 22.152 | 4.00961 | 36.1% |
| 12 | 22.211 | 3.99909 | 62.3% |
| 13 | 23.190 | 3.83254 | 41.3% |
| 14 | 23.305 | 3.81384 | 73.4% |
| 15 | 24.305 | 3.65916 | 27.5% |
| 16 | 24.317 | 3.65736 | 23.9% |
| 17 | 24.586 | 3.61800 | 72.3% |
| 18 | 24.679 | 3.60450 | 63.2% |
| 19 | 25.407 | 3.50293 | 33.0% |
| 20 | 25.513 | 3.48852 | 39.5% |
| 21 | 27.804 | 3.20607 | 23.7% |
| 22 | 33.775 | 2.65168 | 11.3% |

Example 3

Preparation of TG02 Form X (Citrate)

Preparation: Method A: A 12.2% w/v solution of TG02 free base was prepared in DMSO/ethanol (94/6 v/v) by heating to about 70° C. to dissolve the TG02 free base. A separate solution of citric acid in ethanol (10% w/v) containing a 2% molar excess of citric acid relative to TG02 free base was prepared. The volume of the citric acid/ethanol solution was about 64% relative to the TG02 free base solution. The citric acid/ethanol solution (at about 70° C.) was transferred to the TG02 free base solution to form TG02 citrate, and the solution was stirred for at least 30 minutes. Warm ethanol (1.5 volume equivalents to previous citric acid/TG02 free base solution) was added and the solution was stirred for at least one hour at about 70° C. The solution was cooled to about 5° C. TG02 citrate crystallized upon cooling. TG02 citrate was collected by filtration, washed with ethanol and dried to give TG02 Form X (citrate) in 88-93% yield.

Method B: A homogeneous mixture of TG02 Form X (citrate), TG02 Citrate Pattern 1 of U.S. Pat. No. 9,120,815, and TG02 Citrate Pattern 2 of U.S. Pat. No. 9,120,815 was treated with solvent (20 vol.) and agitated for 4 days at different temperatures (5° C., 25° C., and 50° C.). The recovered solids were air dried and analysed by XRPD. As summarized in Table 11, several solvents resulted in the recovery of TG02 Form X (citrate).

TABLE 11

| Solvent | Temperature | TG02 (Citrate) Polymorph[1] |
| --- | --- | --- |
| IPA | 5° C. | Form X |
| Acetone | | Form X |
| TBME | | Pattern 2 + Form X |
| EtOAc | | Pattern 2 + Form X |
| H$_2$O | | Pattern 2 |
| THF:H$_2$O (9:1) | | Pattern 2 |
| DCM:H$_2$O (9:1) | | Pattern 2 + Form X |
| Acetone:H$_2$O (9:1) | | Pattern 2 |
| IPA | 25° C. | Form X |
| Acetone | | Form X |
| TBME | | Pattern 2 + Form X |
| EtOAc | | Form X |
| H$_2$O | | Pattern 2 |
| THF:H$_2$O (9:1) | | Pattern 2 |
| DCM:H$_2$O (9:1) | | Pattern 2 |
| Acetone:H$_2$O (9:1) | | Pattern 2 |
| IPA | 50° C. | Form X |
| Acetone | | Form X |
| TBME | | Form X |
| EtOAc | | Form X |
| H$_2$O | | Pattern 2 |
| THF:H$_2$O (9:1) | | Pattern 2 |
| DCM:H$_2$O (9:1) | | Form X |
| Acetone:H$_2$O (9:1) | | Pattern 2 |

[1]See Example 4 for discussion of Pattern 2

Characterization: Form X (citrate) is a non-solvated, non-hygroscopic crystalline form of TG02 citrate which remained unchanged by XRPD following storage at elevated temperatures and relative humidity levels (40° C./75% RH, 25° C./97% RH and 60° C./ambient RH) after 28 days. Proton NMR was consistent with the proposed structure. However, as the methylene protons of the citric acid overlapped with the D6-DMSO reference peak, the stoichiometric equivalence of citrate acid is slightly offset. Thermal gravimetric analysis revealed the sample lost 29.8% w/w between 190-230° C., possibly due to the dissociation of the salt. Differential scanning calorimetry thermal events included a single broad endotherm at 204.5° C. (366.9 J/g). Analysis of the thermal events monitored at two different heating rates (2° C. and 10° C.) revealed a significant change in both melt temperature and enthalpy (192.1° C., 336.2 J/g and 205.3° C., 378.2 J/g). This finding suggests the observed endotherm is not a pure melt (thermodynamic) but also consists of a kinetic component possibly the dissociation of the citrate. HPLC purity analysis resulted in a purity reading of 97.6%. GVS analysis showed the material to be non-hygroscopic, with an uptake of 0.13% between 0-90% RH, with a maximum difference of 0.04% hysteresis between 40-60% RH. The sample remained unchanged by XRPD following GVS analysis. Thermodynamic solubility determination produced a reading of 0.64 mg/ml solubility in aqueous media.

The XRPD of Form X (citrate) is shown in FIG. 11. Table 12 lists the peak positions, d values, and relative peak intensities of TG02 Form X (citrate).

TABLE 12

| Index | Angle (2-Theta °) | d value (Å) | Relative Intensity |
| --- | --- | --- | --- |
| 1 | 8.6 | 10.3 | 10.7% |
| 2 | 9.4 | 9.4 | 12.8% |
| 3 | 11.9 | 7.4 | 13.0% |
| 4 | 12.5 | 7.1 | 8.6% |
| 5 | 14.3 | 6.2 | 9.8% |
| 6 | 15.2 | 5.8 | 33.4% |
| 7 | 15.5 | 5.7 | 47.7% |
| 8 | 16.1 | 5.5 | 14.6% |
| 9 | 16.4 | 5.4 | 6.9% |
| 10 | 17.0 | 5.2 | 22.3% |
| 11 | 17.4 | 5.1 | 18.4% |
| 12 | 17.9 | 5.0 | 7.6% |
| 13 | 19.0 | 4.7 | 8.6% |
| 14 | 19.6 | 4.5 | 13.2% |
| 15 | 20.3 | 4.4 | 9.0% |
| 16 | 20.6 | 4.3 | 9.1% |
| 17 | 21.2 | 4.2 | 5.3% |
| 18 | 21.7 | 4.1 | 33.5% |
| 19 | 22.1 | 4.0 | 31.4% |
| 20 | 23.0 | 3.9 | 100.0% |
| 21 | 23.5 | 3.8 | 5.6% |
| 22 | 23.9 | 3.7 | 7.4% |
| 23 | 24.2 | 3.7 | 5.1% |
| 24 | 24.8 | 3.6 | 9.1% |
| 25 | 26.2 | 3.4 | 21.9% |
| 26 | 27.3 | 3.3 | 7.1% |
| 27 | 28.0 | 3.2 | 8.3% |
| 28 | 29.9 | 3.0 | 21.1% |

Example 4

TG02 Citrate Patterns of U.S. Pat. No. 9,120,815

Figure 1:
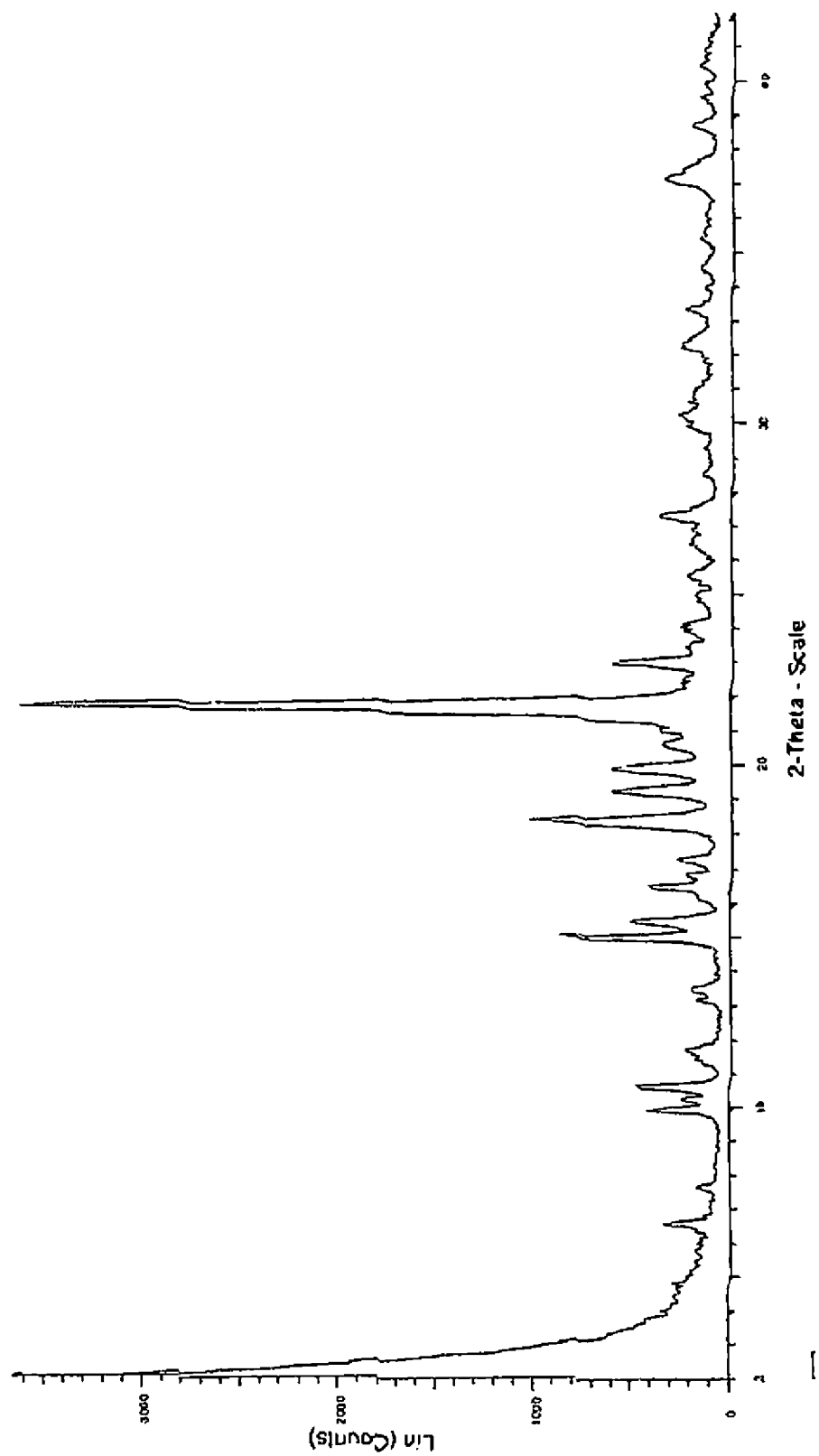
FIG. 1 is a PXRD of Citrate Pattern 1 of U.S. Pat. No. 9,120,815.

TG02 Citrate Pattern 1 ("Pattern 1") of U.S. Pat. No. 9,120,815 is a non-solvated, slightly hygroscopic crystalline form of TG02 citrate, which remained unchanged by XRPD following storage at elevated temperatures and relative humidity (40° C./75% RH, 25° C./97% RH and 60° C./ambient RH) for 28 days. Proton NMR analysis was consistent with the proposed structure, although there was overlap of the methylene protons of the citrate and the D6-DMSO reference peak. Thermal gravimetric analysis showed a weight loss of 29.6% w/w between 180-240° C., possibly due to loss of citrate. Differential scanning calorimetry revealed a single endothermic event at 196.6° C. (327.7 J/g). Comparing DSC profiles of the material at two different heating rates (2° C. and 10° C.) showed a large difference in onset temperature and enthalpy. This observation suggest the endotherm is likely due to both melt of the material (thermodynamic) and loss of the citrate (kinetic). HPLC purity analysis resulted in a purity reading of 97.7%. GVS analysis showed the material to be slightly-hygroscopic, with an uptake of 1.0% between 0-90% RH and a maximum hysteresis of 0.2% between 40-50% RH. The sample remained unchanged by XRPD following GVS analysis. Thermodynamic solubility determination produced a reading of 0.33 mg/ml solubility in aqueous media. XRPD following thermodynamic solubility analysis revealed a form change from TG02 Citrate Pattern 1 to TG02 Citrate Pattern 2 (both of U.S. Pat. No. 9,120,815). The XRPD of Pattern 1 is shown in FIG. 1.

Figure 2:
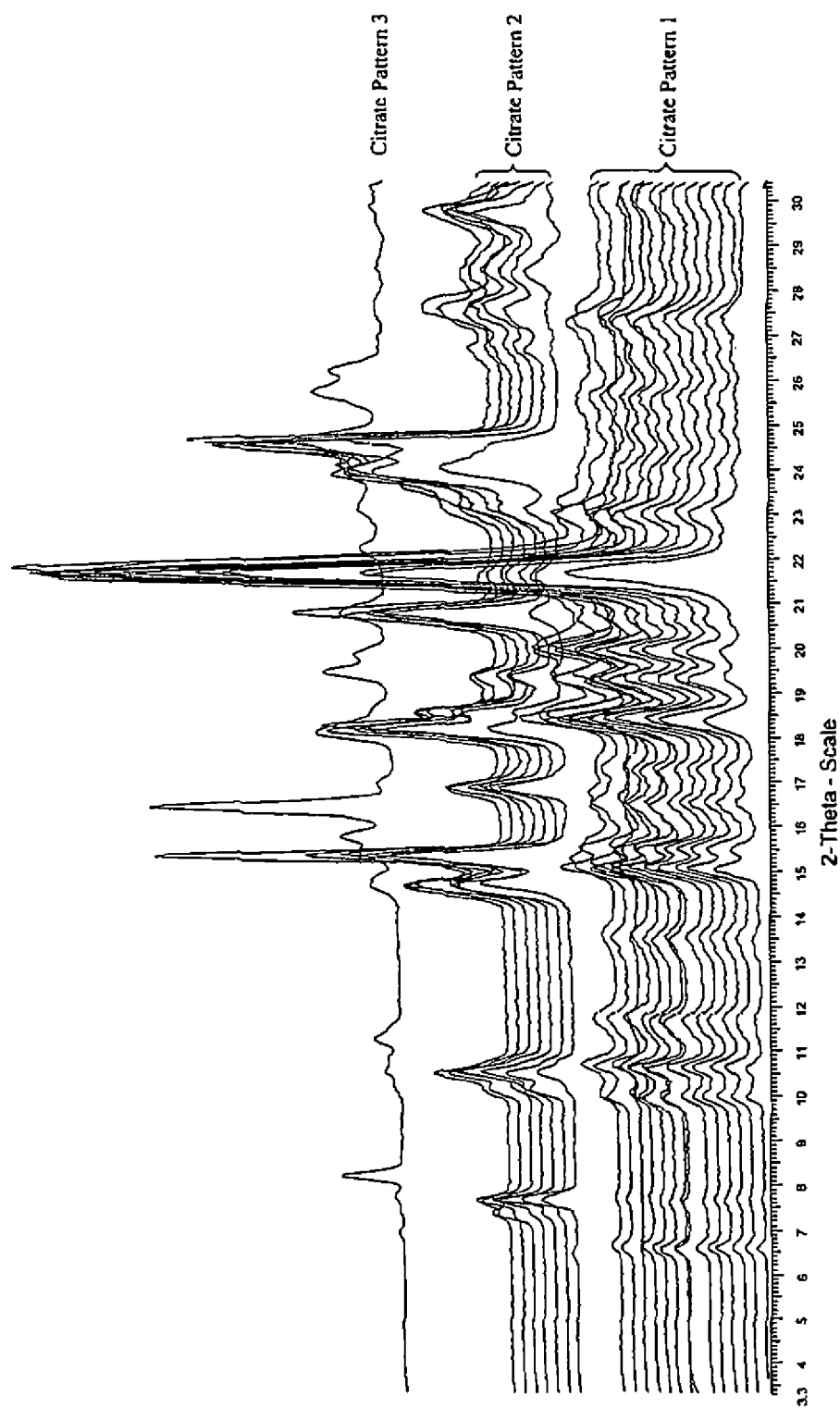
FIG. 2 is the PXRD of Citrate Patterns 1, 2, and 3 of U.S. Pat. No. 9,120,815.

TG02 Citrate Pattern 2 ("Pattern 2") of U.S. Pat. No. 9,120,815 defined as a hydrated, hygroscopic crystalline form of TG02 citrate, which remained unchanged by XRPD following storage at elevated temperatures and relative humidity (40° C./75% RH and 25° C./97% RH) for 28 days. However, storage at 60° C./ambient RH resulted in additional peaks being present in the XRPD diffractogram after 7 days. These additional peaks remained throughout the 28 days storage period. This may be caused by dehydration of the hydrate. Proton NMR analysis was consistent with the proposed structure, although there was overlap of the methylene protons of the citrate and the $D_6$-DMSO reference peak. Thermal gravimetric analysis showed two weight losses: a weight loss of 3.1% w/w between 25-115° C., possibly due to loss of water, followed by a weight loss of 29.5% w/w between 180-240° C., possibly due to the dissociation of citrate. Differential scanning calorimetry consisted of a broad, asymmetrical endotherm between 25-115° C. (70.2 J/g) followed by a large endotherm at 186.0° C. (313.4 J/g), possibly due to the sample melt and dissolution of the salt. HPLC purity analysis resulted in a purity reading of 97.7%. GVS analysis showed the material to be hygroscopic, with an uptake of 3.84% between 0-90% RH, with a maximum hysteresis of 1.4% between 10-30% RH. The sample remained unchanged by XRPD following GVS analysis. Water content was determined by Karl Fischer analysis to be 3.3%, equating to 1 molar equivalent of water. Thermodynamic solubility determination produced a reading of 0.23 mg/ml solubility in aqueous media and remained unchanged by XRPD. The XRPD of Pattern 2 is shown in FIG. 2.

Example 5

Photostability

The photostability of Pattern 1 and Pattern 2 of U.S. Pat. No. 9,120,815, and Form X (citrate) was investigated to determine whether light exposure results in substance changes.

A thin layer (≤3 mm) of Pattern 1, Pattern 2, and Form X (citrate) was placed in a clear glass HPLC vial. These samples were prepared in duplicate; one set to be kept in the dark (wrapped in aluminium foil) and the other exposed to light. Images of the HPLC vials were taken before and after light exposure. Samples were exposed to irradiation (765 W/m2) for 6.9 h, equating to one weeks Miami sunshine.

No visual change in appearance, XRPD, or purity of each sample was noted.

Example 6

Pharmaceutical Compositions

Compatibility experiments were conducted to select excipients for TG02 Form X (citrate) for use in gelatin capsules. Binary mixtures (1:1) of an excipient and TG02 Form X (citrate) were prepared, mixed, and stored at 40°/75% RH in open and closed containers for four weeks. Blend appearance and HPLC test results (chromatographic purity and assay) obtained after four weeks of storage in both open and closed configurations were compared to the initial results (Table 13 and Table 14). No significant appearance changes were noted over the course of the study. The list of compatible and incompatible excipients is provided in Table 15.

TABLE 13

Excipient Compatibility Results, 40° C./75% RH, Open Configuration

| Excipient | Initial | | 4 weeks | |
|---|---|---|---|---|
| | Purity (%) | Assay (%) | Purity (%) | Assay (%) |
| Avicel | 96.06 | 100.92 | 96.69 | 99.99 |
| Prosolv | 96.48 | 101.04 | 96.66 | 101.24 |
| Mannitol | 96.67 | 100.91 | 96.65 | 99.06 |
| Lactose Monohydrate | 96.65 | 100.27 | 96.69 | 99.89 |
| HPMC | 96.66 | 101.85 | 96.67 | 98.41 |
| PVP | 96.67 | 100.75 | 96.67 | 98.81 |
| PRUV | 96.41 | 83.93 | 96.13 | 71.01 |
| Mg Stearate | 96.65 | 90.42 | 96.67 | 99.92 |
| Croscarmellose | 96.36 | 73.46 | 96.36 | 76.23 |
| Explotab | 96.58 | 91.95 | 96.60 | 92.77 |
| Crospovidone | 96.64 | 98.61 | 96.67 | 98.88 |
| Avicel + SLS | 96.67 | 100.29 | 96.65 | 100.32 |
| Control | 96.66 | 100.96 | 96.68 | 98.29 |

TABLE 14

Excipient Compatibility Results, 40° C./75% RH, Closed Configuration

| Excipient | Initial | | 4 weeks | |
|---|---|---|---|---|
| | Purity (%) | Assay (%) | Purity (%) | Assay (%) |
| Avicel | 96.06 | 100.92 | 96.70 | 103.27 |
| Prosolv | 96.48 | 101.04 | 96.68 | 100.34 |
| Mannitol | 96.67 | 100.91 | 96.62 | 96.84 |
| Lactose Monohydrate | 96.65 | 100.27 | 96.63 | 98.71 |
| hPMC | 96.66 | 101.85 | 96.60 | 95.40 |
| PVP | 96.67 | 100.75 | 96.64 | 97.55 |
| PRUV | 96.41 | 83.93 | 96.24 | 72.60 |
| Mg Stearate | 96.65 | 90.42 | 96.68 | 96.10 |
| Croscarmellose | 96.36 | 73.46 | 96.29 | 69.92 |
| Explotab | 96.58 | 91.95 | 96.58 | 93.96 |
| Crospovidone | 96.64 | 98.61 | 96.67 | 100.14 |
| Avicel + SLS | 96.67 | 100.29 | 96.62 | 102.09 |
| Control | 96.66 | 100.96 | 96.66 | 94.38 |

TABLE 15

Results Summary of TG02 Form X (citrate) Excipient Compatibility

| Excipient Function | Compatible Excipients | Potentially Incompatible Excipients |
|---|---|---|
| Fillers | Microcrystalline cellulose Silicified microcrystalline cellulose Lactose monohydrate Mannitol | |
| Binders | Crospovidone Hydroxypropyl methylcellulose | |
| Disintegrants | Crospovidone Sodium starch glycolate | Croscarmellose sodium |
| Lubricants | Magnesium stearate Sodium steoryl fumarate (PRUV) | |
| Wetting Agents | Sodium lauryl sulfate | |
| Capsule Shell | Gelatin | |

Representative TG02 Form X (citrate) formulation compositions are provided in Table 16. The capsules are an immediate release dosage form provided in two strengths: 50 mg and 150 mg. The capsule fill is a dry powder formulated blend of TG02 Form X (citrate) and excipients. The labelled strength of the TG02 Form X (citrate) capsules is in terms of TG02 base, while the batch formula is in terms of the TG02 Form X (citrate) salt. For example, the 50 mg strength of TG02 Form X (citrate) capsules contains about 76 mg of TG02 Form X (citrate) to account for the citric acid content of the drug substance total mass. Additional compositions are provided in Table 17.

TABLE 16

Formulation Compositions for TG02 Form X (citrate) Capsules

| Strength: | 50 mg | 150-mg |
|---|---|---|
| Name: | TG02 | TG02 |
| Capsule Size | 2 | 0 |
| Capsule Color | Swedish Orange | Light blue |

| Ingredient | Function | Composition (mg/capsule) | |
|---|---|---|---|
| TG02 citrate | Active | 76.23 | 228.6 |
| Silicified Microcrystalline Cellulose, NF | Filler | 111.72 | 93.6 |
| Crospovidone, Ph. Eur., NF, JP | Disintegrant | 10.50 | 18.0 |
| Hypromellose 2910, Ph. Eur., USP, JP | Binder | 10.50 | 18.0 |
| Magnesium Stearate, NF | Lubricant | 1.05 | 1.8 |
| Total Fill Weight (mg): | | 210.0 | 360.0 |

TABLE 17

Formulation Composition for TG02 Form X (citrate) Capsules

| | Strength (mg) | | |
|---|---|---|---|
| Ingredient | 10 mg | 10 mg | 150 mg |
| TG02 Citrate | 15.6 | 15.6 | 234.0 |
| Silicified Microcrystalline Cellulose, NF | 172.3 | 172.3 | 106.2 |
| Crospovidone, NF | 10.5 | 10.5 | 19.0 |
| Hypromellose 2910, USP | 10.5 | 10.5 | 19.0 |
| Magnesium Stearate, NF | 1.1 | — | 1.8 |
| Sodium stearyl fumarate, NF (PRUV) | — | 1.1 | — |

Having now fully described the methods, compounds, and compositions herein, it will be understood by those of skill in the art that the same can be performed within a wide and equivalent range of conditions, formulations, and other parameters without affecting the scope of the methods, compounds, and compositions provided herein or any embodiment thereof. All patents, patent applications and publications cited herein are fully incorporated by reference herein in their entirety.

What is claimed is:

1. A crystalline polymorphic form of the citrate salt of (16E)-14-methyl-20-oxa-5,7,14,26-tetraazatetracyclo[19.3.1.1(2,6).1(8,12)]heptacosa-1(25),2(26),3,5,8(27),9,11,16,21,23-decaene characterized as having a powder x-ray diffraction pattern with peaks at 15.2, 15.5, 21.7, 22.1, 23.0, 26.2, and 29.9 degrees 2Θ.

2. The crystalline polymorphic form of claim 1 having an average particle size distribution of about 10 μm or less.

3. The crystalline polymorphic form of claim 2 having an average particle size distribution of about 1 μm or less.

4. A pharmaceutical composition comprising the crystalline polymorphic form of claim 1 and one or more pharmaceutically acceptable excipients.

5. The pharmaceutical composition of claim 4 comprising, by weight:
(a) about 7% to about 70% of the crystalline polymorphic form;
(b) about 20% to about 83% of a filler;
(c) about 1% to about 10% of a disintegrant;
(d) about 1% to about 10% of a binder; and
(e) about 0.1% to about 1% of a lubricant.

6. A kit comprising the crystalline polymorphic form of claim 1 and instructions for administering the crystalline polymorphic form to a patient having cancer.

7. The kit of claim 6 further comprising an immune checkpoint inhibitor or alkylating agent.

8. A method of making the pharmaceutical composition of claim 4, the method comprising admixing the crystalline polymorphic form and one or more pharmaceutically acceptable excipients.

9. A method of making the crystalline polymorphic form of claim 1, the method comprising:
(a) combining a solution of citric acid in ethanol with a solution of (16E)-14-methyl-20-oxa-5,7,14,26-tetraazatetracyclo[19.3.1.1(2,6).1(8,12)]heptacosa-1(25), 2(26),3,5,8(27),9,11,16,21,23-decaene free base in DMSO/ethanol;
(b) heating the solution of (a) at about 70° C. for at least about 15 minutes to give a solution comprising (16E)-14-methyl-20-oxa-5,7,14,26-tetraazatetracyclo [19.3.1.1(2,6).1(8,12)]heptacosa-1(25),2(26),3,5,8 (27),9,11,16,21,23-decaene citrate;
(c) cooling the solution of (b) comprising (16E)-14-methyl-20-oxa-5,7,14,26-tetraazatetracyclo[19.3.1.1 (2,6).1(8,12)]heptacosa-1(25),2(26),3,5,8(27),9,11,16, 21,23-decaene citrate to about 5° C. to give a crystalline solid; and
(d) isolating the crystalline solid of (c) to give the crystalline polymorphic form.

10. The pharmaceutical composition of claim 5 comprising, by weight, about 60% to about 65% of the crystalline polymorphic form.

11. The pharmaceutical composition of claim 10 comprising, by weight, about 25% to about 30% of a filler.

12. The pharmaceutical composition of claim 11, wherein the filler is selected from the group consisting of microcrystalline cellulose, silicified microcrystalline cellulose, lactose monohydrate, and mannitol.

13. The pharmaceutical composition of claim 12 comprising, by weight: (a) about 63.5% of the crystalline polymorphic form; (b) about 26% of silicified microcrystalline cellulose; (c) about 5% of crospovidone; (d) about 5% of hydroxypropyl methylcellulose; and (e) about 0.5% of magnesium stearate.

14. The pharmaceutical composition of claim 5 comprising, by weight, about 35% to about 40% of the crystalline polymorphic form.

15. The pharmaceutical composition of claim 14 comprising, by weight, about 50% to about 55% of a filler.

16. The pharmaceutical composition of claim 15, wherein the filler is selected from the group consisting of microcrystalline cellulose, silicified microcrystalline cellulose, lactose monohydrate, and mannitol.

17. The pharmaceutical composition of claim 16 comprising, by weight: (a) about 36.3% of the crystalline polymorphic form; (b) about 53.2% of silicified microcrystalline cellulose; (c) about 5% of crospovidone; (d) about 5% of hydroxypropyl methylcellulose; and (e) about 0.5% of magnesium stearate.

18. The pharmaceutical composition of claim 5 comprising, by weight, about 7% to about 10% of the crystalline polymorphic form.

19. The pharmaceutical composition of claim 18 comprising, by weight: (a) about 7.5% of the crystalline polymorphic form; (b) about 82% of silicified microcrystalline cellulose; (c) about 5% of crospovidone; (d) about 5% of hydroxypropyl methylcellulose; and (e) about 0.5% of magnesium stearate.

20. The pharmaceutical composition of claim 5 for oral administration in a capsule.

\* \* \* \* \*